United States Patent [19]
Ratain et al.

[11] Patent Number: 5,786,344
[45] Date of Patent: Jul. 28, 1998

[54] CAMPTOTHECIN DRUG COMBINATIONS AND METHODS WITH REDUCED SIDE EFFECTS

[75] Inventors: Mark J. Ratain; Elora Gupta, both of Chicago, Ill.

[73] Assignee: Arch Development Corporation, Chicago, Ill.

[21] Appl. No.: 423,641

[22] Filed: Apr. 17, 1995

Related U.S. Application Data

[63] Continuation-in-part of Ser. No. 271,278, Jul. 5, 1994, abandoned.

[51] Int. Cl.$^6$ .......................... A61K 31/545; A61K 31/47
[52] U.S. Cl. ........................................... 514/100; 514/211
[58] Field of Search ................................ 514/100, 211

[56] References Cited

FOREIGN PATENT DOCUMENTS

WO94/22846  10/1994  WIPO.

OTHER PUBLICATIONS

Ansher et al., "Chemoprotective Effects of Two Dithiolthiones and of Butylhydroxyanisole Against Carbon Tetrachloride and Acetaminophen Toxicity," *Hepatology*, 3(6):932–935, 1983.

Araki et al., Relationship Between Development of Diarrhea and the Concentration of SN–38, an Active Metabolite of CPT–11, in the Intestine and the Blood Plasma of Athymic Mice Following Intraperitoneal Administration of CPT–11, *Jpn. J. Cancer Res.*, 84:697–702, 1993.

Atsumi et al., "Identification of the Metabolites of Irinotecan, a New Derivative of Camptothecin, in Rat Bile and its Biliary Excretion," *Xenobiotica*, 21(9):1159–1169, 1991.

Boiteux–Antoine et al., "Comparative Induction of Drug-Metabolizing Enzymes by Hypolipidaemic Compounds," *Gen. Pharmac.*, 20(4):407–412, 1989.

Burger et al., "Pharmacokinetic Interaction Between Rifampin and Zidovudine," *Antimicrobial Agents and Chemotherapy*, 37(7):1426–1431, 1993.

Davies and Schnell, "Oltipraz–Induced Amelioration of Acetaminophen Hepatotoxicity in Hamsters," *Toxicology and Applied Pharmacology*, 109:29–40, 1991.

De Morais et al., "Biotransformation and Toxicity of Acetaminophen in Congenic RHA Rats with or without a Hereditary Deficiency in Bilirubin UDP–Glucuronosyltransferase," *Toxicology and Applied Pharmacology*, 117:81–87, 1992.

Egner et al., "Regulation of Phase 2 Enzyme Induction by Oltipraz and other Dithiolethiones," *Carcinogenesis*, 15(2):177–181, 1994.

Fournel et al., "Structure–dependent induction of bilirubin glucuronidation and lauric acid 12–hydroxylation by arylcarboxylic acids chemically related to clofibrate," *Biochimica et Biophysica Acta*, 842:202–213, 1985.

Hecht et al., "4–(Methylnitrosamino)–1–(3–pyridyl)–1–butanol (NNAL) and its glucuronide, metabolites of a tobacco–specific lung carcinogen, in the urine of black and white smokers," *Proceedings of the American Association for Cancer Research*, 35:1702, 1994.

Hjelle, Jerry J., "Hepatic UDP–Glucuronic Acid Regulation during Acetaminophen Biotransformation in Rats," *The Journal of Pharmacology and Experimental Therapeutics*, 237(3):750–756, 1986.

Lubet et al., "A Pleiotropic Response to Phenobarbital–Type Enzyme Inducers in the F344/NCr RAT," *Chemical Pharmacology*, 43(5):1067–1078, 1992.

Magdalou et al., "Peroxisome Proliferators as Inducers and Substrates of UDP–glucuronosyltransferases," *Biol. Cell.*, 77:13–16, 1993.

Manning and Franklin, "Induction of rat UDP–glucuronosyltransferase and glutathione S–transferase activities by L–buthionine–S,R–sulfoximine without induction of cytochrome P–450," *Toxicology*, 65:149–159, 1990.

Negoro et al., "Phase I Study of Weekly Intravenous Infusions of CPT–11, a New Derivative of Camptothecin, in the Treatment of Advanced Non–Small–Cell Lung Cancer," *Journal of the National Cancer Institute*, 83(16):1164–1168, 1991.

Ohe et al., "Phase I Study and Pharmacokinetics of CPT–11 With 5–Day Continuous Infusion," *Journal of the National Cancer Institute*, 84(12):972–974, 1992.

Prochaska and Fernandes, "Elevation of serum Phase II enzymes by anticarcinogenic enzyme inducers: markers for a chemoprotected state?," *Carcinogenesis*, 14(12):2441–2445, 1993.

Rothenberg et al., "Phase I and Pharmacokinetic Trial of Weekly CPT–11," *Journal of Clinical Oncology*, 11(11):2194–2204, 1993.

Rowinsky et al., "Phase I and Pharmacological Study of the Novel Topoisomerase I Inhibitor 7–Ethyl–10–[4–(1–piperidino)–1–piperidino]carbonyloxycamptothecin (CPT–11) Administered as a Ninety–Minute Infusion Every 3 Weeks," *Cancer Research*, 54:427–436, 1994.

Charuk et al., "Interaction of Rat Kidney P–Glycoprotein with a Urinary Component and Various Drugs Including Cyclosporin A," *Am. J. Physiol.*, 266:F66–F75, 1994.

(List continued on next page.)

*Primary Examiner*—Porfirio Nazario-Gonzalez
*Attorney, Agent, or Firm*—Arnold, White & Durkee

[57] ABSTRACT

This invention provides methods and combination formulations and kits to reduce the toxicity of camptothecin drugs, such as irinotecan (CPT-11). Disclosed are therapeutics and treatment methods employing such drugs in combination with agents that increase conjugative enzyme activity or glucuronosyltransferase activity, and agents that decrease biliary transport protein activity, such as cyclosporine A, the resultant effects of which are to decrease the significant side effects previously associated with treatment using these drugs.

30 Claims, 8 Drawing Sheets

OTHER PUBLICATIONS

De Lannoy et al., "Cyclosporin and Quinidine Inhibition of Renal Digoxin Excretion: Evidence for Luminal Secretion of Digoxin," *Am. J. Physiol*, 263:F613–F622, 1992.

Dhainaut et al., "New Triazine Derivatives as Potent Modulators of Multidrug Resistance," *J. Med. Chem.*, 35:2481–2496, 1992.

Gupta et al., "Metabolic Fate of Irinotecan in Humans: Correltaion of Glucuronidation with Diarrhea," *Cancer Research*, 54:3723–3725, Jul. 1994.

Hait et al., "Terfenadine (Seldane®): A New Drug for Restoring Sensitivity to Multidrug Resistant Cancer Cells," *Biochemical Pharmacology*, 45(2):401–406, 1993.

Hendricks et al., "Effect of P–Glycoprotein Expression on the Accumulation and Cytotoxicity of Topotecan (SK&F 104864), a New Campotthecin Analogue," *Cancer Research*, 52:2268–2278, Apr. 1992.

Michelson and Slate, "A Mathematical Model for the Inhibition of the Multidrug Resistance–Associated P–Glycoprotein Pump," *Bulletin of Mathematical Biology*, 56(2):207–223, 1994.

Narita et al., "Inhibition of Beta–Glucuronidase by Natural Glucuronides of Kampo Medicines Using Glucuronide of SN–38 (7–ethyl–10–hydroxycamptothecin) as a Substrate," *Xenobiotica*, 23(1):5–10, Jan. 1993.

Ohi et al., "Intravesical Instillation of Adriamycin in the Prescence or Absence of Verapamil for the Treatment of Superficial Bladder Cancer: Preliminary Report of a Collaborative Study," *Cancer Chemother. Pharmacol.*, 30:S50–S54, 1992.

Perez et al., "Mechanisms and Modulation of Resistance to Chemotherapy in Ovarian Cancer," *Cancer Supplement*, 71(4):1571–1580, Feb. 1993.

Saeki et al., "Human P–Glycoprotein Transports Cyclosporin A and FK506," *The Journal of Biological Chemistry*, 268(9):6077–6080, 1993.

Sakata et al., "Preventive Effect of TJ–14, a Kampo (Chinese herb) Medicine, on Diarrhea Induced by Irinotecan Hydrochloride (CPT–11)," *Gan–To–Kagaku–Ryoho*, 21(8):1241–4, Jul. 1994; Abstract only.

Slichenmyer et al., "The Current Status of Camptothecin Analogues as Antitumor Agents," *Journal of the National Cancer Institute*, 85(4):271–291, Feb. 1993.

Slichenmyer et al., "Camptothecin Analogues: Studies from The Johns Hopkins Oncology Center," *Cancer Chemother. Pharmacol.*, 34:S53–S57, 1994.

Watanabe et al., "Kinetic Analysis of Hepatobiliary Transport of Vincristine in Perfused," *Journal of Hepatology*, 16:77–88, 1992.

Zacherl et al., "Inhibition of P–Glycoprotein–Mediated Vinblastine Transport Across HCT–8 Intestinal Carcinoma Monolayers by Verapamil Cyclosporine A and SDZ PSC 833 in Dependece on Extracellular pH," *Cancer Chemother. Pharmcol.*, 34:125–132, 1994.

Bertrand et al., "Sequential Administration of Camptothecin and Etoposide Circumvents the Antagonistic Cytotoxicity of Simultaneous Drug administration in Slowly Growing Human Colon Carcinoma HT–29 Cells," *Eur. J. Cancer*, 28A(4–5):743–748, 1992.

Kano et al., "Effects of CPT–11 in Combination with Other Anti–Cancer Agents in Culture," *Int. J. Cancer*, 50(4):604–610, 1992.

Karato et al., "Phase I Study of CPT–11 and Etoposide in Patients with Refractory Solid Tumors," *J. Clin. Oncol.*, 11(10):2030–2035, Oct. 1993.

Kaufmann, "Antagonism Between Camptothecin and Topoisomerase II–Directed Chemotherapeutic Agents in a Human Leukemia Cell Line," *Cancer Res.*, 51(4):1129–1136, Feb. 1991.

Rowinsky et al., "Taxcol: Pharmacology, Metabolism and Clinical Implications," *Cancer Surv.*, 17:283–304, 1993.

Taudou et al., "Inhibition of DNA Synthesis and DNA Fragmentation in Stimulated Splenocytes by the Concentrated Action of Topoisomerase I and II Poisons," *Biochem. Pharmacol.*, 45(2):331–337, 1993.

Zhang et al., "Inhibitory Effects of Homoharringtonine and Hydroxycamptothecin in Combination with Other Agents on Cancer Cell Growth," *Asia Pac. J. Pharmacol.*, 7:191–195, 1992.

PCT Search Report dated Jul. 5, 1995.

Cordon–Cardo et al., "Expression of the multidrug resistant gene product (P–glycoprotein) in human normal and tumor tissues," *J. Histochem. Cytochem.*, 38:1277–1287, 1990.

de Forni et al., "Phase I and pharmacokinetic study of the camptothecin derivative irinotecan administered on a weekly schedule in cancer patients," *Cancer Res.*, 54:4347–43554, 1994.

Foxwell et al., "Identification of the multidrug resistance–related P–glycoprotein as a cyclosporine binding protein," *Mol. Pharmacol.*, 36:543–546, 1989.

Kamimoto et al., "The function of GP–170, the multidrug resistant gene product, in rat liver canalicular membrane vesicles," *J. Biol. Chem.*, 264:11693–11698, 1989.

Lokeic et al., "Pharmacokinetics of irinotecan and its metabolites in human blood, bile and urine," *Cancer Chemother. Pharmacol.*, 36:79–82, 1995.

Lum et al., "Alteration of etoposide pharmacokinetics and pharmacodynamics by cyclosporine in a phase I trial to modulate multidrug resistance," *J. Clin. Oncol.*, 10:1635–1642, 1992.

Okamura et al., "Digoxin–cyclosporin A interaction: Modulation of the multidrug transporter P–glycoprotein in the kidney," *J. Pharmacol. Exp. Therap.*, 266:1614–1619, 1993.

Samuels et al., "Modulation of vinblastine resistance with cyclosporine: A phase I study," *Clin. Pharmacol. Ther.*, 54:421–429, 1993.

Schrenk et al., "Induction of multidrug resistance gene expression during cholestasis in rats and nonhuman primates," *Hepatol.*, 17:854–860, 1993.

Sinicrope et al., "Modulation of P–glycoprotein–mediated transport by alterations in lipid fluidity of rat liver canalicular membrane vesicles," *J. Biol. Chem.*, 267:24995–25002, 1992.

Tamai et al., "Competitive interaction of cyclosporins with the vinca alkaloid–binding site of P–glycoprotein in multidrug resistant cells," *J. Biol. Chem.*, 265:16509–16513, 1990.

Tsuruo et al., "Antitumor effect of CPT–11, a new derivative of camptothecin against pleiotropic drug–resistant tumors in vitro and in vivo," *Cancer Chemother. Pharmacol.*, 21:71–74, 1988.

Vore, "Canalicular transport: Discovery of ATP–dependent mechanisms," *Toxicol. Appl. Pharmacol.*, 118:2–7, 1993.

Taudou et al., Biochemical Pharmacology, vol. 45, No. 2, pp. 331–337 (1993).

Kaufmann, Cancer research, vol. 51, pp. 1129–1136 (1991).

Bertrand et al., Eur. J. Cancer, vol. 28A, No. 4/5, pp. 743–748 (1992).

CAMPTOTHECIN DRUG COMBINATIONS AND METHODS WITH REDUCED SIDE EFFECTS

The present application is a continuation-in-part of U.S. patent application Ser. No. 08/271,278, filed Jul. 5, 1994, abandoned, the entire text and figures of which disclosure is specifically incorporated herein by reference without disclaimer.

The U.S. Government may own rights in the present invention pursuant to Contract Number No:-CM-07301 and Grant Numbers CA-14599 and RO1 CA56078 from the National Institutes of Health.

BACKGROUND OF THE INVENTION

A. Field of the Invention

The present invention relates generally to the fields of reducing drug toxicity and enhancing drug efficacy. More particularly, it concerns new treatment methods, compositions and kits comprising camptothecin drugs, such as irinotecan (CPT-11) and topotecan, in combination with agents that reduce excretion of active camptothecin species through the bile. Agents that increase conjugative enzyme activity, such as glucuronosyltransferase activity, and agents that decrease p-glycoprotein activity, such as cyclosporine A, are particularly provided.

B. Description of the Related Art

Camptothecin was identified as the active component of the crude extract from the stem wood of Camptotheca acuminata that showed promising in vitro anti-neoplastic activities by inhibiting topoisomerase 1 (Wall et al., 1966). Camptothecin entered clinical trials in the early 1970s, but these were suspended (Muggia et al., 1972; Gottlieb et al., 1970). The drug exhibited marginal to partial responses to gastrointestinal malignancies and melanoma but resulted in severe dose-limiting hemorrhagic cystitis and unpredictable myelosuppression. In these trials, the sodium salt of the alkaloid was used which improved its water solubility but which also resulted in about 10 fold reduction of antitumor activity and an enhancement of toxicity (Wani et al., 1980; Giovanella et al., 1991). The reduced activity was due to the fact that camptothecins require a closed lactone ring structure for optimal activity. Formulation as the sodium salt resulted in opening of the ring to a hydroxy acid form that exhibited poor topoisomerase 1 inhibition.

Efforts have thus been directed towards synthesis of water-soluble derivatives of camptothecin that would have high antitumor activity and low toxicity. Topotecan was synthesized by the introduction of a basic side chain at the 9-position of the 10-hydroxycamptothecin ring. This enabled topotecan to retain its water solubility in the lactone form (Kingsbury et al., 1991). CPT-11 was synthesized by the introduction of an ethyl group at the 7-position of camptothecin and a hydroxyl group at the 10-position which formed an ester linkage with a piperidinopiperidino carbonyl group (Kunimoto et al., 1987). The ester linkage enhanced the polarity of the compound.

CPT-11 is a water-soluble semi-synthetic derivative that acts as a prodrug in vivo and is converted to SN-38 (7-ethyl-10-hydroxy-camptothecin) by the enzyme carboxyl esterase (Tsuji et al., 1991). SN-38 has been shown to undergo glucuronic acid conjugation to form the corresponding glucuronide which is the major elimination pathway of SN-38 (Atsumi et al., 1991). SN-38G is reported to be deconjugated by the intestinal microflora to form SN-38 (Kaneda et al., 1990). The topoisomerase I inhibition and single strand breaks after treatment with CPT-11 is determined primarily by SN-38 concentration (Kawato et al., 1991).

Accumulation of SN-38 in the intestine w as shown to be responsible for the diarrhea attributed to CPT-11 administration in nude mice (Araki et al., 1993). Thus the in vivo activity and toxicity of CPT-11 is dependent on SN-38 concentration, and characterization of the disposition of the metabolite following CPT-11 administration is important for designing optimal dosing schedules. Both diarrhea and myelosuppression have been significant concerns, with severe and/or life threatening toxicity being common.

In commenting on the use of CPT-11 and topotecan (TPT), Slichenmyer et al. (1993) proposed that decreased metabolic activation of the CPT-11 pro-drug and active efflux of TPT from the target cells by p-glycoprotein-mediated transport might contribute to the resistance to the cytotoxic effects of these agents seen in some cancer patients. To combat drug resistance, Slichenmyer et al. (1993) seem to be suggesting that increasing the activation enzyme activity, such as carboxyl esterase, or decreasing target cell p-glycoprotein activity may be effective.

However, the Slichenmyer proposals do not offer a solution to the toxicity associated with camptothecins. Moreover, increasing their metabolic activation, as suggested, may actually increase camptothecin toxicity, absent other methods of intervention. The further proposal of Slichenmyer et al. (1993) to combine camptothecins with other active chemotherapy agents, would also likely increase the toxic side-effects and thus limit benefit to the patient.

Prior studies have shown inconsistent relationships between the dose or pharmacokinetics of CPT-11 with SN-38 pharmacokinetics and gastrointestinal toxicity (Negoro et al., 1991; Ohe et al., 1992; Rothenberg et al., 1993; Rowinsky et al., 1994). Furthermore, there is little information on the metabolic fate of camptothecin drugs in humans, no clear definition of the plasma profile of SN-38G following CPT-11 administration in humans, and no accepted mechanism for reducing camptothecin toxicity. Despite the ongoing clinical trials, it is clear that a more in-depth understanding of CPT-11 metabolism is needed before safer treatments can be designed.

SUMMARY OF THE INVENTION

The present invention seeks to overcome these and other drawbacks inherent in the prior art by providing new treatment methods, compositions and kits for reducing the side effects of camptothecin drugs, such as irinotecan (CPT-11), topotecan and other camptothecin analogues. The invention provides methods for reducing the dose of a camptothecin compound necessary to achieve the same therapeutic benefit, and methods for using more usual dosages, or even increased doses, in order to achieve enhanced therapeutic effects. The methods of the invention generally rest in using a camptothecin compound in combination with an amount of a second agent effective to reduce excretion of the active camptothecin species through the bile.

The inventors have discovered that one mechanism underlying the significant toxicity of CPT-11, for example, is deficient glucuronidation of the CPT-11 metabolite, SN-38. The inventors further discovered that the active SN-38 species is transported into the bile, where it causes adverse effects, by the biliary transporter, p-glycoprotein. Therefore, advantageous methods for reducing excretion of active camptothecin species, such as SN-38, into the bile include increasing conjugative enzyme activity, such as glucuronosyltransferase activity; and decreasing the activity of biliary, or bile canaliculi, transport proteins, such as p-glycoprotein (FIG. 1).

The methods, compositions and kits of the invention may be used in conjunction with any camptothecin drug that has an active species or metabolite that is, at least in part, excreted through the bile. Such camptothecin drugs may themselves be the "active species". 9-AC, topotecan and GG211, amongst others, are examples of this group of camptothecin analogues. Alternatively, the camptothecin compound or drug may be one that is metabolized within the body to provide an active species or metabolite, such as CPT-11, which is converted to SN-38. Further examples of this class include 9-nitro-camptothecin, amongst others.

The types and ranges of camptothecin analogues available are well known to those of skill in the art and described in numerous texts. For example, Slichenmyer et al. (1994; 1993), Burris & Fields (1994) and Hawkins (1992), each incorporated herein by reference, review the use of camptothecins. It is contemplated that any of the compounds described in the above texts may be used in this invention.

Specific examples of active camptothecin analogues include seven-substituted water-soluble camptothecin analogues, as described by Emerson et al. (1995); hexacyclic camptothecin analogues, as described by Sugimori et al. (1994); and 20S configuration camptothecins with substitution at the 9 or 10 positions with amino, halogeno, or hydroxyl groups, 10,11-methylenedioxy substituted camptothecins and water-soluble 20-glycinate ester variants, each described by Wall et al. (1993). Also, E-ring-modified (RS)-camptothecin analogues, such as (RS)-20-deoxyamino-7-ethyl-10-methoxycamptothecin (Ejima et al., 1992); the water-soluble 9-[(dimethylamino)methyl]-10-hydroxycamptothecin of Kingsbury et al. (1991); and the 9- and 10-substituted camptothecins of Wani et al. (1987, 1986, 1980) may be used.

If desired, camptothecin analogues may be synthesized by following the methodology of, for example, Emerson et al. (1995); Sugimori et al. (1994); Wall et al. (1993); Ejima et al. (1992); Wani et al. (1980; 1987; 1986); Kingsbury et al. (1991) and Sugasawa et al. (1976), each incorporated herein by reference, and variations thereon.

In certain embodiments, the invention thus provides methods for reducing the toxicity of a camptothecin compound or drug, such as CPT-11, which comprise administering one or more camptothecin drugs in combination with an effective amount of one or more second agents that increase conjugative enzyme activity or that decrease biliary, or bile canaliculi, transport protein activity.

"Effective amounts" in certain circumstances are those amounts effective to reproducibly increase conjugative enzyme activity, or to decrease biliary transport protein activity, in comparison to their normal levels. Preferably, compounds that achieve significant appropriate changes in activity will be used. If desired, a battery of compounds may be screened in vitro to identify second agents for use in the present invention. Here, significant increases in conjugative enzyme activity, e.g., as measured using a glucuronosyl-transferase assay, are represented by increases of at least about 30%–40%, and most preferably, by increases of at least about 50%, with higher values of course being possible. Glucuronosyltransferase assays are well known in the art and may be conducted in vitro or in vivo.

Significant decreases in activity, when using a p-glycoprotein binding assay or a cellular or biliary transport assay, are represented by decreases of at least about 30%–40%, and most preferably, of at least about 50%, with more significant decreases also being possible. p-glycoprotein binding and inhibition assays are well known in the art, generally in the context of reversing multi-drug resistance (MDR). Assays may be conducted as described by Ichikawa-Haraguchi et al. (1993; incorporated herein by reference). One effective transport assay is that described by Thalhammer et al. (1994; incorporated herein by reference) that measures the p-gly coprotein-mediated transport of the cationic dye, acridine orange, across the bile canaliculi. Thalhammer et al. (1994) showed that this activity was inhibited by cyclosporine A and verapamil. Therefore, if a candidate substance exhibited inhibition in this type of study, it would likely be a suitable compound for use in the present invention.

However, quantitative in vitro testing is not a requirement of the invention as it is generally envisioned that the second agents will often be selected on the basis of their known properties or by structural and/or functional comparison to those agents disclosed herein. Therefore, the effective amounts will often be those amounts proposed to be safe for administration to animals in another context, for example, as disclosed herein. As the invention arises in part from the inventors' discovery of certain metabolic and physiological events, and the inventors' surprising combination of elements, there is considerable information available on the use and doses of second agents alone, which information may now be employed with the present invention.

So long as a dose of second agent that does not exceed previously quoted toxicity levels is not required, the effective amounts of the second agents may simply be defined as those amounts effective to reduce the side-effects or toxicity of one or more first camptothecin drugs when administered to an animal in combination with the first camptothecin drug(s). This is easily determined by monitoring the animal or patient and measuring those physical and biochemical parameters of health and disease that are indicative of the success of a given treatment. Such methods are routine in animal testing and clinical practice. Preferably, compounds that show a significant reduction in toxicity will be used, as will be determinable by the ordinary clinician.

In certain embodiments, the doses of camptothecin drugs, such as CPT-11 and other analogues, used in the present invention will often be less that those used in the prior art. Indeed, this is one advantage of the invention as it provides for a smaller dose to be given in order to achieve the same beneficial anti-cancer or other therapeutic results. For example, using CPT-11 with cyclosporine A, allows for about a three-fold reduction in the CPT-11 dose.

In other embodiments, the doses of camptothecin drugs administered may be about the same as those currently used in the art. In such cases, using the camptothecin compound in combination with a second agent that reduces biliary excretion of the active species or metabolite will result in increased bioavailability of the active component. This may be used, for example, in patients that have advanced disease or that have proven resistant to lower doses of camptothecins. Higher camptothecin levels may also be used, so long as the second agents are provided in amounts to prevent significant toxicity or untoward effects in the recipient animal or patient.

In any event, as the invention provides for reducing the toxicity of camptothecin drugs and for increasing the bioavailability of camptothecin drugs, it will be apparent that this invention provides for more variability in the doses of camptothecin species than previous methods. The attending physician may thus optimize treatment to the individual patient, effectively accounting for the variations in disease heterogeneity that were previously a problem.

The present invention also provides the opportunity for effective therapy without using a combination of chemotherapeutic agents. Although the use of additional drugs and chemotherapeutic combinations is contemplated in certain aspects of the invention, largely on a patient-by-patient basis, in many situations an advantage of this invention will be that other chemotherapeutics will not be necessary to achieve a significant response. This is beneficial as it will reduce overall toxicity and also remove the possibility of adverse, or even fatal, drug interactions.

In further embodiments, the camptothecin drug or drugs could be administered in combination with both one or more second agents that increase conjugative enzyme activity and one or more other second agents (or a so-called "third agents") that inhibit biliary transport or p-glycoprotein transport activity. This would give the added advantage of reducing the biliary excretion of the active camptothecin species by intervening in two different metabolic pathways.

It will be understood that the term "conjugative enzyme" as used herein, refers to enzymes that modify active camptothecin species. These enzymes are distinct from those "activation-type" enzymes that metabolize a pro-drug, such as CPT-11, into an active camptothecin species, such as SN-38. An example of such as enzyme is carboxyl esterase.

In terms of second agents that increase conjugative enzyme activity, such agents may increase phase I conjugative enzyme activity, but will preferably increases phase II conjugative enzyme activity. As used herein, the term "conjugative enzyme activity" is used to describe those enzymes that increase the water-solubility of metabolites, via conjugation, so that the resultant conjugate may be more readily excreted. The term "phase II conjugative enzyme" is also used to refer to enzymes that may be more commonly known as phase II enzymes.

Examples of phase I oxidative enzymes include the cytochrome P450 enzymes. Examples of phase II conjugative enzymes including the glucuronosyltransferase enzymes, glutathione S-transferase (GST), N-acetyl transferase, and even quinone reductase (QR) (Prochaska & Fernandes, 1992). As glucuronidation of SN-38 (an active metabolite of CPT-11) has been specifically observed in patients, compounds that increase glucuronosyltransferase enzyme activity are currently preferred.

Second agents that decrease or inhibit biliary transport and excretion are exemplified by agents that reduce transport of compounds into the bile, and even those that reduce bile flow, i.e., cholestatic agents. Inhibition of transport is generally achieved by inhibiting any membrane transport protein, or protein complex, that is present in the bile canaliculi and that functions to transport camptothecin analogues. The inventors discovered that p-glycoprotein transports the camptothecin species CPT-11, SN-38 and SN-38G, and the p-glycoprotein is thus a preferred target.

In the cancer treatment literature, p-glycoprotein is often referred to in the context of a target cell protein. Indeed, p-glycoprotein contributes to the multi-drug resistance phenotype observed in cancer cells by actively pumping drugs out of the cell. This type of drug efflux has made the cellular p-glycoprotein the subject of scientific research and certain studies on anti-cancer agents. However, it will be understood that such target cell p-glycoprotein studies are distinct from the approach taken by the present inventors that concerns biliary transport, i.e., the inventors have taken a whole animal approach rather than focusing on events at the ultimate target cells.

Although p-glycoprotein has been reported to be expressed in normal human tissues, such as liver, kidney, and adrenal gland, its function and transporting substrates in these tissues has not been determined (Ichikawa-Haraguchi et al., 1993).

To identify second agents capable of inhibiting p-glycoprotein transport activity, an initial screen may be conducted on the basis of p-glycoprotein binding, or inhibition of photoaffinity labeling of p-glycoprotein (Akiyama et al., 1988), followed by studies to confirm inhibitory activity. Inhibitory activity may be confirmed by competing for transport of labeled compounds in vitro, inhibiting the transport of labeled compounds in vitro, or even reversal of drug resistance in cells in vitro. Of course, it will be appreciated that animal testing and pre-clinical studies showing reduced camptothecin toxicity are the preferred means for optimizing the invention.

Virtually any method may be employed to increase the activity of a conjugative enzyme, such as glucuronosyltransferase, including increasing the levels of the enzyme, increasing the activity of a fixed amount of the enzyme, removing an inhibitor of the enzyme, and the like. For example, methods to increase the levels of a conjugative enzyme, such as glucuronosyltransferase, include increasing its transcription, translation or stability. Methods to increase the activity of such conjugative enzymes include administering specific or general activators of a given enzyme or enzyme family; removing any specific or general inhibitors, and such like. Known inducers of glucuronosyltransferase generally act by enhancing the de novo synthesis of the enzyme (Bock et al., 1978).

As to the inhibition of biliary transporter activity, e.g., p-glycoprotein activity, a variety of methods are again available. For example, decreasing the levels of the enzyme or transporter, decreasing the activity of a fixed amount of the enzyme or transporter, removing an activator or enhancer of the enzyme or transporter, and the like. Methods to decrease the levels of the p-glycoprotein transporter include decreasing its transcription, translation or stability. Methods to decrease the activity of the transporter include administering specific or general inhibitors of the p-glycoprotein transporter or transporter family; removing any specific or general activators, and such like.

As the present invention provides for increasing the amount of a conjugative enzyme, such as glucuronosyltransferase, and decreasing the amount of a transporter, such as p-glycoprotein, useful "second agents" also include recombinant vectors and constructs. For example, administering a recombinant form of a glucuronosyltransferase enzyme, or an antisense DNA construct that is complementary to p-glycoprotein transporter nucleic acid sequences, is envisioned. Second agent recombinant vectors are those that comprise a sequence region encoding a conjugative enzyme or an antisense version of a biliary transport protein, where the vectors are capable of expressing the sequence region in the type of mammalian that is to be treated.

Generally, increasing the activity or the amount of a conjugative enzyme using chemical agents will be preferred over molecular biological. Compounds that may be used as second agents to increase conjugative enzyme activity include those compounds that have been shown to be, or are believed to be, inducers of cytochrome P450 enzymes. These include, for example, cyclophosphamide; ifosphamide; phenytouin, available as DILANTIN INFATABS™, DILANTIN-30 PEDIATRIC™ and DILANTIN-125™ from Parke-Davis; disulfiram (also known as ANTABUSE™ available from ayerst); rifampin; clonazepam and clotrimazole (Lubet et al., 1992).

Barbiturates, such as phenobarbital, which are often used as anti-convulsants, may also be employed as second agents to activate conjugative enzymes. Indeed, using CPT-11 and phenobarbital, the inventors found a marked reduction in toxicity, as shown in Example 8. 3-methylcholanthrene may also be used to induce glucuronosyltransferases, where it induces different isoforms of the enzyme to phenobarbital (Rajaonarison et al., 1993; Burchell & Coughtrie, 1989).

Another group of compounds that may be used to increase conjugative enzyme activity are the retinoic acids, such as all trans retinoic acid, 9-cis retinoic acid and 13-cis retinoic acid. The anti-AIDS drug zidovudine (also known as AZT™ available from Burroughs Wellcon may also be used in limited circumstances, mostly in combination with rifampin, as described by Burger et al. (1993). Any of the many corticosteroids, e.g., those described in Table 5, could be employed, with dexamethasone as a particular example. Oral contraceptives, such as those described herein, form another possibility for use as second agents.

Compounds particularly contemplated for use as second, anti-toxicity agents in the context of increasing drug conjugation are those compounds that are known to be, or are believed to be, capable of promoting glucuronidation. These include L-buthionine-S,R-sulfoximine (BSO; Manning & Franklin, 1990); and anti-oxidants, such as butylated hydroxyanisole (BHA; tert-butyl-4-hydroxyanisole; Ansher et al., 1983).

Within the group of compounds that promote glucuronidation, two groups of compounds are currently preferred. First, the dithiolethiones (also known as dithiolthiones, Ansher et al., 1983), examples of which include 3H-1,2,-dithiole-3-thione; 3H-1,2,-dithiole-3-one; 1,3-dithiole-2-thione; [1,2]dithiolo[4,3-c]-1, 2-dithiole-3,6-dithione; 4-methyl-3H-1,2-dithiole-3-thione; 5-methyl-3H-1,2-dithiole-3-thione; 4,5-dimethyl-3H-1,2-dithiole-3-thione; 5-ethyl-3H-1,2-dithiole-3-thione; 5-ethyl-3H-1,2-dithiole-3-thione; 5-tert-butyl-3H-1,2-dithiole-thione; 3-thioxo-3 H-1,2-dithiole-4-carboxylic acid; 3-thioxo-3H-1, 2-dithiole-5-carboxylic acid; 3-thioxo-3H-1,2-dithiole-4-carboxamide; 3-thioxo-3H-1,2-dithiole-5-carboxamide; 4-phenyl-3H-1,2-dithiole-3 -thione; 5-phenyl-3H-1,2-dithiole-3-thione; 4-methyl-5-phenyl-3 H-1,2-dithiole-3-thione; 4-methyl-5-phenyl-3H-1,2-dithiole-3-thione-S-oxide; 4,5,6,7-tetrahydrobenzo-3H-1,2-dithiole-3-thione; 5,6-dihydrocyclopenta-1,2-dithiole-3 (4H)-thione; 4-methyl-5-pyrazinyl- 3H-1,2-dithiole-3-thione (oltipraz); 4-methyl-5-pyrazinyl-3H-1,2-dithiole-3-thione-S-oxide; 7-methyl-6,8-bis(methylthio)pyrrolo-[1,2-a]-pyrazine; 5-(4-methoxyphenol)-3H-1,2-dithiole-3-thione; 5-(4-methoxyphenol)-4-methyl-3H-1,2-dithiole-3-thione (Egner et al., 1994). Oltipraz (RP-35972; 4-methyl-5(2-pyrazinyl) -3H-1,2-dithiole-3-thione; available from Rhone-Poulenc) is particularly preferred, and has been shown to act upon acetaminophen (Davies & Schnell, 1991).

Further preferred compounds that are capable of promoting glucuronidation include those known as aryloxycarboxylic acids, arylcarboxylic acids, chlorophenoxycarboxylic acids or fibric acids, which compounds often function as hypolipidemic compounds (Boiteux-Antoine et al., 1989). Suitable aryloxycarboxylic and arylcarboxylic acids include clofibrate, ciprofibrate, fenofibrate, bezafibrate, gemfibrazol, tiadenol, probucol and the active compound 2-phenylpropionic acid (Magdalou et al., 1993; Fournel et al., 1985; Boiteux-Antoine et al., 1989). The term "clofibric acid" itself includes, 4'-chlorophenoxyacetic, 4'-chlorophenoxypropionic and 4'-chlorophenoxyisobutyric acids. All such fibric acids have been shown to be effective at inducing glucuronidation and are thus contemplated for use in the present invention.

Currently, preferred compounds for use in increasing conjugative enzyme activity are phenobarbital, Oltipraz, all-trans retinoic acid, phenytoin, dexamethasone, rifampin, and fibric acids, such as clofibrate. Oltipraz, all-trans retinoic acid, rifampin and phenobarbital are currently particularly preferred.

For reducing biliary transport, decreasing the activity of biliary transport proteins, rather than decreasing the number of such proteins, will generally be preferred. Compounds that may be used as second agents to inhibit biliary transporters, such as the p-glycoprotein transporter, include those compounds that have been shown to be, or are believed to be, general or specific inhibitors of membrane transport components, particularly of the p-glycoprotein transporter family. For example, as well as inhibitors that deactivate or modify the p-glycoprotein transporter (i.e., non-competitive inhibitors), agents that compete for p-glycoprotein binding sites and render the transporter less available for the camptothecin drug in question are contemplated (i.e., competitive inhibitors).

A currently particularly preferred group of second agents are immunosuppressants, such as cyclosporines, cyclosporine derivatives, and even cephalosporins, such as cefoperazone. Even non-immunosuppressive cyclosporine derivatives have p-glycoprotein-blocking capabilities. One such example is SDZ PSC 833, which is more effective than cyclosporine A (Boesch et al., 1991; Pourtier-Manzanedo et al., 1992; Boesch & Loor, 1994; Zacherl et al., 1994). SDZ 28-446 is another cyclosporine A analogue that may be employed (Pourtier-Manzanedo et al., 1992).

Cyclosporine A, C, G and H will generally be used, with cyclosporine A being particularly preferred. However, the cyclosporine D analogue 3'-Keto-cyclosporine D (Bell et al., 1994) may also be used. Results are presented herein (Example 19) to show that using cyclosporine A in combination with CPT-11 is particularly beneficial. Staurosporine and staurosporine derivatives, particularly NA-382, may also be employed (Miyamoto et al., 1992a; 1993).

Further examples of p-glycoprotein transporter inhibitors calcium channel blockers. One particularly useful group of compounds are the dihydropyridine analogues (Kamiwatari et al., 1989), and their clinical counterparts. Certain examples are verapamil, dex verapamil and their analogues (Ohi et al., 1992; Doige et al., 1992; Inoue et al., 1993; Hunter et al., 1993; Thalhammer et al., 1994; Muller et al., 1994; Bear, 1994; Boesch & Loor, 1994). Verapamil is known to be an effective competitive inhibitor of p-glycoprotein.

Other useful calcium channel blockers include tiapamil and tiapamil analogues, such as 1993RO-11-2933 (Campain et al., 1993); nifedipine and nifedipine analogues (Wilson et al., 1991; Doige et al., 1992; Hunter et al., 1993); diltiazem (Morris et al., 1991); nicardipine (Niwa et al., 1992); prenylamine; nimodipine; nisoldipine and nitrendipine.

Further examples of second agents that inhibit the p-glycoprotein transporter are calmodulin antagonists. This group of agents includes thioxanthenes, phenothiazines and flupenthixols, such as cis-flupenthixol, trans-flupenthixol and clorpenthixol (Ford et al., 1990; Hait et al., 1993). Other calmodulin antagonists include clomipramine, fluphenazine, chlorpromazine, triflupromazine, trifluoperazine, prochlorperazine and thioridazine.

Still further examples of second agents that inhibit the p-glycoprotein transporter are anti-neoplastic agents.

Although the invention encompasses a wide variety of other agents, the anti-neoplastic compounds may also be employed. Examples of these are vincristine (Shirai et al., 1994; Friche et al., 1993); vinblastine (Bear, 1994; McKinney & Hosford, 1993); actinomycin D (McKinney & Hosford, 1993); colchicine (Bear, 1994; McKinney & Hosford, 1993; Doige et al., 1992); etoposide; daunomycin (Bear, 1994); daunorubicin (Muller et al., 1994); doxorubicin (Mechetner & Roninson, 1992) and analogues, such as 14-O-hemiesters of doxorubicin; taxotere (Hunter et al., 1993); taxol (Mechetner & Roninson, 1992); and tamoxifen (Trump et al., 1992).

Yet further examples of second agents that inhibit the p-glycoprotein transporter are cationic compounds, such as reserpine; dipyridamole (DPM) (Suzuki, 1990; Tatsuta et al., 1991); chloroquine, quinacrine, propranolol, cepharanthine and other compounds described by Akiyama et al. (1988).

A diverse group of other agents have been shown to interact with and inhibit p-gly coprotein. For example, certain steroids (Chin et al., 1992), including pregnenolone, progesterone and metabolites (Ichikawa-Haraguchi et al., 1993; Gruol et al., 1994; Doige et al., 1992); RU 486; and 21-aminosteroid derivatives, lazaroids and tirilazad (Abraham et al., 1993). Dexamethasone is also contemplated for use in this aspect (Miller et al., 1991). Certain bile acids, such as taurochenodeoxycholate, glycochenodeoxycholate, taurolithocholate and ursodeoxycholate (Mazzanti et al., 1994) may also be used. Other agents that may be employed include anthracycline analogues such as DNR, N,N-dibenzyl-DNR and N-benzyladriamycin-14-valerate (AD-198) (Friche et al., 1993); terfenadine (Seldane) (Hait et al., 1993); certain dihydropyridine analogues (Suzuki, 1990; Kiue et al., 1990; Kamiwatari et al., 989); ivermectin (Schinkel et al., 1994); and quinidine (Akiyama et al., 1988).

Antibodies that binds to external epitopes of p-glycoprotein may also be used as second agents to achieve inhibition. Monoclonal antibodies (MAbs) will generally be preferred. Many such antibodies are known, as exemplified by MAb C219 (Miyamoto et al., 1992b) and MAbs JSB-1 and C-219 (Miller et al., 1991). The MAb UIC2 (Mechetner & Roninson, 1992), and others developed by the Schinkel group, such as HYB-241, 7G4 and 4E3, may also be used (Schinkel et al., 1993). The MAb MRK16 and the mouse-human chimeric version MH162 are preferred agents (Hamada et al., 1990), as is the mouse-human chimeric antibody, MH171 (Ariyoshi et al., 1992) and the MAb UIC2 (Mechetner & Roninson, 1992). MRK16, MH171 and UIC2 have been safely used in animals. Other useful monoclonal antibodies may also be obtained or prepared, so long as the MAb generally exhibits binding affinity for external epitopes of p-glycoprotein , as described by Schinkel et al. (1993).

Currently, preferred compounds for use in decreasing p-glycoprotein activity are cyclosporines and staurosporines, particularly, cyclosporine A, SDZ PSC 833, NA-382, and verapamil and dex verapamil.

The camptothecin class of drugs for use in the invention function to inhibit topoisomerase I and have various therapeutic uses. For example, 9-nitro-camptothecin has been applied in certain situations as an anti-parasitic agent, and camptothecin analogues have well-documented activity against resistant solid tumors, particularly colon, lung cancer and ovarian cancer, and refractory leukemia. CPT-11 itself has shown antitumor activity in phase II trials in patients with carcinomas of lung, cervix, ovary, colon, and rectum and in patients with non-Hodgkin's lymphoma. However, it will be appreciated that the camptothecins may be used to treat practically any cancer.

The use of such camptothecin drugs, e.g., CPT-11, has been previously limited by significant gastrointestinal toxicities, including nausea, vomiting and abdominal pain, which side effects can prove fatal. By modulating camptothecin drug toxicity, the present invention thus also provides improved methods for treating cancers, leukemias, parasitic infections and other diseases and disorders, as desired.

The treatment methods generally comprise administering to an animal with cancer, including a human patient, a therapeutically effective combination of one or more camptothecin drugs, such as CPT-11, and one or more second agents that reduce camptothecin toxicity by reducing excretion of the active camptothecin species through the bile, as exemplified by second agents that increase conjugative enzyme activity and/or that inhibit p-glycoprotein transport activity. The second agent(s) may be any of those listed above, and their functional equivalents.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

In addition to the type of animal studies described herein, the animal model studies described by Mattern et al. (1993), Takiguchi et al. (1994) and Kaneda et al. (1990), each incorporated herein by reference, may be employed in connection with the present invention. These studies demonstrated that camptothecin analogues are active against leukemias and metastatic cancers. Assessing drug combinations in various animal model systems of cancer is well known in the art and is not subject to the limitations of model systems for other diseases, such as AIDS, that render it difficult to translate the results to the clinic.

In some cases, pre-clinical testing in animals with disease may not be necessary where both the camptothecin drug and the second agent have been previously approved for human treatment. In any event, all that is required to determine or optimize a therapeutically effective amount for human treatment is to administer the first drug(s) in combination with an amount of one or more selected second agents and to monitor the patient to determine whether a benefit to the patient results. Preferably, one would use an amount that resulted in a significant benefit to the patient, as assessed by a significant reduction in camptothecin toxicity or any increase in the anti-tumor (or anti-parasitic) response. Optimal doses of the second agents may thus be readily identified following the general starting ranges, such as those found in the scientific literature and those detailed herein.

Animals and patients may also be treated with the camptothecin drug or drugs in combination with two or more second agents, with at least one agent being from the different classes described above. Here, the agents may also be described as a second agent and a third agent. This has the benefit of acting at two distinct points in the camptothecin excretion pathways and may result in further improved or even synergistic effects.

In treatment methods, the first camptothecin drug or drugs, e.g., CPT-11, may be administered to the animal or patient prior to administering the second agent(s), or the first drug(s) and the second agent(s) may be administered simultaneously. A single composition that comprises both the first drug(s) and one or more second agents may be employed for simultaneously administration, or distinct compositions that include only one of the formulations could be used. Where one or more third agents are used, a combined therapeutic cocktail may be prepared and administered if desired.

Using distinct compositions is generally preferred where the number of second agents is relatively low, as this can provide for more control of the individual doses. However, a cocktail may be preferred where the total number of components is larger, to minimize the discomfort to the animal or patient due to repeated administration.

It is currently preferred that the se cond agent be administered to the animal or patient prior to the camptothecin drug(s) in order to "prime" the system. Delivery of the second agent prior to the camptothecin drug and continued delivery of the second agent throughout the camptothecin delivery period is one currently preferred treatment method. "Delivery" in these contexts preferably means continuous infusion. Treatment with agents intended t o combat any myelosuppression, such as GCSF (GMCSF), is also contemplated, as is sometimes performed after the administration of a camptothecin drug.

One currently preferred treatment mode comprises administering about 25 mg/m$^2$ of CPT-11 by infusion over about 90 minutes, about 10 mg/kg cyclosporine A by infusion, and optionally, also about 60 mg/kg of phenobarbital.

Various other delivery methods may also be used, as desired by the attending physician. It will likely be convenient to employ standard delivery methods, such as parenteral administration, including continuous infusion and intravenous, intramuscular and subcutaneous injections. However, other methods, such as oral delivery may be employ ed, depend ing on the second agent used to reduce the toxicity or enhance the bioavailability of the first camptothecin drug(s).

There is significant guidance in the art as to how to achieve effective drug delivery. For instance, one may follow the methods and the use the dosages published by, e.g., Lubet et al. (1992); Burger et al. (1993); Manning & Franklin (1990); Ansher et al. (1983); Egner et al. (1994); Davies & Schnell (1991); Magdalou et al. (1993); Fournel et al. (1985); Boiteux-Antoine et al. (1989); Abigerges et al. (1995); Silber et al. (1994); Miki & Kotake (1993); and Kingsbury et al. (1991); each incorporated herein by reference. Suitable modifications to the doses and methods may be made, as necessary, which are readily determinable without undue experimentation by those of skill in the art. Further publications are available that review the use of camptothecin analogues, such as, e.g., Slichenmyer et al. (1994, 1993) and Hawkins (1992), each incorporated herein by reference.

Also provided are new compositions and formulations, including pharmacologically acceptable formulations, that comprise one or more first camptothecins, such as CPT-11, in combination with one or more second agents that increase conjugative enzyme activity or that decrease biliary transport protein activity. Such compositions may include the first camptothecin drug or drugs in combination with Oltipraz, clofibrate, ciprofibrate, fenofibrate, bezafibrate, gemfibrozol, tiadenol, probucol, phenobarbital, DILANTIN™, clonazepam, clotrimazole, buthionine sulfoximine (BSO), cyclophosphamide, ifosphamide, a retinoic acid, a corticosteroid, an oral contraceptive, rifampin or disulfiram (ANTABUSE™); and will preferably include CPT-11 in combination with phenobarbital, Oltipraz, all-trans retinoic acid, phenytoin, dexamethasone, rifampin or clofibrate.

The compositions may also include one or more first camptothecin drugs in combination with a cyclosporine or staurosporine, particularly, cyclosporine A or SDZ PSC 833, NA-382; and/or with verapamil or dex verapamil.

The compositions may also advantageously include the first camptothecin drug or drugs in combination with one or more second agents selected from the group that increases conjugative enzyme activity and one or more second or third agents selected from the group that decreases biliary transport protein activity.

The terms "pharmacologically or pharmaceutically acceptable", as used herein, refer to compositions that do not produce significant toxicity, detrimental side effects, or other untoward reactions, when given to an animal or patient. In that camptothecins such as CPT-11, prior to the present invention, were known to suffer from certain toxic limitations, it will be understood that "pharmaceutically acceptable" compositions may still have certain harmful effects when given to an animal. "Pharmaceutically acceptable" in the present context thus refers to other components, such as diluents, binders and the like, which should be selected from the pharmaceutically acceptable products available or developed using the same general guidelines.

Therapeutic kits comprising camptothecin drugs, such as CPT-11, and one or more second or third agents form another aspect of the invention. Such kits will generally contain, in suitable container means, a pharmaceutical formulation of the camptothecin drug(s), a pharmaceutical formulation of one or more second agents that increase conjugative enzyme activity or that decrease biliary transport protein activity. Multiple agents with different specificities may be employed. The kit may have a single container means with all the drugs and agents disposed therein or may have two, three or multiple distinct container means, one for each compound or group of similar-acting compounds.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

The components of the kit may be provided in one or more fluid or syringeable compositions. In which case, the container means may itself be an intravenous delivery bag, a syringe, pipette, eye dropper, or other such like apparatus, from which the formulation may be infused or injected into an animal, applied to a diseased area of the body, or even applied to and mixed with the other components of the kit.

The container means of the kit will generally be at least one intravenous delivery fluid bag, vial, test tube, flask, bottle, syringe or other suitable container into which the drugs and/or agents may be placed, and preferably, suitably allocated. The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the infusion, injection or administration of the ultimate composition to an animal. Such an instrument may be a syringe, one or more delivery tubes, or even an eye dropper or a measuring spoon, or any such medically approved delivery vehicle.

The invention also provides method for predicting the degree of camptothecin drug, such as CPT-11, toxicity that may arise in a patient. One such method generally comprises determining the glucuronidation capacity of the patient, wherein a decreased glucuronidation capacity, in comparison to normal levels, would be indicative of a patient at risk of developing drug toxicity, if a drug such as CPT-11 were to be given alone.

Another such method generally comprises determining the biliary transport capacity of the patient, wherein an increased biliary transport capacity, such as p-glycoprotein activity, in comparison to normal levels, would be indicative of a patient at risk of developing drug toxicity, if a CPT-11-like drug were to be administered alone.

Certain of the diagnostic methods may employ "genotyping", i.e., assaying for genetic polymorphisms in enzymes involved in the metabolism of camptothecins, particularly CPT-11. Here, the glucuronidation or biliary transport capacity of the patient is determined by means of determining the amount of DNA or RNA encoding a glucuronosyltransferase enzyme or a biliary transport protein such as p-glycoprotein. The execution of such molecular biological methods is well known in the art, and includes, for example, Southern and Northern blotting performed by contacting nucleic acids from a biological sample of the patient with a DNA (or RNA) segment that encodes a mammalian glucuronosyltransferase enzyme or a biliary transport protein, such as p-glycoprotein. This is done under conditions effective to allow hybridization of substantially complementary nucleic acids, and the hybridized nucleic acid complexes thus formed are later detected using a detectable label, such as a radiolabel.

In preferred embodiments, the diagnostic methods will generally be "phenotypic" in nature, for example, wherein the glucuronidation capacity of a patient is determined by administering a glucuronidatable substrate, such as acetaminophen, diflunisal or morphine, to the patient and then determining the degree of glucuronidation of the substrate, e.g., by detecting the substrate-glucuronide conjugate by HPLC.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A is a representative plasma profile of a patient having grade 0–2 diarrhea. FIG. 2B is a representative plasma profile of a patient having grade 3–4 diarrhea.

Patients were grouped as having either grade 0–2 diarrhea or grade 3–4 diarrhea based on the first two cycles of treatment. The median value for the two groups were 2228 (n=12) and 5499 (n=9). One patient with grade 3–4 diarrhea had an index value of 3028, tested positive for Clostridium difficile toxin and is indicated by (c diff+). The nonparametric Mann Whitney test demonstrated a significant correlation of "biliary index" to severity of diarrhea (p=0.0004).

Figure 4A:
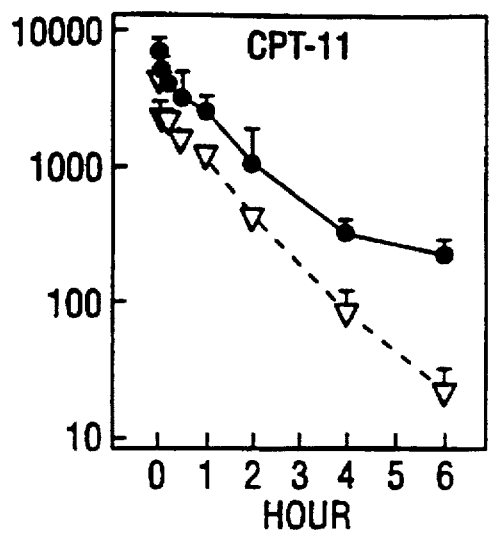
Figure 4B:
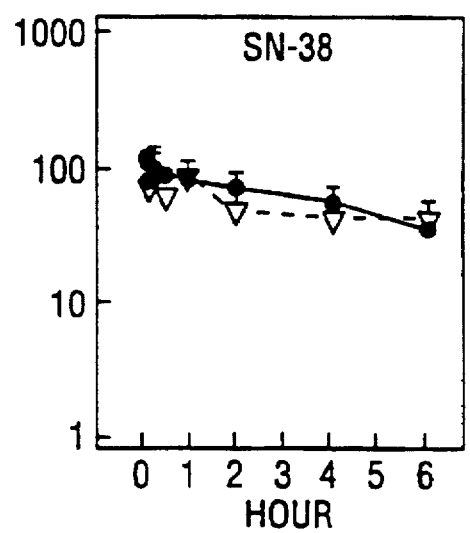
Figure 4C:
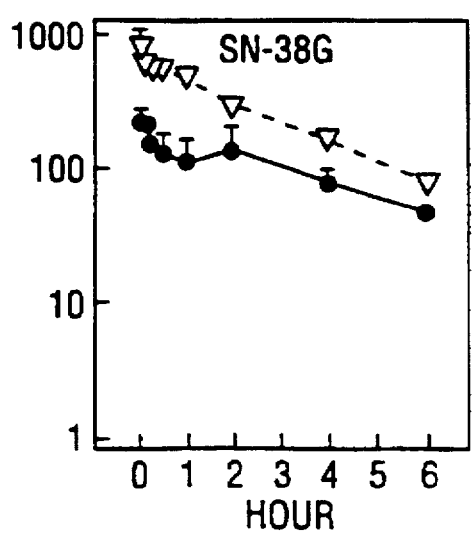

FIG. 4A, FIG. 4B and FIG. 4C. Plasma concentrations of CPT-11 (FIG. 4A), SN-38 (FIG. 4B) and SN-38G (FIG. 4C) in control ( CPT-11 dose: 20 mg/kg, n=4) versus phenobarbital pretreated rats (n=2), receiving the same dose of CPT-11. Data is represented as mean+SD for the control group as mean for the pretreated group.

Figure 5:
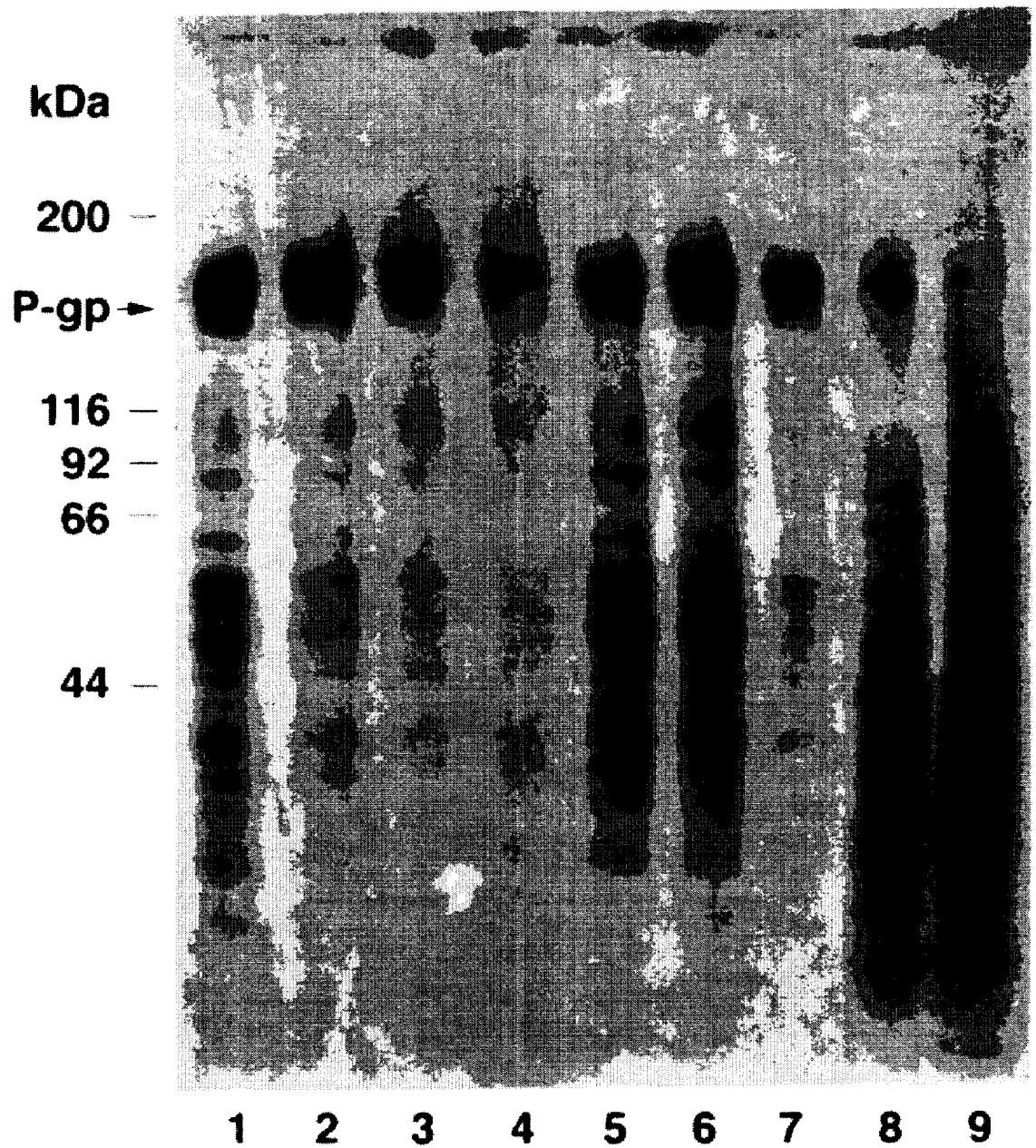

FIG. 5. SDS-PAGE fluorography of [$^3$H]verapamil photoaffinity labeled plasma membranes of MCF-7/Adr cells and inhibitory effects of CPT-11 and SN-38 in comparison to verapamil. Cells were labeled with [$^{125}$I]verapamil in the absence (Lane 1) and presence of 10 μM and 100 μM CPT-11 (Lane 3 and Lane 4), or 10 μM and 100 μM SN-38 (Lane 6 and Lane 7) or 10 μM and 100 μM verapamil (Lane 8 and Lane 9). Both CPT-11 and SN-38 reduce photoaffinity labeling of the cells by competing with [$^3$H]verapamil.

Figure 6A:
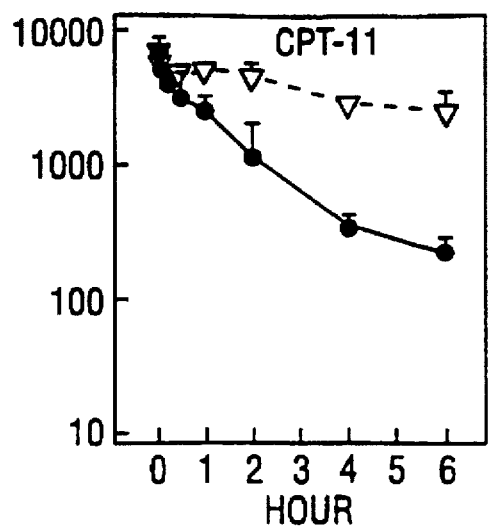
Figure 6B:
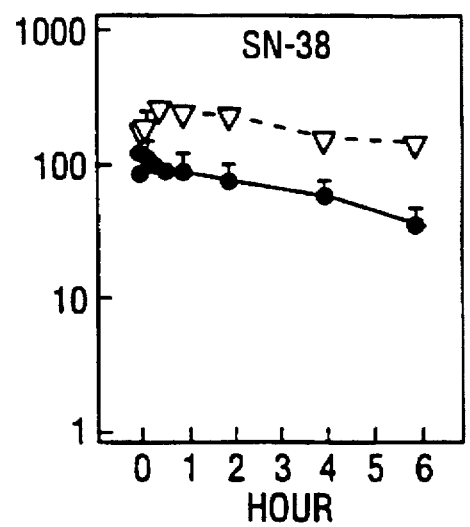
Figure 6C:
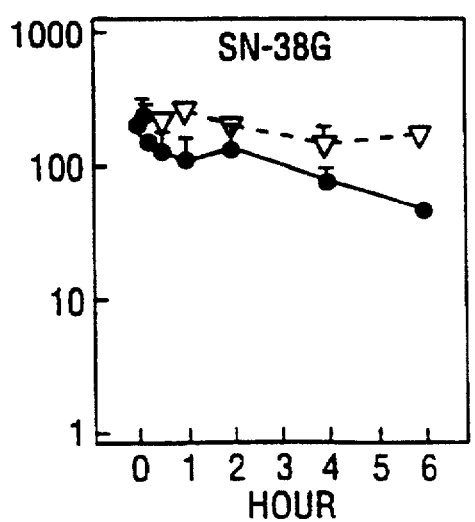

FIG. 6A, FIG. 6B and FIG. 6C. Plasma concentrations of CPT-11 (FIG. 6A), SN-38 (FIG. 6B) and SN-38G (FIG. 6C) following 20 mg/kg CPT-11 (control, n=4). The pretreated group (n=3) received 60 mg/kg cyclosporine A five minutes prior to the CPT-11 dose. Data is represented as mean+SD.

Figure 7A:
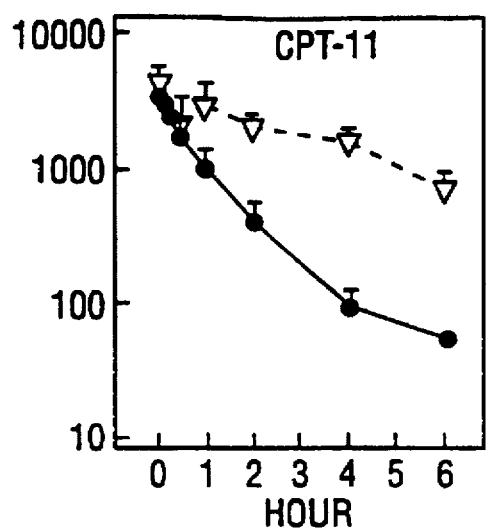
Figure 7B:
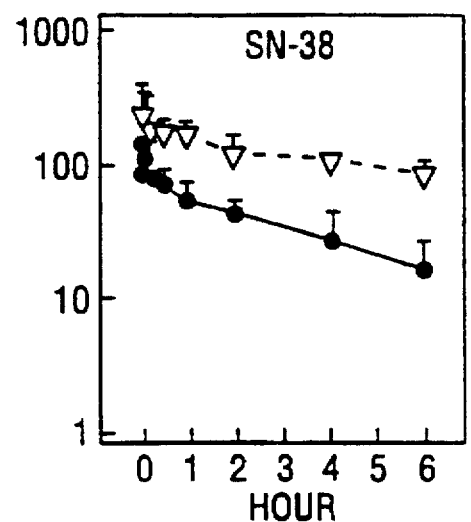
Figure 7C:
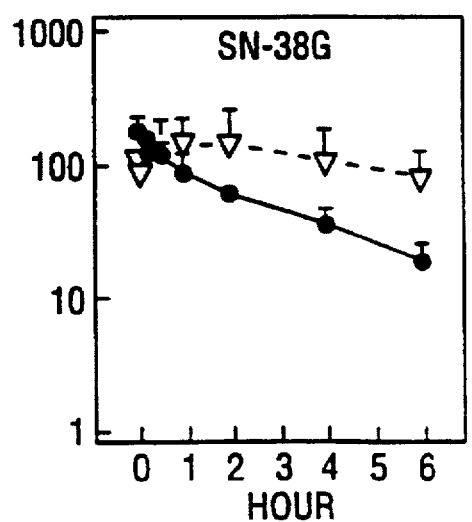

FIG. 7A, FIG. 7B and FIG. 7C. Plasma concentrations of CPT-11 (FIG. 7A), SN-38 (FIG. 7B) and SN-38G (FIG. 7C) following 10 mg/kg CPT-11 (control, n=3). The pretreated group (n=4) received 60 mg/kg cyclosporine A five minutes prior to the CPT-11 dose. Data is represented as mean+SD.

Figure 8A:
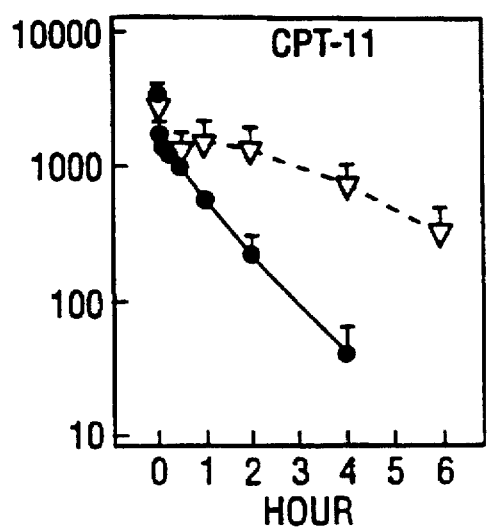
Figure 8B:
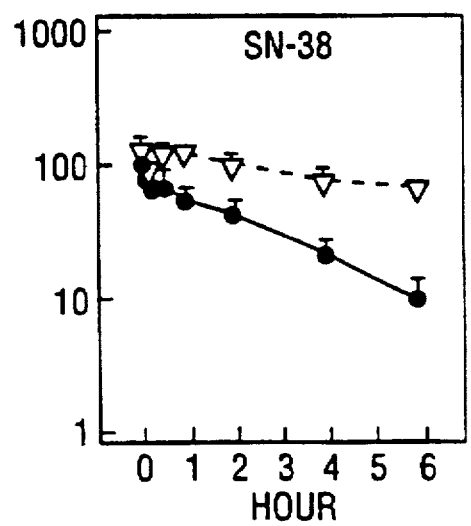
Figure 8C:
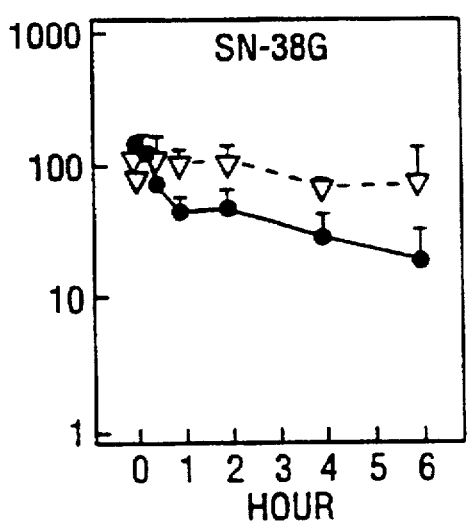

FIG. 8A, FIG. 8B and FIG. 8C. Plasma concentrations of CPT-11 (FIG. 8A), SN-38 (FIG. 8B) and SN-38G (FIG. 8C) following 6 mg/kg CPT-11 (control, n=3). The pretreated group (n=4) received 60 mg/kg cyclosporine A five minutes prior to the CPT-11 dose. Data is represented as mean+SD.

DETAILED DESCRIPTION OF THE PREFERRED EMBODIMENTS

Camptothecins constitute a group of anti-proliferative agents that possess the ability of inducing single strand breaks in chromosomal DNA and inhibiting nucleic acid synthesis. At concentrations of about 0.5 μM, camptothecin produces instantaneous and reversible nicks in the DNA in presence of the enzyme DNA topoisomerase 1, a novel target for cancer chemotherapy (Hsiang et al., 1985).

In normal cells, topoisomerase 1 produces relaxation of the supercoiled DNA by binding to a single strand of the nucleic acid to form a "cleavable complex" ('Arpa & Liu, 1989). Formation of the complex is followed by a break in the DNA strand thereby promoting passage of the unbroken strand. The break is then resealed by topoisomerase. Camptothecins block this resealing step by forming a ternary complex with the DNA and topoisomerase 1 resulting in an accumulation of cleavable complexes and inhibition of nucleic acid synthesis.

The cytotoxicity of camptothecins has been shown to be optimal at the S-phase compared to the $G_1$–$G_2$ phase suggesting that the single stranded breaks could be produced at replication forks which could trigger cell death (Horwitz & Horwitz, 1973; Li et al., 1972). The level of topoisomerase 1 activity has been reported to be elevated in tumor specimens making them selective targets for camptothecin activity (Giovanella et al., 1989).

CAMPTOTHECIN ANALOGUES

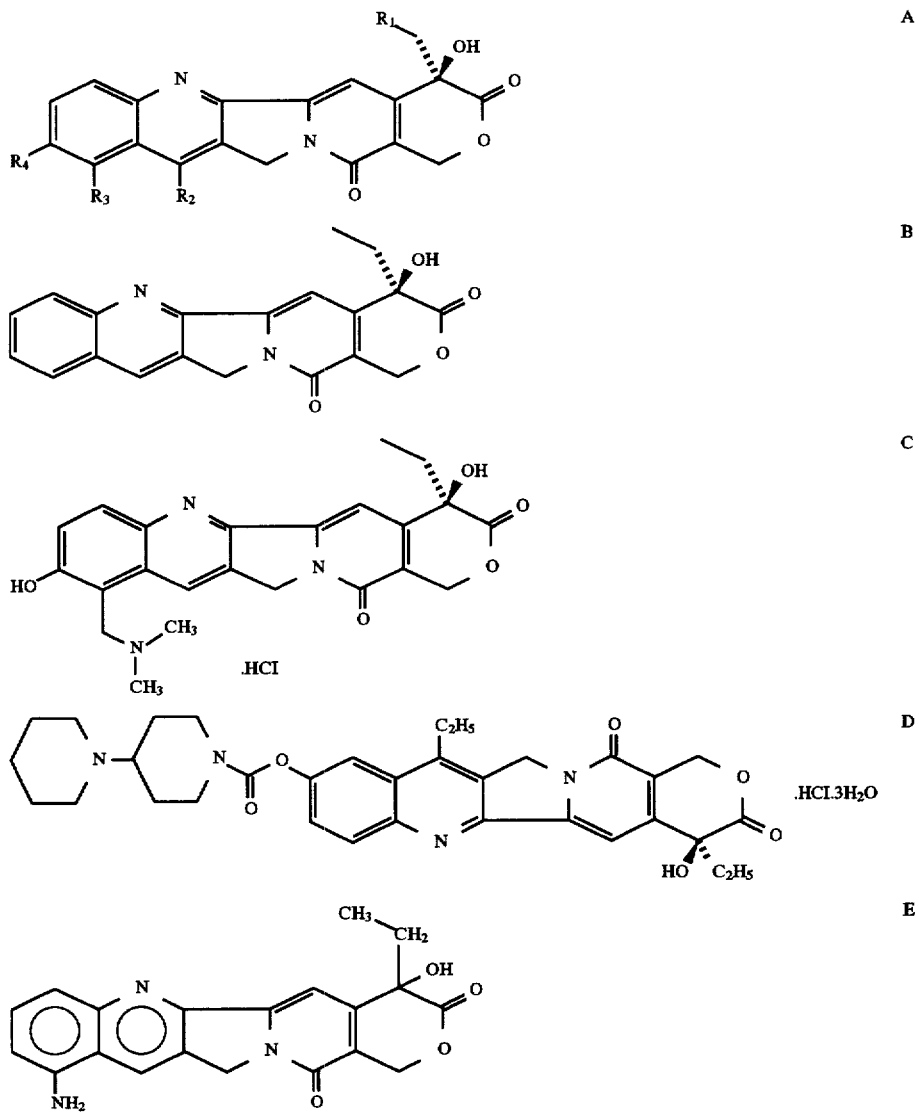

Camptothecin analogues are generally based upon the structure shown in A, to which various R groups may be added. Structure B is camptothecin itself; C is topotecan; D is CPT-11; and E is 9-amino-camptothecin (9-AC). The camptothecins of structures B through E are only exemplary forms of camptothecins that may be used in the present invention. Numerous other camptothecin analogues are available, as described by, e.g., Slichenmyer et al. (1994; 1993), Burris & Fields (1994) and Hawkins (1992).

Specific examples of active camptothecin analogues are 9-nitro-camptothecin (with a nitro group at position 9, rather than the amino group shown in structure E); GG211; seven-substituted water-soluble camptothecins (Emerson et al., 1995); hexacyclic camptothecin analogues (Sugimori et al., 1994); nine or ten-substituted camptothecins (Wani et al., 1987;1986;1980; Wall et al., 1993; Kingsbury et al., 1991); and E-ring-modified camptothecins (Ejima et al., 1992).

Emerson et al. (1995); Sugimori et al. (1994); Wall et al. (1993); Ejima et al. (1992); Wani et al. (1980; 1987; 1986); Kingsbury et al. (1991) and Sugasawa et al. (1976) each describe effective methodology for synthesizing camptothecin analogues. However, many are commercially available from different sources. For example, topotecan is generally supplied as the hydrochloride salt in a lyophilized mixture with mannitol (pH 3–4) or in gluconate buffer (pH 3.0).

Using an in vitro clonogenic assay, topotecan exhibited activity in breast, ovarian, non-small cell lung, colorectal, gastric and renal cell carcinomas (Burris et al., 1992). Activity was also noted in a panel of xenografts derived from ependymomas, gliomas and medulloblastomas in nude mice (Friedman et al., 1994). Responses in clinical trails have been noted in colorectal, small cell lung cancer, oesophageal, renal cell carcinoma, ovarian cancer and squamous cell cancer. 9-amino-20(s)-camptothecin (9-AC) is another camptothecinanalog that has demonstrated potent preclinical anti-cancer activity. Human xenografts studies have revealed significant activity of 9-AC against colon cancer. Clinical development of 9-AC is in progress.

Irinotecan (CPT-11) exhibited significant activity in a broad spectrum of in vitro and in vivo tumor models. It was effective in a wide variety of preclinical tumor xenografts including S180 and Meth A fibrosarcomas, Lewis lung, Ehrlich, and rat Walker 256 carcinomas, L1210 and P388 leukemias and pancreatic and mammary adenocarcinomas (Furuta et al., 1988; Tsuruo et al., 1988; Kawato et al., 1991). Activity against human tumor xenografts include colon and gastric adenocarcinomas, mammary carcinoma and squamous cell lung carcinoma 917. In clinical studies responses have been reported in mainly metastatic colorectal cancer, non-small cell and small cell lung cancer as well as in breast, cervical, ovarian cancers, leukemias and lymphomas.

CPT-11 is converted in vivo to its active metabolite, SN-38, which is 600–1000 times more potent than the parent drug. Both CPT-11 and SN-38 occur as open and closed lactone forms after administration. However, only the closed lactone ring forms possess significant antitumor activity. The terminal half-life for the closed ring forms ranged from 5.4–6.1 hours for CPT-11 and 7.6–8.8 hours for SN-38. In animal studies, CPT-11 was found to be equally excreted into bile and urine while SN-38 was excreted primarily into bile.

Several Phase I studies of CPT-11 have already been conducted in Japan and Europe and at two centers in the United States. In these studies, CPT-11 has been administered as a 90 minute IV infusion on a variety of schedules including weekly ×4, alternating weeks×2, every 4 weeks, daily×5 q 4 weeks, BID×7 days q 4 weeks and daily×3 q week. CPT-11 has also been administered as a continuous infusion for 5 days every 4 weeks. In the Phase I studies, the DLT was found to be either myelosuppression or diarrhea. Other gastrointestinal toxicities such as nausea, vomiting and abdominal pain have also been observed. There have been inconsistent results regarding pharmacodynamic correlations between CPT-11 and/or SN-38 AUC and diarrhea and/or myelosuppression.

Based upon this information, the inventors initiated a Phase I study of CPT-11 administered as a 90 minute infusion weekly×4 in a six week cycle. They hypothesized that with G-CSF and optimal pharmacologic management of the diarrhea that a higher average dose (on that schedule) could be achieved.

A total of 25 patients have been treated since study activation (July 29, 1993) at CPT-11 doses ranging from 100–175 mg/m2. The detailed examples presented in the present application reflect treatment on 21 patients. The major toxicities have included myelosuppression, diarrhea, and abdominal cramping pain. Myelosuppression was not a significant toxicity at the first dose level (100 mg/m2), but was dose-limiting in one patient at the second dose level (120 mg/m2). At the third dose level (145 mg/m2) it was dose-limiting in two patients, but was ameliorated entirely by the subsequent use of prophylactic G-CSF.

Significant gastrointestinal toxicity was first manifested at the second dose level (120 mg/m2). Patients 4 (at 120 mg/m2) and 21 (at 145 mg/m2) had grade 3 abdominal cramping and received a dose reduction for cycle 2. Patient 15 (at 145 mg/m2) also had grade 3 abdominal cramping and declined a second cycle of CPT-11. Four other patients had mild (grade 1) abdominal cramps. Abdominal cramps did not necessarily correlate with diarrhea. Three patients developed small bowel obstructions while on study. Two of these cases were found at exploratory laparotomy to be due to progression of disease and one resolved after conservative therapy, but was likely due to progression of disease. The majority of the patients treated at doses >120 mg/m2 had grade 1–2 nausea and vomiting that was controlled with antiemetics. In a few patients, however, high doses of ondansetron were required to achieve relief.

Patients 13 and 16, treated at 145 mg/m2, were hospitalized with neutropenic fevers during weeks 4 and 3, respectively of cycle 1. Beginning with patient 17, all patients received G-CSF for 5 days following each dose of CPT-11. No cases of neutropenia>grade 1 were observed at 145 mg/m2 following this intervention. However, the first two patients treated at 175 mg/m2 were hospitalized with neutropenic fevers despite prophylactic G-CSF.

Four separate HPLC assays are being utilized in this study. They measure open and closed CPT-11, open and closed SN-38, total CPT-11 and SN-38, and SN-38 glucuronide. In addition to plasma concentrations, the inventors are collecting urine for the first 24 hours after the first dose.

Fresh plasma transported on ice is immediately analyzed for open vs. closed (lactone ring) CPT-11 and SN-38 by a modification of the method of Rothenberg et al. (1993). Samples are prepared from 250 μL of plasma. The proteins are precipitated by adding 500 μL of cold methanol (−200C.) followed by centrifugation. For open versus closed CPT-11 analysis, a dilution of 150 μL of the supernatant is made with 150 μL of 0.1M sodium dihydrogen phosphate with 3 mM heptanesulphonate (pH 4). Injections of 50 μL are made onto a μBondapak C18 Guard Pak and μBondapak C18 column, 3.9×300 mm, 10 μ. The open and closed forms are separated using 65:35 methanol:0.1M sodium dihydrogen phosphate with 3 mM heptanesulphonate (pH 4) at a flow rate of 0.8 mL/min and detected by fluorescence (using excitation and emission wavelengths of 380 and 430 nm, respectively). For the analysis of open versus closed SN-38, 150 μL of the supernatant are diluted with 150 μL of deionized water and 200 μL are injected onto a Novapak C18 Guard Pak and a Novapak C18 column, 3.9×150 mm, 4 μ. The open and closed forms are separated using 1:3 acetonitrile:deionized water (pH 6.2) at a flow rate of 0.8 mL/min and detected by fluorescence (using excitation and emission wavelengths of 375 and 566 nm, respectively).

Although only the lactone forms have pharmacologic activity, the conversion between the open hydroxyacid and closed lactone forms is reversible. Thus, this is analogous to separately measuring free and bound drug for agents with significant protein-binding. If the ratio of active (closed lactone or free unbound) to total drug is relatively constant, there is relatively little advantage to measuring both active and inactive species, as opposed to total drug. Since for CPT-11 and SN-38, such assays are quite labor-intensive, the inventors have amended their study to only perform such detailed assays on a small subset of specimens, selected timepoints on the first patient at each dose level. The inventors have also demonstrated that for any individual specimen, the ratio of closed to total drug is highly dependent on exact pH titration, and thus may be unreliable.

The inventors assayed for total CPT-11 and SN-38 using standard intensive sampling, applying a modification of the assay of Chabot et al. (1992). A liquid-liquid extraction is used, as described above. CPT-11 and SN-38 are extracted using cold methanol (2 mL) and evaporated to dryness under nitrogen. The residue is reconstituted with 250 μL of methanol containing 1% iON HCl and injected onto a gBondapak C18 Guard Pak and a μBondapak C18 column, 3.9×300 mm, 10μ with detection by fluorescence (using excitation and emission wavelengths of 375 nm and 566 nm, respectively).

Previous investigators have not characterized the pharmacokinetics of SN-38 glucuronide. The present inventors thought this to be of great importance because this pathway represents the major detoxification route for the active metabolite SN-38, and findings of significant interindividual differences in glucuronidation of SN-38 would thus be of clinical significance. Furthermore, SN-38 excreted into the bile may still have significant pharmacologic toxicity, and thus the inventors hypothesized that interindividual differences in biliary SN-38 excretion would be correlated with susceptibility to the diarrhea occurring with this therapy. SN-38 glucuronide is being assayed by incubating plasma samples with β-glucuronidase prior to SN-38 analysis. This then represents the sum of SN-38 and SN-38 glucuronide, and the latter can be determined by subtracting the SN-38 concentration without such incubation. There was wide variability in the degree of glucuronidation as manifested by the ratio of the AUCs of SN-38 to SN-38 glucuronide, ranging from 0.12 to 2.53. Since virtually all of the SN-38 that is not glucuronidated is eliminated by biliary excretion, the inventors hypothesized that the ratio of SN-38 to SN-38 glucuronide would be an important parameter. To control for interindividual variability in the amount of available drug, this ratio was multiplied by the CPT-11 AUC to obtain this "biliary index".

The results to date allowed classification of patients according to Grade 0–2 diarrhea (n=12) and Grade 3–4 (n=9) diarrhea. The most important pharmacokinetic parameter appears to be the "biliary index" (P<0.0004), derived from the CPT-11, SN-38, and SN-38 glucuronide AUCs. Using only the ten patients treated at a uniform dose of 145 mg/m2, the "biliary index" was the only significant variable, with median values of 2275 and 4747 in five patients each with Grade 0–2 and 3–4 diarrhea (P=0.03).

Since glucuronidation appears to be polymorphic and potentially typeable, the present inventors propose that the development of CPT-11 may be similar to that used for amonafide. The first step will be to extend the present studies showing that patients that are "poor glucuronidators" are at higher risk of CPT-11 induced diarrhea. In conjunction with these studies, the inventors will correlate SN-38 glucuronidation with a glucuronidation probe. Acetaminophen, which undergoes an ether glucuronidation, as occurs for SN-38, has been used by other investigators (DeMorais et al., 1992). If this were shown to be a predictive test, then the RPTD could be determined separately for these two populations, as previously performed for amonafide. Since recent data suggests that blacks may have a higher incidence of "poor glucuronidators" (Hecht et al., 1994), it will be especially important to evaluate interracial differences in CPT-11 toxicity. Again, the inventors have previously demonstrated that minority patients are at greater risk for amonafide toxicity. Because of the potential intergender and interracial differences in glucuronidation, the inventors will carefully evaluate specific racial and gender subsets.

The inventors propose that a correlation between glucuronidator status and CPT-11 toxicity exists and that it is thus very important to induce this phase II enzyme. Induction of phase II enzymes has been of major interest to investigators working in the chemoprevention field, because of the importance of these enzymes in carcinogen detoxification. One agent under investigation as an inducer of these enzyme systems is oltipraz, a dithiolthione. Oltipraz has been demonstrated to be an inducer of GST and UDP-glucuronosyltransferase, and reduces acetaminophen toxicity in a rodent model (Egner et al., 1994). Therefore oltipraz is considered as a potential agent with which to induce glucuronidation prior to CPT-11 treatment, and monitored with acetaminophen phenotyping. Such a strategy is contemplated to significantly enhance the therapeutic index of CPT-11.

Figure 1:
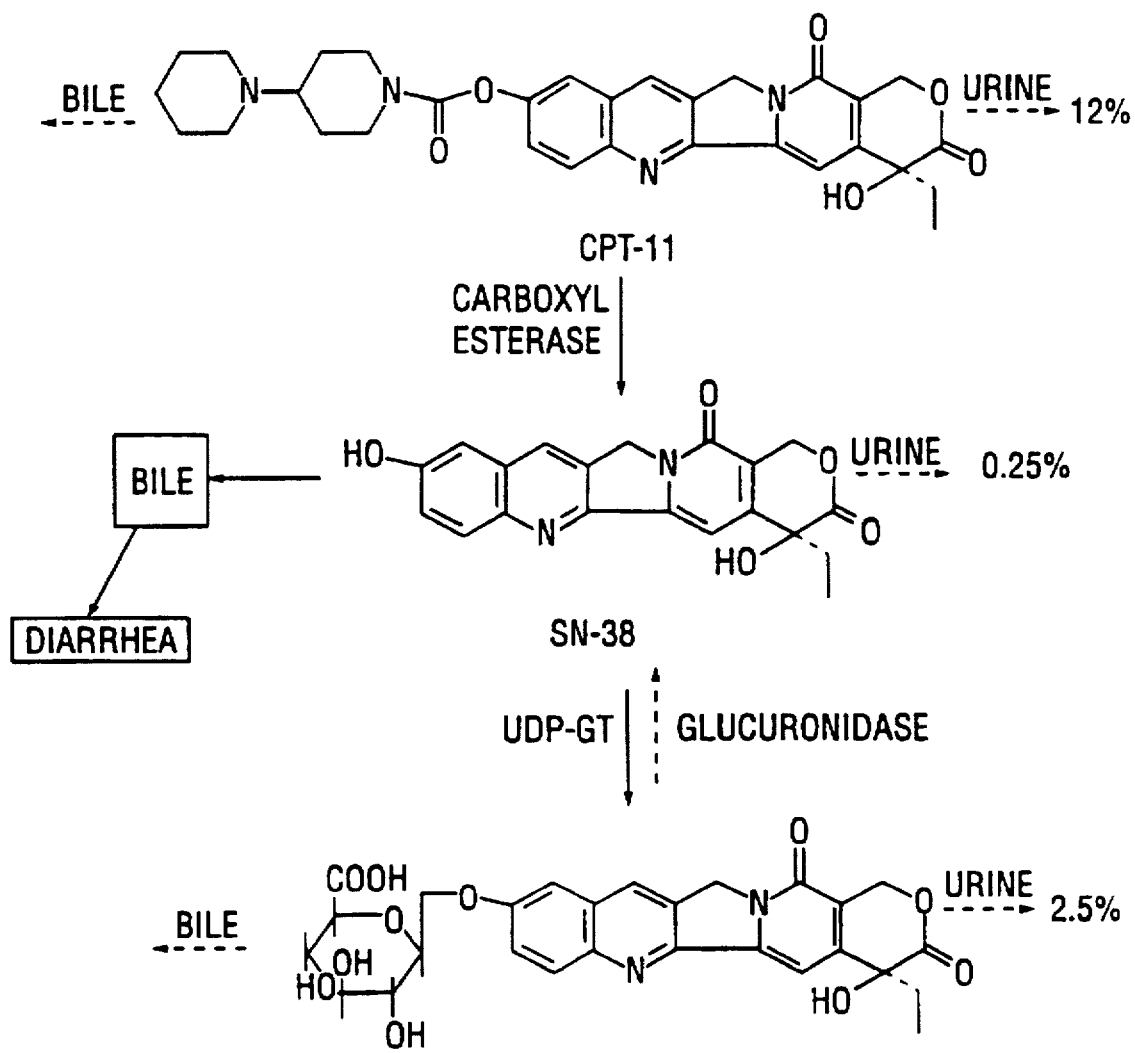
FIG. 1. Metabolic pathways of SN-38 excretion showing beneficial and toxic excretion pathways.

Since gastrointestinal toxicity was related to excessive amounts of SN-38 in the bile that drained into the gut, the inventors realized that another approach to reduce toxicity of camptothecins, such as CPT-11, would be to reduce transport into the bile (FIG. 1). The inventors thus planned a study to identify the biliary component responsible for the camptothecin transport activity. It was reasoned that the p-glycoprotein transporter was one candidate. The p-glycoprotein is located in the canalicular membrane of hepatocytes and is believed to be involved in the biliary transport of several compounds. The inventors determined that both CPT-11 and SN-38 did interact with the p-glycoprotein.

The inventors thus reasoned that p-glycoprotein inhibitors would be useful agents for administration in combination with camptothecins. Using animal studies, it was found that both high and low doses of cyclosporine A (cyc A) increased the systemic availability of CPT-11, indicating a reduction or inhibition of biliary excretion. Therefore pretreatment with p-glycoprotein inhibitors, such as cyclosporine A, is proposed to be a useful means of decreasing toxicity and plasma clearance of CPT-11 and improving the bioavailability of SN-38.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Patient Selection and Treatment Plan

Patients with solid tumors or lymphoma were eligible for treatment if they were refractory to standard treatment or if no effective standard treatment existed. All patients had either measurable or evaluable disease, were at least 18 years of age, with a Karnofsky's performance status of at least 70% and had a life expectancy of at least 3 months. All patients met the standard laboratory criteria including criteria for adequate organ function. Informed, written consent was obtained from all patients prior to their first dose of CPT-11. The drug was given in 500 cc normal saline by intravenous infusion over 90 minutes on a weekly basis for four doses in a sixweek cycle. Weekly dosing was assigned by a standard phase I design using the following dose levels: 1) 100 mg/m$^2$, 2) 120 mg/m$^2$, 3) 145 mg/m$^2$, and 4) 175 mg/m$^2$. Following the first dose, blood and urine sampling was performed for the first 24 hr after the infusion for pharmacokinetic evaluations. A second cycle was given with the same dose and schedule used during cycle 1. If dose limiting toxicity was observed during cycle 1, patients were treated at the previous dose level for all subsequent cycles. Patients who experienced dose limiting neutropenia were eligible to receive G-CSF at 5 µg/kg/day according to the criteria defined below.

EXAMPLE 2

Toxicity Evaluation

Toxicity assessment was done according to the CALGB expanded toxicity criteria. Patients who experienced>grade 2 diarrhea at any time while on study were begun on loperamide 4 mg p.o. followed by 2 mg p.o. after every stool up to a total dose of 16 mg/day. If loperamide was unsuccessful in controlling diarrhea, patients were begun on octreotide acetate 100–600 µg for 2–3 doses per day. Stool collections were also obtained to test for any co-existing infection. CPT-11 doses were held until diarrhea resolved<grade 2.

EXAMPLE 3

Sample Analysis

To determine drug and metabolite levels, heparinized blood samples obtained on the first cycle of therapy, were centrifuged and the plasma was stored at −70° C. until analysis. CPT (camptothecin, 1 µg/ml, obtained from the National Cancer Institute, Bethesda, Md.) was used as an internal standard. One hundred µl of plasma was extracted with 2 ml of methanol, centrifuged at 2500×g for 10 min and the supernatant was evaporated to dryness. Reconstitution was done with 200 µl of methanol containing 0.1% 10M HCL (pH~2.0). For the estimation of SN-38G, plasma samples were extracted as described above. Prior to reconstitution, the samples were incubated with 1000 U of glucuronidase (Sigma Chemical Co., St. Louis, Mo.) for 2 hours at 37° C.

The total CPT-11 and SN-38 concentrations in the plasma were estimated by modification of the HPLC method of Barilero et al. (Barilero et al., 1992). Analysis was done using a $C_{18}$ column (µBondapak, 10 µm, 3.9×300 mm; Waters Associates, Milford, Mass.) preceded by a Novapak $C_{18}$ guard column. The mobile phase was a mixture of 35% acetonitrile: 65% 0.1M potassium dihydrogen phosphate containing 3 mM sodium heptane sulphonate (pH 4.0). Detection was monitored by a Hitachi F1050 Fluorescence detector (Hitachi Instruments Inc., Naperville, Ill.) with a $\lambda$ex at 375 nm and $\lambda$em at 566 nm. Standard curves of CPT-11 (obtained from Yakult Honsha Co. Ltd., Tokyo, Japan) and SN-38 (obtained from Yakult Honsha Co. Ltd.) were linear within the range of 5.0–2365.3 ng/ml (r=0.99) and 9.8–116.5 ng/ml (r=0.99), respectively. SN-38G concentrations were determined as the increase in SN-38 concentrations following incubation with glucuronidase.

EXAMPLE 4

Data Analysis

The plasma concentration-time data of CPT-11, SN-38 and SN-38G were analyzed by non-compartmental analysis using PCNONLIN (SCI, Lexington, Ky.). The area under the plasma concentration-time curve (AUC) from time zero (predose) to the time of the last quantifiable concentration ($AUC_t$) was calculated by the trapezoidal rule. The AUC extrapolated to time infinity ($AUC_{t\rightarrow\infty}$) was estimated by dividing the last quantifiable concentration by the terminal rate constant obtained by the log-linear regression of the terminal elimination phase. The AUC was the summation of $AUC_t$ and $AUC_{t\rightarrow\infty}$. Clearance (CL) was estimated as the ratio of the dose and AUC.

Since CPT-11 induced diarrhea in nude mice was associated with intestinal accumulation of SN-38 (Araki et al., 1993), biliary concentrations of the metabolite might be predictive of gastrointestinal toxicity. The principle of area analysis has been used for assessing the disposition of biotransformed drugs (Kaplan et al., 1973). The present study employed this principle to obtain an estimate of SN-38 excreted in the bile. Since glucuronidation is the major pathway of elimination of SN-38, the fraction of SN-38 not conjugated would be primarily excreted in the bile. The net biliary concentration of SN-38 would then be a resultant of its formation and elimination. This concentration was expressed as the "biliary ratio" which was the ratio of AUC of SN-38 to SN-38G. To control for individual variability in the amount of available drug, the ratio was multiplied by the AUC of CPT-11 to obtain a "biliary index" of SN-38. This was expressed as:

$$AUC_{CPT-11} \times \frac{AUC_{SN-38}}{AUC_{SN-38G}}$$

A patient with a low rate of glucuronidation would have relatively higher concentrations of SN-38 in the bile draining into the gut, and would be at a higher risk of gastrointestinal toxicity. Also, patients receiving high doses of CPT-11, may have saturation of the glucuronidation pathway, leading to elevated biliary SN-38 concentrations. Overall, the higher the "biliary index" of a patient, the greater would be the risk of diarrhea.

The nonparametric Mann-Whitney test was employed to test for differences in pharmacokinetic outcomes between two patient groups, defined by the worst severity of diarrhea experienced in the first two cycles of CPT-11 treatment. Statistical tests were performed in the Number Cruncher Statistical System (Dr. Jerry Hintz, Kaysville, Utah). A two-sided significance level of less than or equal to 0.05 was considered statistically significant.

EXAMPLE 5

Metabolism of CPT-11

Figure 2A:
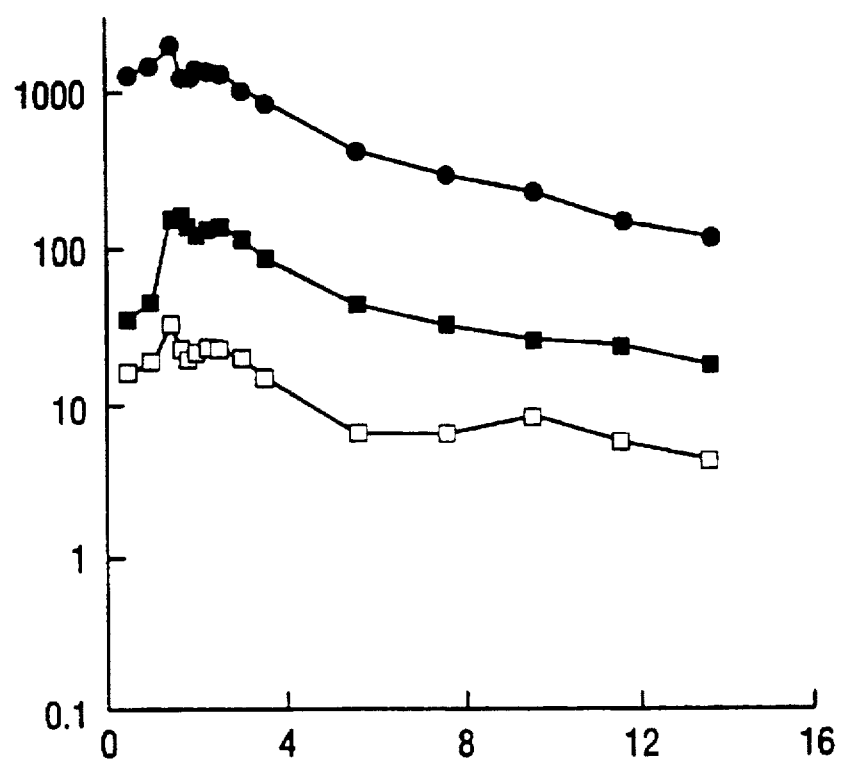
FIG. 2A and FIG. 2B. Plasma disposition curves for CPT-11 (●), SN-38 (□) and SN-38G (■) following intravenous infusion of CPT-11.
Figure 2B:
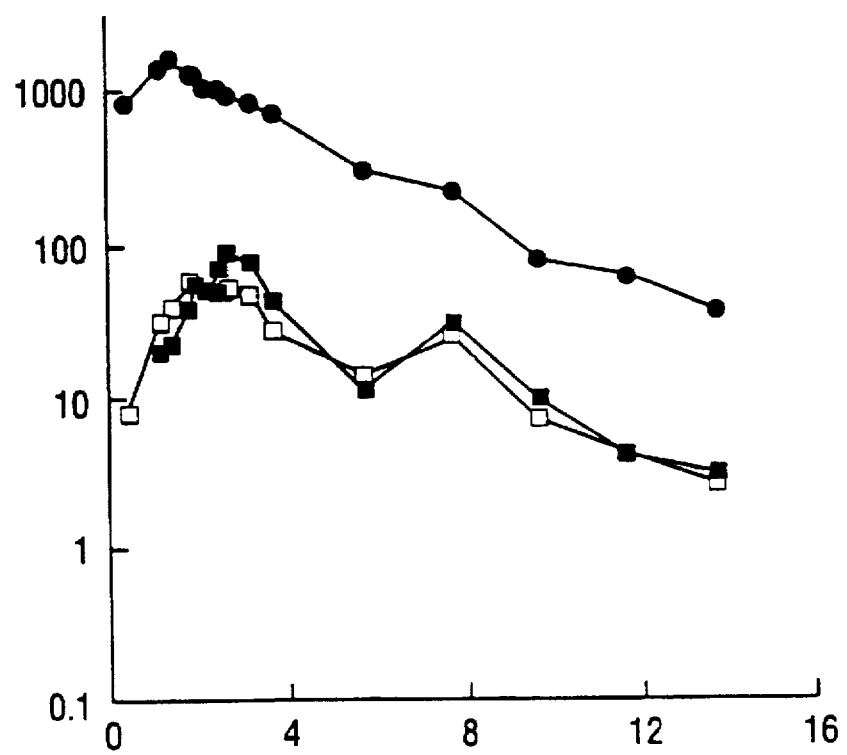

Following intravenous infusion of CPT-11, two metabolites could be detected in the plasma: SN-38 and the SN-38G. The glucuronide was the major metabolite, with peak plasma concentrations occurring 0.5 to 3 h after SN-38 peak and plasma levels generally exceeding that of SN-38 (FIG. 2A). In addition, a prominent secondary peak was observed in the SN-38 profile (FIG. 2B). These observations were in agreement with preclinical studies in rats that reported 55%, 22% and 9% of the biliary radioactivity excreted over 24 h was unchanged CPT-11, SN-38G and SN-38 and approximately 18% of the biliary radioactivity was reabsorbed from the intestine (Atsumi et al., 1991). Pharmacokinetic estimations of the drug and metabolites in the four dose levels are listed in Table 1. There was no effect of pretreatment with G-CSF on the pharmacokinetics of CPT-11 and its metabolites. A nonlinear 2.6 fold increase of AUC of CPT-11 from the 100 mg/m$^2$ to the 175 mg/m$^2$ dose level correlated to the decrease in CL estimates and was in accordance with previous reports of nonlinear pharmacokinetics of CPT-11 (Kaneda et al., 1990; Negoro et al., 1991; Kaneda & Yokokura, 1990). However, there was also a 3.7 and 2.7 fold increase in the AUC estimations of SN-38 and SN-38G, respectively over the 1.75 fold dose range. Interestingly, there appeared to be no increase in the SN-38G AUC between the 145 mg/m$^2$ and the 175 mg/m$^2$ dose levels. The nonlinear increase in CPT-11 AUC seen in the present study could be due to progressive saturation of both the non-metabolic and metabolic pathways of elimination of CPT-11. The plateau concentrations of SN-38G at the two highest dose levels indicate saturation of glucuronidation of SN-38 to SN-38G. The increase in the SN-38 AUC irrespective of decreasing CL of CPT-11 could be due to the capacity limitation of the glucuronidation pathway of SN-38. The secondary peak in the plasma profile contributing to about a 12% increase in the $AUC_{SN-38}$ is suggestive of hydrolysis of SN-38G by glucuronidase resulting in enterohepatic circulation of SN-38.

TABLE 1

Pharmacokinetic estimates of CPT-11, SN-38 and SN-389 by dose level. Data are represented as mean ± SD.

| Dose Level | $AUC_{CPT-11}$ ng.h/ml | $AUC_{SN-38}$ ng.h/ml | $AUC_{SN-389}$ ng.h/ml | CPT-11-CL liter/h/m² |
|---|---|---|---|---|
| 100 mg/m² n = 3 | 5603 ± 967 | 102.4 ± 28 | 399.4 ± 344 | 20.31 ± 4.37 |
| 120 mg/m² n = 6 | 5031 ± 1111 | 127.4 ± 45 | 266.9 ± 233 | 24.93 ± 5.98 |
| 145 mg/m² n-10 | 11972 ± 6790 | 271.2 ± 119 | 1152 ± 1199 | 13.91 ± 5.98 |
| 175 mg/m² n = 2 | 14543 ± 5220 | 376.1 ± 6.29 | 1058 ± 622 | 12.86 ± 4.62 |

TABLE 2

Correlation of pharmacokinetic estimate to CPT-11 induced diarrhea. Patients receiving a dose of 145 mg/m² were classified according to the worst grade of diarrhea in treatment cycle 1 or 2. Values are represented as median values with the range in parentheses.

| Pharmacokinetic Estimate | Grade 0–2 n = 5 | Grade 3–4 n = 5 | p-Value |
|---|---|---|---|
| $AUC_{CPT-11}$ ng.h/ml | 9160 (8391–17918) | 14879 (5291–23392) | 0.75 |
| $AUC_{SN-38}$ ng.h/ml | 211.5 (170.0–282.5) | 269.1 (161.8–544.4) | 0.35 |
| $AUC_{SN-38G}$ ng.h/ml | 889.9 (413.1–2135) | 762.3 (242.4–4206) | 0.46 |
| "Biliary ratio" | 0.27 (0.12–0.41) | 0.53 (0.13–0.87) | 0.25 |
| "Biliary index" ng.h/ml | 2276 (1812–3812) | 4747 (3028–7856) | 0.03 |

EXAMPLE 6

Inter-patient Variability in Disposition

Across dose levels there was a 17% to 57% variability in the $AUC_{CPT-11}$ and 2% to 44% variability in the $AUC_{SN-38}$ estimates as measured by the percent coefficient of variation. It has been suggested that variability in CPT-11 disposition was due to interpatient differences in carboxyl esterase levels (Negoro et al., 1991; Ohe et al., 1992; Rothenberg et al., 1993; Rowinsky et al., 1994). However, estimation of carboxyl esterase activity in predose plasma samples of patients in this study showed poor correlation to dose normalized AUC of SN-38 or summation of SN-38 and SN-38G (Gupta et al., 1994a). This indicated that formation from CPT-11 was not the rate determining step in the disposition of SN-38. Moreover, on average 0.25% and 3% of the dose was excreted in the urine as SN-38 and SN-38G, respectively. Hence, renal clearance is a minor route of elimination with the major fraction of SN-38 undergoing conjugation and elimination in the bile, an observation consistent with previous preclinical reports (Atsumi et al., 1991; Kaneda et al., 1990; Kaneda & Yokokura, 1990). The interpatient variability (coefficient of variation) in $AUC_{SN-38G}$ across the 4 dose levels ranged from 59% to 104%. Therefore, individual differences as well as dose dependency of the SN-38 glucuronidation pathway may be significant and have a major influence on SN-38 disposition. The influence of interpatient variability was reflected in the "biliary ratio" estimates which ranged from 0.15 to 2.53.

EXAMPLE 7

Correlation of Diarrhea with Glucuronidation

Figure 3:
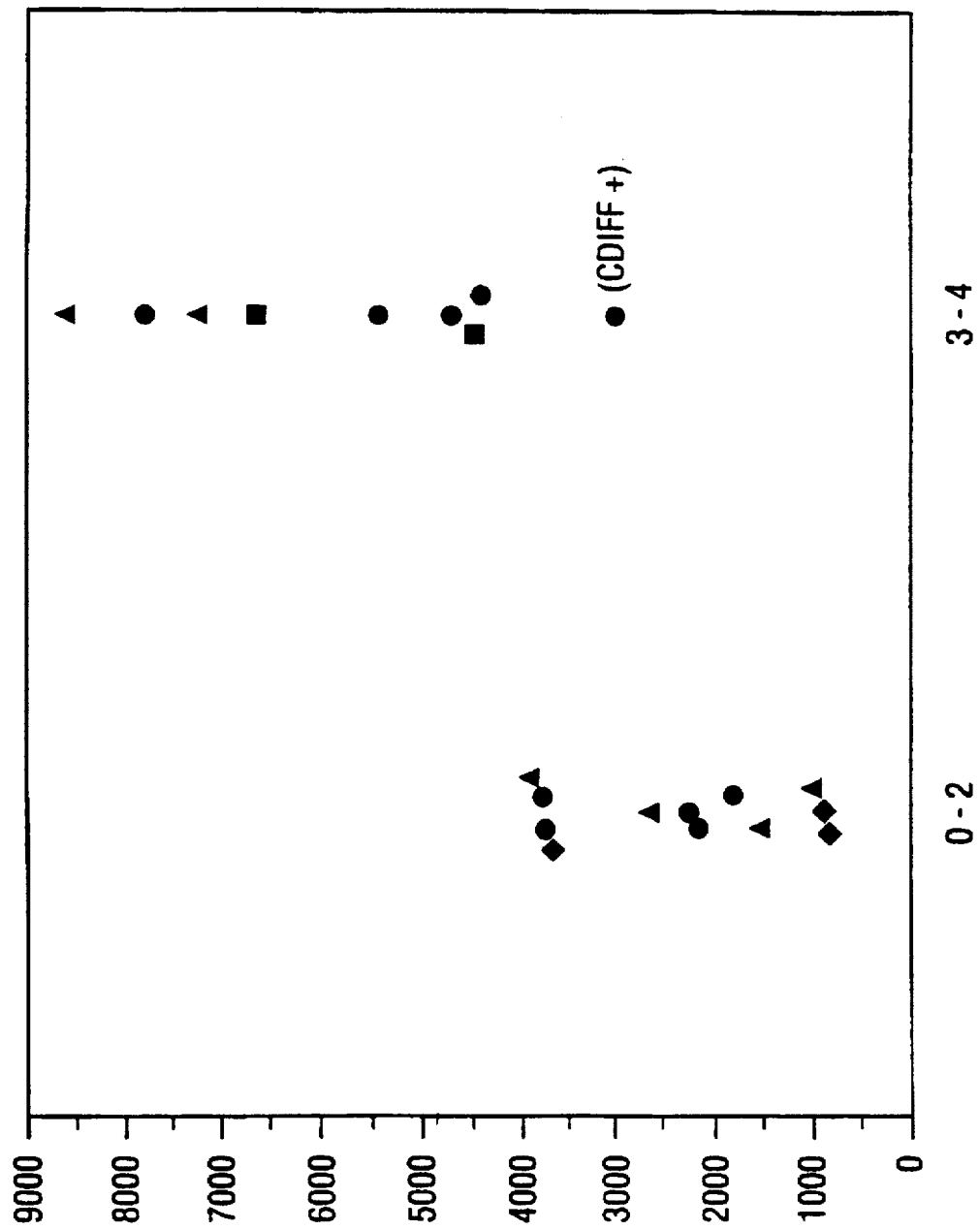
FIG. 3. Scatterplots of "biliary index" as a function of diarrhea grade. Data from dose levels 100 mg/m2 (♦), 120 mg/m2 (▲), 145 mg/m2 (●) and 175 mg/m2 (■) are shown.

No diarrhea was observed at the lowest dose level of 100 mg/m². There appeared to be a dose dependent increase in this toxicity with 34%, 50% and 100% patients developing grade 3–4 diarrhea in the 120 mg/m², 145 mg/m², and 175 mg/m² dose levels, respectively. Comparisons of median values of $AUC_{CPT-11}$, $AUC_{SN-38}$ and $AUC_{SN-38}g$ and "biliary ratios" between the grade 0–2 and grade 3–4 groups in the 145 mg/m² dose level showed no significant differences (Table 2). The only significant variable was the "biliary index" with median values of 2276 and 4747 for the grade 0–2 and grade 3–4 groups, respectively (p=0.03). There was also a significant correlation between "biliary index" and severity of diarrhea based on all dose levels (p=0.0004, FIG. 3). There was an obvious division of patients based on this index, with about 90% of the patients with grade 3–4 diarrhea having index estimates above 4000. In 4 of 5 patients with grade 3–4 diarrhea in the 145 mg/m² dose level, the "biliary index" was >4000. The fifth patient had an index of 3028 but had a positive stool culture for *Clostridium difficile* toxin (indicated by c diff+) which likely contributed to the severity of diarrhea. Hence, in agreement with the inventors' hypothesis, with respect to the total CPT-11 available to the systemic circulation, patients with relatively low glucuronidation rates had progressive accumulation of SN-38 leading to toxicity. The hypothesis was supported by the fact that urinary estimates of the SN-38G were on average 2.5 fold lower in patients with grade 3–4 diarrhea.

Pharmacogenetic variations in drug metabolism have contributed to treatment-related toxicities of several anti-cancer drugs (Lennard et al., 1989; Harris et al., 1991; Ratain et al., 1991). In the case of CPT-11, variability in glucuronidation, which may be genetic, was primarily responsible for differential accumulation of SN-38 in the gut. Since glucuronidation represents the major detoxification pathway of SN-38, patients deficient in this enzyme activity should have a greater susceptibility to diarrhea. Interindividual differences coupled with inter-racial differences in glucuronidation have been reported (Patel et al., 1992). Deficient as well as capacity limited glucuronosyl transferase activity has been shown to be responsible for the toxicity of drugs such as acetaminophen (De Morais & Wells, 1989; Hjelle, 1986). Therefore, one approach to increasing the therapeutic index of CPT-11 would be to induce glucuronosyl transferase activity.

EXAMPLE 8

CPT-11 and Phenobarbital Administration

The isoforms of UDP-GT can be broadly classified based on differential induction by phenobarbital and 3-methylcholanthrene (Burchell & Coughtrie, 1989). Of these 2 types of inducers, phenobarbital has been used as an anticholinergic/antispasmodic and a mildly sedative agent in humans. The inventors' objective here was to investigate the effect of phenobarbital administration on the glucuronidation of SN-38 in rats.

A. Materials and Methods

Materials: CPT-11 solution was obtained from the Yakult Honsha Co., Tokyo, Japan, phenobarbital was obtained from Elkins-Sinn Inc., Cherry Hill, N.J. All other chemicals were of analytical grade and were obtained from Fisher Scientific Co., Itasca, Ill.

Animal protocol: Female Wistar rats (~200 gm) having a permanent catheter installed in the right jugular vein were obtained from Charles River Breeding Laboratories (Wilmington, Mass.). The rats were maintained in metabolism cages for at least 24 hours prior to the studies, and food and water were supplied ad libitum.

The induction studies were designed according to that reported by Bock et al. (1979). Three rats were given a single intraperitoneal dose of 100 mg/kg phenobarbital in physiological saline followed by 0.1% (w/v) phenobarbital in drinking water for four days. On day 5, CPT-11 (20 mg/kg) was administered through the jugular catheter and blood samples were withdrawn and analyzed as described later. The control animals received a single dose of CPT-11 (20 mg/kg) only.

Serial blood samples (200 µl) were withdrawn through the catheter at 3, 5, 10, 15, 30, 60, 120, 240 and 260 minutes following CPT-11 administration. After each sample the catheter was flushed with an equal volume of physiologic saline. The samples were immediately centrifuged at 2500×g for 10 minutes and the plasma obtained was stored at −70° C. until analysis. CPT-11, SN-38 and SN-38G in 10-20 µl plasma samples were quantitated by a the reversed-phase HPLC method as previously described (Gupta et al., 1994b).

Data Analysis: The plasma concentration-time profile of the control and pretreated groups of rats were analyzed using non-compartmental methods (PCNONLIN, SCI, Lexington, Ky.). The systemic exposure of CPT-11 and metabolites was estimated as the area under the concentration-time curve from time 0 to 6 hours (AUC). The nonparametric Mann-Whitney test was used to test for differences in AUC between the control and pretreated groups.

B. Results

Only two rats of the three that received phenobarbital were evaluated due to failure of the jugular catheter in one rat. Phenobarbital was successful in inducing SN-38 UDP-GT activity as observed by the 173% increase in the AUC of the induced animals compared to the controls (Table 3, FIG. 4C). On the other hand, the AUC of both CPT-11 and SN-38 indicated a 60% and 50% decline. The decline in CPT-11 concentrations was possibly due to enhanced deesterification of CPT-11 to SN-38. The resultant pool of SN-38 however, was insufficient to compensate for the increased substrate requirement by the induced UDP-GT which therefore resulted in a 50% decline in the AUC of SN-38. The overall decline in the AUC of both CPT-11 and SN-38 was indicative of increased conjugation of SN-38 by UDP-GT.

TABLE 3

EFFECT OF INDUCTION OF UDP-GT ACTIVITY

| GROUP | $AUC_{CPT-11}$ ng.hr/ml | $AUC_{SN-38}$ ng.hr/ml | $AUC_{SN-38G}$ ng.hr/ml |
|---|---|---|---|
| CPT-11: 20 mg/kg Phenobarbital: 75 mg/kg/d for 3 days (FIG. 4A, FIG. 4B, FIG. 4C) | | | |
| Control (n = 4) | 7695.8 ± 2674 | 364.89 ± 44.19 | 556.52 ± 167.03 |

TABLE 3-continued

EFFECT OF INDUCTION OF UDP-GT ACTIVITY

| GROUP | $AUC_{CPT-11}$ ng.hr/ml | $AUC_{SN-38}$ ng.hr/ml | $AUC_{SN-38G}$ ng.hr/ml |
|---|---|---|---|
| Pretreated (n = 2) | 3055.8 | 182.07 | 1521.7 |
| Change | −60.29% | −50.1% | 173% |

Effect of pretreatment with phenobarbital on the disposition of CPT-11. Control rats were given a single bolus dose of 20 mg/kg CPT-11. Pretreated rats received a single intraperitoneal administration of phenobarbital (100 mg/kg) and 0.1% (w/v) phenobarbital in drinking water for 4 consecutive days. On day 5 the pretreated rats were given a single bolus dose of 20 mg/kg CPT-11. Data is represented as mean ± SD for the control group and mean for the pretreated group.

Glucuronidation of SN-38 by UDP-GT represents a detoxification pathway and induction of this excretory pathway would prove to be beneficial in lowering incidences of dose limiting diarrhea attributed to SN-38. Conversely, biliary excretion of SN-38 results in accumulation of SN-38 in the gut leading to diarrhea and thus constitutes an undesirable route of excretion. UDP-GT induction by phenobarbital resulted in a 2.7 fold increase in the SN-38G concentration in conjunction with about a 2 fold decrease in the CPT-11 and SN-38 availability. This would result in a substantially lower concentration of SN-38 draining into the gut.

It is proposed that phenobarbital would be given at a dose of 60 mg/kg a day, every day of therapy.

In the present, and all the following examples, the dosage regimens suggested are provided as starting points for doses of second agents that increase conjugative enzyme activity. The doses described may be considered for therapeutic use in combination with CPT-11, however, such doses are not intended to be optimum values, but to provide a range that can be readily optimized by a physician in the normal course of events. The toxic and lethal doses are often quoted for further guidance and should, of course, be avoided.

EXAMPLE 9

Oltipraz

Oltipraz (RP-35972; 4-methyl-5(2-pyrazinyl)-3H-1,2-dithiole-3-thione; available from Rhone-Poulenc) is one agent that is preferred for use with the present invention. It has been shown to exert chemoprotective effects of against carbon tetrachloride and acetaminophen toxicity (Ansher et al., 1983; Davies & Schnell, 1991; Egner et al., 1994). Therefore oltipraz is considered as a potential agent with which to induce glucuronidation prior to, or with, CPT-11 treatment. Doses such as those described by Ansher et al., 1983; Davies & Schnell, 1991; and Egner et al., 1994; each incorporated herein by reference, may be employed.

EXAMPLE 10

Arvloxycarboxyllic Acids and Fibric Acids

A. Clofibrate

Clofibrate is propanoic acid, 2-(4-chlorophenoxy)-2-methyl-,ethyl ester; ATROMID-S™ and is available from Ayers.

It can be prepared by condensing phenol with ethyl 2-chloro-2-methylpropionate in the presence of a suitable dehydrochlorinating agent and then chlorinating.

The drug is hydrolyzed to clofibric acid during absorption and in its pass through the liver, and it is the acid to which activity is attributed. The acid is bound strongly to plasma proteins. About 60% is metabolized, mostly to a glucuronide conjugate. The half-life is 6 to 25 hr (av 11 hr), except over 100 hr in anuria. Patients having the slower rates of metabolism have better clinical responses.

Suitable doses for use in adults are contemplated to be similar to those doses used to achieve an antihyperlipidemic effect, namely 500 mg 3 times a day for persons weighing less than 120 lb, 4 times a day for those weighing 120 to 180 lb, and 5 times a day for those over 180 lb, or to achieve an antidiuretic effect, namely 6 to 8 g/day in 2 to 4 divided doses. Clofibrate is available in 500 mg capsules.

B. Ciprofibrate

Several chemical relatives of clofibrate, collectively referred to as fibric acids, have proven to be less toxic and more effective for the treatment of hypertriglyceridemia and hypercholesterolemia than has clofibrate itself. One of these drugs is ciprofibrate.

C. Gemfibrozil

Gemfibrozil has been used extensively in the United States and Europe since the mid 1970s and was approved for use in the United States in 1982. Administration of a single dose of gemfibrozil (600 mg) results in a plasma concentration of about 15 µg/ml after 2 hours and 5 µg/ml after 9 hours. Final excretion occurs primarily through the kidneys, mainly as the glucuronide. Gemfibrozil LOPID™ available from Parke as. Davis is 300-mg capsules and 600-mg tablets. The usual recommended dosage (for adults only) is 600 mg twice daily, taken 30 minutes before the morning and evening meals.

D. Fenofibrate

A related compound, fenofibrate, is widely prescribed in Europe. The usual dosage is 100 mg orally after each meal. Administration of the drug with meals reduces the gastric irritation that occurs in a few patients.

E. Bezafibrate

The structural formulas of clofibrate and the related fibric acid derivatives are shown in Table 4. Gemfibrozil, fenofibrate, bezafibrate, and ciprofibrate all are more potent than clofibrate and can be used in lower doses.

TABLE 4

Structural Formulas of Fibric Acids

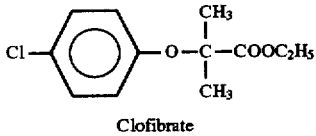
Clofibrate

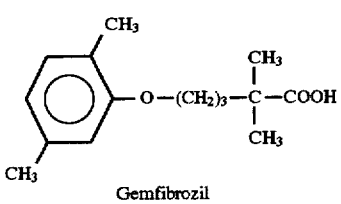
Gemfibrozil

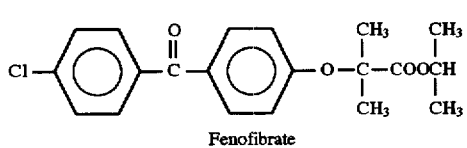
Fenofibrate

TABLE 4-continued

Structural Formulas of Fibric Acids

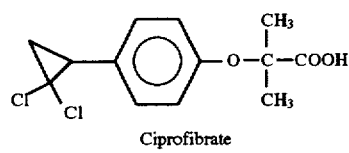
Ciprofibrate

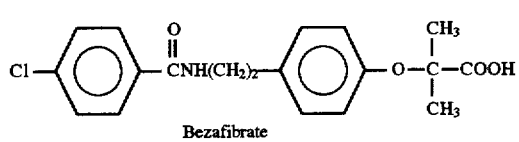
Bezafibrate

EXAMPLE 11

Anti-convulsants

A. Phenobarbital

Phenobarbital is 2,4,6(1H,3H,5H)-Pyrimidinetrione, 5-ethyl-5-phenyl-, Phenylethylmalonylurea, and is available from various commercial sources.

Phenobarbital is prepared by converting Benzyl chloride into phenylacetic ester (ethyl phenylacetate) by treating with sodium cyanide and then hydrolyzing with acid in the presence of alcohol. The ester is condensed in the presence of alcohol and metallic sodium with ethyl oxalate, forming diethyl sodium phenyloxaloacetate. HCl is added to liberate diethyl phenyloxaloacetate which, on being distilled at about 180°, splits off carbon monoxide, and forms phenylmalonic ester $[C_6H_5CH(COOC_2H_5)_2]$. The hydrogen of the CH in the phenylmalonic ester is then ethylated and the resulting ethylphenylmalonic ester condensed with urea.

Approximately 80% of an oral dose is absorbed and peak plasma levels are reached in 16 to 18 hr. Therapeutic plasma levels range from 10 to 30 µg/mL. Apparent plasma half-life varies from 50 to 120 hr in adults. Suitable doses for use in adults are contemplated to include 30 to 120 mg in 2 or 3 divided doses; 100 to 320 mg and 50 to 100 mg 2 or 3 times a day. Usual range of dose, 30 to 600 mg a day. Phenobarbital is available in many dosage forms: elixir; 15 or 20 mg/5 mL; capsules: 16 mg; tablets: 8, 16, 32, 65 and 100 mg.

Phenobarbital sodium is 2,4,6(1H,3H,5H)-Pyrimidinetrione, 5-ethyl-5-phenyl-, monosodium salt; and is available from Winthrop and various commercial sources. It can be prepared by dissolving phenobarbital in an alcohol solution of an equivalent quantity of NaOH and evaporating at low temperature. Because it is soluble in water, it may be administered parenterally. It may be given by slow intravenous injection. Suitable doses for adults include: intramuscular or intravenous 100 to 130 mg; 200 to 300 mg repeated in 6 hr if necessary. It is available in dosage forms of injection: 30, 60, 65 and 130 mg/mL; sterile powder, 120-mg ampuls.

B. DILANTIN™ (Phenytoin)

Phenytoin is 2,4-Imidazolidinedione, 5,5-diphenyl-, Diphenylhydantoin and is available from Parke-Davis.

Suitable dose ranges are oral, 300 to 600 mg a day; usual, adult, 100 mg 3 times a day; the dose then is individualized. It is available in dosage forms of chewable tablets: 50 mg. Oral suspension: 30 mg/5 mL and 125 mg/5 mL.

Phenytoin Sodium is 2,4-Imidazolidinedione, 5,5-diphenyl-, monosodium salt also known as ALEPSIN™; EPANUTIN™; EPTOIN™ and DILANTIN SODIUM™, and is available from Parke-Davis. It is prepared by treating benzaldehyde with a solution of sodium cyanide, 2 moles of benzaldehyde are condensed (benzoin condensation) into one mole of benzoin, which is oxidized to benzil with nitric acid or cupric sulfate. The benzil is then heated with urea in the presence of sodium ethoxide or isopropoxide, forming phenytoin sodium.

Therapeutic plasma levels range from 10 to 20 µg/mL in adults and 5 to 20 µg/mL in children. Toxic levels range from 30 to 50 µg/mL and lethal levels approximate 100 µg/mL, these levels should be avoided.

There are two distinct forms of Phenytoin Sodium Capsules: the rapid-release type (Prompt Phenytoin Sodium Capsules) and the slow-dissolution type (Extended Phenytoin Sodium Capsules). The former have a dissolution rate of not less than 85% in 30 min and are used for 3 or 4 times a day dosing, whereas the latter have a slow dissolution rate of 15 to 35% in 30 min, 45 to 65% in 1 hr and not less than 85% in 2 hr and may be used for once-a-day dosing. Studies comparing doses of 100 mg three times a day of Prompt Phenytoin Sodium Capsules with a single, daily dose of 300 mg of Extended Phenytoin Sodium Capsules DILANTIN KAPSEALS™; Parke Davis) indicate that absorption, peak plasma levels, biological half-life, difference between peak and minimum values and urinary recovery are equivalent.

Its metabolism may be altered significantly by concomitant use of other drugs. Drugs which increase its serum levels include chloramphenicol, dicumarol, tolbutamide, isoniazid, phenylbutazone, acute alcohol intake, salicylates, chlordiazepoxide, phenothiazines, diazepam, estrogens, ethosuximide, halothane, methylphenidate, sulfonamides, cimetidine and trazodone. Drugs which decrease its serum levels include carbamazepine, chronic alcohol abuse, reserpine and preparations containing calcium. Drugs which either increase or decrease its serum levels include phenobarbital, valproic acid and valproate sodium.

Suitable dose ranges are: oral, 200 to 600 mg a day; usual, oral, 100 mg up to 4 times a day; usual, intravenous, 150 to 250 mg, followed, if necessary, by 100 to 150 mg 30 min later (intravenous administration should not exceed 50 mg/min); usual, intramuscular, 100 to 200 mg every 6 to 8 hr for a total of 3 or 4 injections. Dosage forms—capsules: 100 mg (with phenobarbital 0.16 or 0.32 mg); prompt capsules: 30 and 100 mg; extended (once-a-day dosing) capsules: 30 and 100 mg.

C. Clonazepam

Clonazepam is 2H-1,4-Benzodiazepin-2-one, 5-(2-chlorophenyl)-1,3-dihydro-7-nitro-, and is available from Roche.

Clonazepam is prepared by reacting o-Chlorobenzoyl chloride with p-nitroaniline to form 2-amino-5-nitro-2'-chlorobenzophenone, and this is condensed with bromacetyl bromide to form 2-bromoacetamido-5-nitro-2'-chlorobenzophenone, then treated with ammonia to form the corresponding acetamido compound. The acetamido compound is converted to its hydrochloride with anhydrous HCl in methanol, dissolved in boiling methanol and cyclized to clonazepam using pyridine as the catalyst. Therapeutic plasma levels range from 20 to 80 ng/mL.

Suitable doses in adults are contemplated to include 1.5 mg in 3 divided doses; or 0.5 to 1.0 mg every 3 days. Maximum daily dose is 20 mg. It is available in dosage forms of tablets: 0.5, 1.0 and 2.0 mg.

D. Clotrimazole

Clotrimazole is 1H-Imidazole, 1-[2-chlorophenyl) diphenylmethyl]-also termed LOTRIMIN™, available from schering; and MYCELEX™, available from Miles. It is prepared from the reaction between imidazole and 2-chlorotriphenylmethyl chloride using trimethylamine as a proton receptor.

Suitable doses include, for adults, 5 g of 1% of cream or one 100-mg tablet daily, preferably at bedtime, for 7 to 14 consecutive days; 10 mg as a troche, slowly dissolved in the mouth 5 times a day. It is available in dosage forms of cream: 1%; vaginal cream: 1% (one applicator full contains 5 g of cream); topical solution: 1%; vaginal tablets: 100 and 500 mg; troches: 10 mg.

EXAMPLE 12

Corticosteroids

A. Dexamethasone

Dexamethasone is pregna-1,4-diene-3,20-dione, 9-fluoro-11,17,21-trihydroxy-16-methyl-,(11β,16α)-, and is available from various commercial sources. Miller et al. (1991) showed that oral dexamethasone can be used to advantage with verapamil in cancer treatment.

Suitable doses for use in adults include, initially, 500 µg to 9 mg a day in single or divided doses, and usually less; or 8 mg every other day for 1 mo; or 2 mg 2 or 3 times a day after parenteral dexamethasone sodium phosphate. It is available in dosage forms of topical aerosol: 0.01 and 0.04%; elixir: 0.5 mg/5 mL; gel: 0.1%; ophthalmic suspension: 0.1%; tablets: 0.25, 0.5, 0.75, 1, 1.5, 2, 4 and 6 mg.

Dexamethasone sodium phosphate is pregn-4-ene-3,20-dione, 9-fluoro-11,17-dihydroxy-16-methyl-21-(phosphonooxy)-,disodium salt, (11β,16α)-, dexamethasone 21- (Disodium Phosphate); also known as DECADRON™ available from MSD; and DALALONE™ available from Forest.

It is one of the most soluble adrenocortical compounds. Thus, it lends itself well to intravenous administration, local injection and inhalation, and even to solutions and water-based ointments for topical application. Suitable doses are intravenous or intramuscular, adult, 420 µg to 7.5 mg a day, the dosage being decreased when a response occurs. Intra-articular, intralesional or soft-tissue injection, 170 µg to 5 mg. It is available in dosage forms of injection: 3.3, 8.33, 16.66; with various aerosols, sprays, creams, ointments and ophthalmic solutions also being available.

TABLE 5

| Steroids[1] for use in targeted angiogenesis inhibitors | |
|---|---|
| Tetrahydrocorticosterone | Tetrahydrocortexolone |
| Cortisol (hydrocortisone) | Prednisone |
| Tetrahydrocortisol | Triamcinolone |
| 11 α-epihydrocortisol | Alclometasone |
| Cortisone | Amcinonide |
| Tetrahydrocortisone | Clobetasol |
| Corticosterone | Clobetasone |
| Deoxycorticosterone | Clocortolone |
| Cortexolone | Desonide |
| Beclomethasone dipropionate | Desoximetasone |
| Betamethasone | Diflorasone |
| Dexamethasone | Fluocinolone acetonide |
| Flunisolide | Fluocinonide |
| Methylprednisolone | Fluorometholone |
| 17 α-hydroxyprogesterone | Fluocortolone |
| Tetrahydro S | Flurandrenolide |
| Paramethasone | Halcinonide |
| Prednisolone | Medrysone |
| Pregnenolone | Mometasone |

[1]Plus derivatives thereof, such as the phosphate, hemisuccinate, valerate, sulfate, acetate, benzoate, sodium phosphate, cypionate, sodium succinate, tebutate, acetonide, diacetate, hexacetonide, propionate, dipropionate, and piralate derivatives.

EXAMPLE 13

Oral Contraceptives

A variety of oral contraceptives may be employed, including Ethynodiol Diacetate; Levonorgestrel, available from Wyeth; Medroxyprogesterone Acetate, available from Upjohn or Reid Rowell; Norethindrone, available from Ortho, Syntexor Parke-Davis; Norethindrone Acetate, available from Ayerst or Parke-Davis; Norethynodrel, available from Searle; Norgestrel, available from Wyeth.

They are available in doses of Ethynodiol Diacetate/ Ethinyl Estradiol tablets of 1 mg/35 or 50 µg; Ethynodiol Diacetate/Mestranol tablets of 0.5 or 1 mg/100 µg; Levonorgestrol/Ethinyl Estradiol, Monophasic tablets of 0.15/30 mg/µ; Triphasic tablets of 0.05/30, 0.075/40 and 0.125/30 mg/µ; Norethindrone/Ethinyl Estradiol, Monophasic tablets of 1 mg/50 µ, 1 mg/35 µg, 0.5 mg/35 µg, 0.4 mg/35 µg; Biphasic tablets of 0.5 B mg/35 µg (×10) and 1 mg/35 µg (×11); Triphasic tablets of 0.5 mg/35 µg (×7), 1 mg/35 µg (×7) and 0.5 mg/35 µg (×7) or 0.5 mg/35 µg (×7), 0.75 mg/35 µg (×7) and d1 mg/35 µg (×7); Norethindrone/ Mestranol, Monophasic tablets of 1/20, 1/50, 1/80, and 0.5 or 2/100 mg/ µg. Biphasic tablets of 0/20 (×17) and 0.25/20 (×7) or 0/40 (×17) and 0.5/40 (×7) or 0/80 (×17) and 1/80 (×7) mg/µg; Norethindrone Acetate/Ethinyl Estradiol tablets of 1/20, 1.5/30, 1/50 and 2/50 mg/µg; Norethynodrel/ Mestranol tablets of 2.5:100, 5:75 and 9.85:150 mg:µg; and Norgestrel/ Mestranol tablets of 500:50 and 300:30 µg:µg.

EXAMPLE 14

Cyclophosphamide

Cyclophosphamide is 2H-1,3,2-Oxazaphosphorin-2-amine, N,N-bis(2-chloroethyl)tetrahydro-, 2-oxide, monohydrate; termed CYTOXAN™ available from Mead Johnson; and NEOSAR™ available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parenteral routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg.

EXAMPLE 15

Retinoic Acids

It is retinoic acid, or so-called vitamin A acid, which is formed when the aldehyde group of retinene (retinal) is oxidized to a carboxyl group. Together with certain carotenoids, vitamin A appears to enhance the function of the immune system, to reduce the consequences of some infectious diseases, and to protect against the development of certain malignancies. As a result, there is considerable interest in the pharmacological use of retinoids for the prophylaxis of cancer and for the treatment of various premalignant conditions.

There are many types of preparations that contain retinol. Vitamin A capsules contain 3 to 15 mg of retinol (10.000 to 50,000 I.U.) per capsule; oral drops are also available. A water-miscible preparation (15 mg/ml; 50,000 I.U./ml) can be given intramuscularly. Isotretinoin (13-cis-retinoic acid; ACCUTANE™) is available for oral use as 10-, 20-, and 40-mg capsules. The initial daily dose is usually 0.5 to 1 mg/kg in two divided doses up to a maximum of 2 mg/kg. A course of therapy is usually 15 to 20 weeks; which may be repeated after an interval of 2 months. Etretinate TEGISON™; Roche is available for oral use as 10- and 25-mg capsules. Initial daily doses are usually 0.75 to 1 mg/kg up to a maximum of 1.5 mg/kg.

EXAMPLE 16

Rifampin

Rifampin includes Rifamycin, 3-[[(4-methyl-1-piperazinyl)imino]methyl]-, RIFAMPICIN™; RIFADIN™ available from Merrell Dow; and RIMACTANE™ available from Ciba-Geigy.

Rifamycin SV, which may be prepared by the method of Sensi et al. (U.S Pat. No. 3,313,804), is converted to the 8-carboxaldehyde derivative, known also as 3-formylrifamycin SV, and this is condensed with 1-amino-4-methylpiperazine in a Schiff base reaction to yield rifampin.

Metabolism is dose-dependent with doses above 300 to 450 mg; with therapeutic doses the serum half-life is 1.5 to 5 hr. Even so, the drug is usually administered at 8- to 12-hr intervals, because absorption is slow enough to sustain effective levels for 8 to 10 hr.

Suitable adult doses include, orally, 600 mg once a day, taken with a glass of water at least 1 hr before a meal; elderly or debilitated patients, 10 mg/kg once a day. It is available in dosage forms of capsules: 150 and 300 mg; capsules (in combination with isoniazid): 300 mg rifampin and 150 mg isoniazid; tablets: 300 mg.

EXAMPLE 17

Disulfiram (ANTABUSE™)

Disulfiram is Thioperoxydicarbonic diamide, tetraethyl-, Tetraethylthiuram Disulfide, known as ANTABUSE™, available from Ayerst. Disulfiram is prepared by treating a cold solution of diethylamine and carbon disulfide in alcohol with an alcoholic solution of iodine. Ice water way be added to hasten separation of the disulfiram. Suitable doses are usually, oral, initially up to 500 mg a day for the first 2 or 3 wk; usual, maintenance, 250 mg a day. It is available in dosage forms of tablets: 250 and 500 mg.

EXAMPLE 18

P-glycoprotein Binding

To determine whether CPT-11 and SN-38 interact with p-glycoprotein , membrane vesicles from the multidrug resistant breast tumor cell line MCF-7/ Adr were used and the inhibitory effects on the binding of 5 nM of a photoaffinity analog of verapamil to p-glycoprotein were determined.

A. Photoaffinity labeling of cells:

Membrane vesicles from the multidrug resistant human breast cancer tumor cell line MCF-76/ Adr were used. The vesicles were photolabeled with 50 nM of a photoaffinity analog of verapamil, N-(p-azido-[3,5-$^{125}$I]salicyl)-verapamil ([$^{125}$I]BAS-VP] in the absence or presence of increasing concentrations of CPT-11, SN-38 or nonlabeled verapamil (positive control. Immunoprecipitation of [$^{125}$I] verapamil was performed with a monoclonal antibody specific for P-gp. Proteins were separated by 5-15% sodium dodecyl sulfate polyacrylamide gel electrophoresis (SDS-PAGE) and detected by fluorography.

CPT-11 (10 μM) and SN-38 (100 μM) inhibited p-glycoprotein affinity labeling by 80% and 60%, respectively, suggesting that both compounds were substrates for p-glycoprotein (FIG. 5).

EXAMPLE 19

CPT-11 and Cyclosporive a Administration p-glycoprotein is a 170-180 kDa membrane glycoprotein that functions as an ATP-dependent transmembrane efflux-pump and is considered to be responsible for the development of multidrug resistance (Endicott & Ling, 1989). This protein has been reported to be located on the bile canalicular domain of the hepatocyte and probably plays a role in the excretion of cellular xenobiotics (Thiebaut et al., 1987; Kamimoto et al., 1989). Generally, agents that reverse multidrug resistance do so by competing with cytotoxic drugs for a common binding site on p-glycoprotein has been reported to transport cyclosporine, an immunosuppressive agent that has aided in successful organ transplants in humans (Foxwell et al., 1989; Saeki et al., 1993). There is evidence demonstrating inhibition of p-glycoprotein mediated transport of several compounds in humans by cyclosporine A due to competitive or noncompetitive binding of cyclosporine A to p-glycoprotein sites (Tamai & Safa, 1991; Lannoy et al., 1992; Okamura et al., 1993; Zacherl et al., 1994; Charuk et al., 1994). The studies in Example 18 demonstrated that CPT-11, SN-38 as well as SN-38G were substrates of p-glycoprotein. The objective of the present study was to determine the effects of p-glycoprotein inhibition by cyclosporine A on the biliary transport of CPT-11 and its metabolites.

A. Materials and Methods

Materials: CPT-11 solution was obtained from the Yakult Honsha Co., Tokyo, Japan, and cyclosporine A (SANDIMMUNE™) was purchased from Sandoz Pharmaceutical Co., East Hanover, NJ. All other chemicals were of analytical grade and were obtained from Fisher Scientific Co., Itasca, Ill.

Animal protocol: Female Wistar rats (~200 gm) having a permanent catheter installed in the right jugular vein were obtained from Charles River Breeding Laboratories (Wilmington, Mass.). The rats were maintained in metabolism cages for at least 24 hours prior to the studies, and food and water were supplied ad libitum.

To investigate the effect of cyclosporine A on CPT-11 disposition, the animals were divided into two groups. The control group received an intravenous bolus administration of CPT-11 through the catheter at doses of 6 mg/kg, 10 mg/kg or 20 mg/kg. The pretreated group of rats received an intravenous bolus injection of cyclosporine A (60 mg/kg) five minutes prior to receiving the dose of CPT-11. The catheter was flushed with 500 μl of physiologic saline after each drug administration.

Serial blood samples (200 μl) were withdrawn through the catheter at 3, 5, 10, 15, 30, 60, 120, 240 and 260 minutes following CPT-11 administration. After each sample the catheter was flushed with an equal volume of physiologic saline. The samples were immediately centrifuged at 2500×g for 10 minutes and the plasma obtained was stored at -70° C. until analysis. CPT-11, SN-38 and SN-38G in 10-20 μl plasma samples were quantitated by a the reversed-phase HPLC method as previously described (Gupta et al., 1994b).

Data Analysis: The plasma concentration-time profile of the control and pretreated groups of rats were analyzed using non-compartmental methods (PCNONLIN, SCI, Lexington, Ky.). The systemic exposure of CPT-11 and metabolites was estimated as the area under the concentration-time curve from time 0 to 6 hours (AUC). The nonparametric Mann-Whitney test was used to test for differences in AUC between the control and pretreated groups.

B. Results

Cyclosporine A significantly elevated plasma concentrations of CPT-11, SN-38 and SN-38G compared to control plasma levels at all three dose levels of 20 mg/kg, 10 mg/kg and 6 mg/kg (FIG. 6A, FIG. 6B, FIG. 6C, FIG. 7A, FIG. 7B, FIG. 7C, FIG. 8A, FIG. 8B, FIG. 8C). Onset of the progressive increase in the concentrations occurred between 15 to 30 minutes following CPT-11 dose suggestive of a time lag between cyclosporine dose and p-glycoprotein inhibition. The elevations appeared to be independent of the CPT-11 dose with a net increase in AUC across the 3 dose levels being about 3 fold for both CPT-11 and SN-38 and about 2 fold for SN-38G (Table 6; Table 7).

TABLE 6

EFFECT OF INHIBITION OF BILIARY EXCRETION ON CPT-11 DISPOSITION

| GROUP | AUC$_{CPT-11}$ ng.hr/ml | AUC$_{SN-38}$ ng.hr/ml | AUC$_{SN-38G}$ ng.hr/ml |
|---|---|---|---|
| CPT-11: 20 mg/kg Cyclosporine: 60 mg/kg (FIG. 6A, FIG. 6B, FIG. 6C,) | | | |
| Control (n = 4) | 7695.8 ± 2674 | 364.89 ± 44.19 | 556.52 ± 167.03 |
| Pretreated (n = 3) | 19722 ± 2631 | 1052.0 ± 32.29 | 1062.4 ± 83.54 |
| Increase | 2.56 fold | 2.88 fold | 1.91 fold |
| CPT-11: 10 mg/kg Cyclosporine: 60 mg/kg (FIG. 7A, FIG. 7B, FIG. 7C,) | | | |
| Control (n = 3) | 3130.3 ± 726.83 | 200.66 ± 65.85 | 354.08 ± 44.57 |
| Pretreated (n = 4) | 10808 ± 3229 | 617.29 ± 100.15 | 729.16 ± 365.45 |
| Increase | 3.45 fold | 3.08 fold | 2.06 fold |
| CPT-11: 6 mg/kg Cyclosporine: 60 mg/kg (FIG. 8A, FIG. 8B, FIG. 8C,) | | | |
| Control (n = 3) | 1728.6 ± 99.32 | 198.0 ± 21.96 | 241.92 ± 87.55 |

TABLE 6-continued

EFFECT OF INHIBITION OF BILIARY EXCRETION ON CPT-11 DISPOSITION

| GROUP | $AUC_{CPT-11}$ ng.hr/ml | $AUC_{SN-38}$ ng.hr/ml | $AUC_{SN-38G}$ ng.hr/ml |
|---|---|---|---|
| Pretreated (n = 4) | 5392.9 ± 2109 | 497.33 ± 52.09 | 440.68 ± 209.1 |
| Increase | 3.12 fold | 2.51 fold | 1.82 fold |
| Overall Increase | 3.04 fold | 2.82 fold | 1.93 fold |

Effect of cyclosporine A on the disposition of CPT-11 and metabolites in rats. The control group received an intravenous bolus CPT-11 dose of 20, 10 or 6 mg/kg. The pretreated group received an intravenous bolus of cyclosporine (60 mg/kg) five minutes before receiving CPT-11. The increase in the bioavailability of CPT-11, SN-38 and SN-38G was calculated as the ratio of the 6 hr AUC of the pretreated group to the control group. The overall increase as determined as the mean of the increases observed each dose level. *: significantly high compared to control ($p < 0.05$). Data is represented as mean ±SD.

TABLE 7

EFFECT OF INHIBITION OF BILIARY EXCRETION ON CPT-11 DISPOSITION
Effect of lower dose of cyclosporine

| GROUP | $AUC_{CPT-11}$ ng.hr/ml | $AUC_{SN-38}$ ng.hr/ml | $AUC_{SN-38G}$ ng.hr/ml |
|---|---|---|---|
| CPT-11: 10 mg/kg Cyclosporine: 30 mg/kg | | | |
| Control (n = 4) | 3130.3 ± 726.83 | 200.66 ± 65.85 | 354.08 ± 44.57 |
| Pretreated (n = 2) | 12147 | 413.58 | 844.43 |
| Increase | 3.88. fold | 2.06 fold | 2.38 fold |

The increase in the bioavailability of CPT-11, SN-38 and SN-38G (reflected by the increased in AUC) following cyclosporine administration was secondary to reduction of inhibition of p-glycoprotein associated transport. Since p-glycoprotein has been reported to be located in the bile canalicular face of hepatocytes as well as in the apical surface of the proximal tubular cells in the kidney, reduction in both biliary and renal excretion could shave contributed to the decrease in total body clearance of CPT-11 and metabolites, resulting in significantly increased AUC. However, biliary excretion is the major pathway of elimination of CPT-11, SN-38 and SN-38G with only about 20% of a CPT-11 dose being eliminated in the urine in rats (Kaneda & Yokokura, 1990). Therefore, reduction in biliary excretion probably had the major contribution to the reduced clearance and is reflective of the significant contribution of this excretion pathway to the overall total body clearance of CPT-11 and metabolites.

The inhibitory effect of cyclosporine has not been reported to lead to irreversible damage to cells and cellular integrity is maintained following removal of cyclosporine (Tamai & Safa, 1991). In an in vitro study of the inhibition of transport of digoxin in the presence of cyclosporine in apical tubular cells overexpressing p-glycoprotein , the transport recovered to control level following removal of cyclosporine form the medium. Therefore, it can be concluded that the binding of cyclosporine to p-glycoprotein is reversible and the duration of effect would be dependent on the presence of cyclosporine. In rats and humans, the plasma half-life of cyclosporine has been reported to be about 4 to 6 hours. Hence the effect of p-glycoprotein inhibition of CPT-11 disposition could be expected to be observed for a maximum period of 24 hours following cyclosporine delivery, during which time about 90% of the drug (cyclosporine) would have been eliminated from the body.

Concomitant administration of cyclosporine A enhanced the AUC of drug as well as the metabolite. Since cyclosporine inhibits biliary excretion of SN-38, the accumulation of this metabolite in the central compartment is due to significantly lowered SN-38G in the gut. A reduction in biliary concentration and increase in plasma concentration of SN-38, would not only result in reduced toxicity but would also enhance the therapeutic efficacy of CPT-11. Higher plasma SN-38 would cause an increased amount of the active metabolite being distributed to the malignant tissues. Thus potentially the same therapeutic effect could be achieved using a substantially lower dose of CPT-11. However, since the lowered biliary excretion of SN-38 is dependent upon the presence of cyclosporine, accumulation of SN-38 in the gut could result following systemic elimination of cyclosporine. Presence of phenobarbital could reverse this phenomenon by enhancing the detoxification of SN-38. In conclusion, the coadministration of cyclosporine along with CPT-11 is proposed to be an attractive alternative for reducing toxicity and enhancing the therapeutic indexof CPT-11. Even more attractive is the combined use of cyclosporine, phenobarbital and CPT-11.

Cyclosporine A is currently proposed for use at 10 mg/kg by a 6-hour infusion, and CPT-11 at 25 mg/m$^2$ by a 90-minute infusion beginning about 3 hours after the initiation of cyclosporine infusion.

In the present, and all the following examples, the dosage regimens suggested are provided as starting points for doses of second agents that decrease biliary transport protein activity, as exemplified by decreasing p-glycoprotein activity. The doses described may be considered for therapeutic use in combination with camptothecins such as CPT-11, however, such doses are not intended to be optimum values, but to provide a range that can be readily optimized by a physician in the normal course of events. The toxic and lethal doses, if quoted for further guidance, should be avoided.

EXAMPLE 20

Cyclosporines and Staurosporines

A. Cyclosporines

Thalhammer et al. (1994) showed that p-glycoprotein-mediated transport of the cationic dye, acridine orange, across the bile canaliculi was inhibited by cyclosporine A.

Pourtier-Manzanedo et al. (1992) reported that the non-immunosuppressive cyclosporine derivative, SDZ PSC 833, inhibited p-glycoprotein. These authors also showed that the semi-synthetic cyclopeptolide, SDZ 280–446, was a p-glycoprotein blocker.

Boesch et al. (1991) also showed that SDZ PSC 833 was an effective inhibitor. In studies with target cells, PSC 833 was at least one order of magnitude more active than cyclosporine A in restoring drug sensitivity of multi-drug resistance (MDR) P388 cells.

Boesch & Loor (1994) later reported that SDZ PSC 833. SDZ 280–446, cyclosporine A and verapamil were effective at inhibiting p-glycoprotein. CsA, SDZ 280–446 and SDZ PSC 833 were shown to be stronger inhibitors than verapamil, with SDZ PSC 833 still exhibiting inhibition of p-glycoprotein function even two days after a single pulse exposure. The studies of Boesch & Loor (1994) regarding the persistence of Pgp inhibition conferred by some agents can thus be combined with the teachings herein to allow even more effective clinic protocols to be designed.

Zacherl et al. (1994) also reported that verapamil, cyclosporine A and SDZ PSC 833 inhibited p-glycoprotein-mediated vinblastine transport across HCT-8 intestinal carcinoma monolayers. The non-immunosuppressive derivative SDZ PSC 833 was again reported to be the most effective inhibitor, exhibiting inhibition at concentrations as low as 10 ng/ml (9 nM). In addition to its high inhibitory capacity, the inhibitory activity of PSC 833 is not affected by acidic extracellular conditions.

Cyclosporin A [59865-13-3] $C_{62}H_{111}N_{11}O_{12}$ (1202.63) is used to suppress helper T-lymphocytes without significantly affecting suppressor T-lymphocytes or B-lymphocytes. Thus, it is a selective immunosuppressive drug without the cytotoxicity characteristic of most other immunosuppressive drugs. It has a modest effect to suppress some humoral immunity.

It is the most efficacious immunosuppressive for prevention of graft rejection in allogenic transplantation of kidney, liver or heart. It is used also in the management of severe aplastic anemia, some cases of myasthenia gravis, childhood diabetes (Type I) of recent onset, Graves' disease, Crohn's disease, multiple sclerosis, pemphigus and pemphigoid, dermatomyositis, polymyositis, atopic dermatitis, severe psoriasis, Bechcet's disease, uveitis, biliary cirrhosis and pulmonary sarcoidosis. It usually is employed in combination with a glucocorticoid. Although combination with other immunosuppressives usually is avoided, in bone-marrow transplantation it commonly is combined with methotrexate.

Doses are, intravenous infusion, adults and children, 2 to 6 mg/kg/day, starting 4 to 12 hr before transplantation and continuing until oral dosage can be tolerated. Oral, adults and children, initially 12 to 15 mg/kg/day starting 4 to 12 hr before transplantation or after IV infusion and continuing for 1 to 2 wk, after which the dose is diminished by 5% wk to a maintenance dose of 5 to 10 mg/kg/day. It is available in injectable dosage forms of 250 mg/5 mL; and oral solutions of 5 g/100 mL.

3'-Keto-cyclosporine D, which has negligible immunosuppressive activity, also strongly inhibits p-glycoprotein of multi-drug resistant mammalian tumor cells (Bell et al., 1994) and thus may be in the present invention.

B. Cefoperazone

Cefoperazone is a third-generation cephalosporin with antibacterial activities. It is approved for use in urinary tract infections caused by Enterobacter, *P. aeruginosa* and anaerobic cocci and bacilli; and in respiratory tract infections caused by Enterobacter, *E. coli* and other organisms.

Orally, it is absorbed poorly. An intravenous dose yields a peak plasma concentration of 250 to 357 µg/mL depending on the rate of delivery, an intramuscular dose 80 to 120 µg/mL. In plasma, 82 to 93% is protein-bound. The volume of distribution 0.13 to 0.20 mL/g in adults but 0.5 mL/g in neonates. Biliary secretion eliminates 70% and urinary excretion 30% of the drug. Dose adjustments are needed in hepatic but not in renal failure.

Doses of Cefoperazone Sodium A (in cefoperazone equivalents are: intramuscular or intravenous infusion, adults, for mild infections, 1 to 2 g every 12 hr and, for severe infections, 1.5 to 3 g every 6 hr, 2 to 4 g every 8 hr or 3 to 6 g every 12 hr. It is available in powder forms for injection of 1 and 2 g.

C. Staurosporins

Staurosporine derivatives, such as NA-382, also inhibit multidrug resistance by inhibiting p-glycoprotein (Miyamoto et al., 1993). The effects of the staurosporine derivative, N-ethoxycarbonyl-7-oxo-staurosporine (NA-382) on multidrug resistance in tumor cells were shown to be due to inhibiting drug binding to p-glycoprotein. Therefore, both staurosporine and NA-382 may also be used as second agents in accordance with camptothecins.

EXAMPLE 21

Calcium Channel Blockers

Calcium channel blockers, also termed calcium entry blocking drugs (CEBs) or calcium antagonists, are a group of agents whose main pharmacological effect is to prevent or slow the entry of calcium into cells via specialized calcium channels. Five of these drugs are available in the U.S.: verapamil, nifedipine, nitrendipine, nicardipine and diltiazem. Nifedipine and nitrendipine are dihydropyridines, a chemical class to which most new calcium channel blockers belong.

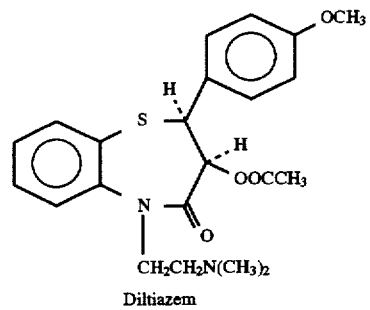

Diltiazem

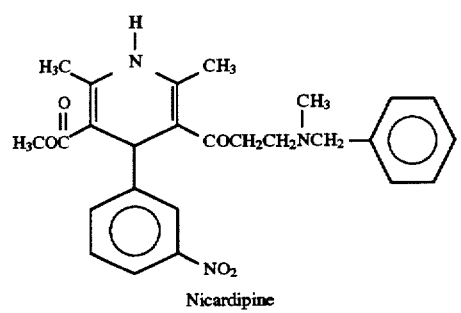

Nicardipine

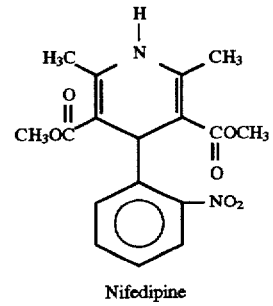

Nifedipine

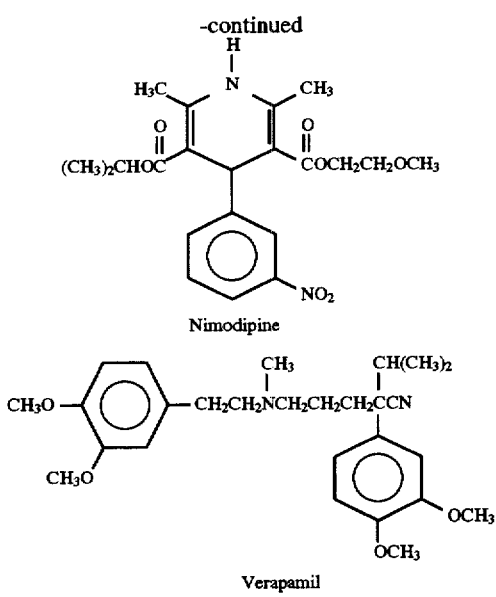

Nimodipine

Verapamil

A. Dihydropyridine Analogues

Certain dihydropyridine analogues inhibit p-glycoprotein, as shown by inhibiting photolabeling of p-glycoprotein in human cells (Kamiwatari et al., 1989). Ten synthetic dihydropyridine analogues were investigated for their ability to reverse drug resistance in a multidrug-resistant human carcinoma cell line. Four dihydropyridine analogues completely reversed the resistance, three lowered the resistance, but three had less effect. The seven best inhibitory dihydropyridines described by Kamiwatari et al. (1989) are contemplated for use in the invention. The cationic compounds cepharanthine and reserpine also showed inhibition in this study.

B. Verapamil

Verapamil is known to be a competitive inhibitor of p-glycoprotein, as described by Inoue et al. (1993); Hunter et al. (1993); Hori et al. (1993); Pourtier-Manzanedo et al. (1992); Boesch & Loor (1994); Zacherl et al. (1994); Shirai et al. (1991); Morris et al. (1991); Muller et al. (1994); and Miyamoto et al. (1992b).

Thalhammer et al. (1994) showed that p-glycoprotein-mediated transport of the cationic dye, acridine orange, across the bile canaliculi was inhibited by cyclosporine A and verapamil. The ATP-dependent transport of amphiphilic cations across the hepatocyte canalicular membrane by p-glycoprotein was also studied by Muller et al. (1994). Transport of permanently charged amphiphilic cations was inhibited by verapamil, quinidine and daunorubicin.

Bear (1994) showed that verapamil, colchicine, vinblastine daunomycin and (50 microM) blocked an outwardly-rectifying chloride channel that was proposed to be associated with p-glycoprotein expression.

Ohi et al. (1992) used the calcium-channel blocker, verapamil, with adriamycin in chemotherapy for superficial bladder cancer. Five ampules (10 ml) of injectable verapamil were given.

Verapamil hydrochloride is benzeneacetonitrile, α-[3-[[2-(3,4-dimethoxyphenyl)ethyl]-methylamino]propyl]-3,4-dime thoxy-a-(1-methylethyl)-, hydrochloride; also termed CALAN™ and ISOPTIN™, and available from Searle, Knoll and Parke-Davis.

It is more than 90% absorbed, but only 20 to 35 % of the dose reaches the system because of extensive hepatic first-pass metabolism. It is bound approximately 90% to plasma proteins. It is metabolized rapidly by the liver to norverapamil and traces of several other metabolites. About 70% of a dose is excreted in urine as metabolites, and 16% of a dose appears in the feces within 5 days; less than 5% is excreted unchanged.

The effects of verapamil are evident within 30 to 60 minutes of an oral dose. Peak effects of verapamil occur within 15 minutes of its intravenous administration. The half-life is 1.5 to 5 hours in normal persons but may exceed 9 hr during chronic therapy. In patients with cirrhosis of the liver, the half-life may be increased to 14 to 16 hr. The half-life is increased in patients with liver disease, due, in part, to an increased volume of distribution. Saturation kinetics have been observed after repeated doses.

Doses are: intravenous, adults, initially 5 to 10 mg (0.075 to 0.15 mg/kg) over a period of 2 min (3 min in the elderly), followed by 10 mg (0.150 mg/kg) after 30 min, if necessary; children, up to 1 yr, initially 0.1 to 0.2 mg/kg over 2 min (with ECG monitoring), repeated after 30 min, if necessary; 1 to 15 yr, initially 0.1 to 0.3 mg/kg, not to exceed 5 mg, repeated after 30 min, if necessary. Oral, adults, 80 mg 3 or 4 times a day or 240 mg once a day in sustained-released form, gradually increased to as much as 480 mg a day, if necessary.

Verapamil is available in injectable dosage forms of 5 mg/2 mL and 10 mg/4 mL; tablet dosage forms of 40 mg, 80 mg and 120 mg; and sustained-telease tablets of 240 mg.

C. Tiapamil

Campain et al. (1993) reported that the tiapamil analog, RO-11-2933, is an inhibitor of p-glycoprotein. A tiapamil analogue was also described as an efflux-blocking drug by Williams et al. (1992). Tiapamil is proposed for use at doses generally equivalent to those of verapamil.

D. Nifedipine

Wilson et al. (1991) reported that nifedipine is a p-glycoprotein inhibitor that is structurally unrelated to verapamil. However, both nifedipine and verapamil belong to the group of calcium channel blockers. Hunter et al. (1993) and Morris et al. (1991) also showed nifedipine to be a p-glycoprotein inhibitor.

Nifedipine is 3,5-Pyridinecarboxylic acid, 1,4-dihydro-2, 6-dimethyl-4-(2-nitrophenyl)-, dimethyl ester; also termed ADALAT™ and PROCARDIA™, available from Miles and Pfizer, respectively. About 90% of an oral dose is absorbed, but its bioavailability is 65 to 70%; there is significant hepatic first-pass metabolism. Greater than 90% of the drug is bound to plasma protein. It is metabolized to inactive metabolites, probably by the liver. Most (80%) of the inactive metabolites are excreted in urine; 15% are excreted in the stool. The half-life is 2 to 6 hours.

Oral doses are, for adults initially 10 mg 3 times a day, to be increased gradually to 20 to 30 mg three or four times a day, if necessary. The usual effective dosage is 10 to 20 mg three times daily, but 20 to 30 mg taken three or four times daily may be necessary. Doses exceeding 180 mg a day are not recommended. It is available in capsule dosage forms of 10 and 20 mg.

E. Diltiazem

Morris et al. (1991) identified diltiazem as a p-glycoprotein inhibitor, along with verapamil, nifedipine and vinblastine.

Diltiazem is benzothiazepin-4(5H)-one, 3-(acetyloxy)-5-[2-(dimethylamino)ethyl]-2,3-dihydro-2-(4-methoxyphenyl)-, (+)-cis-, monohydrochloride, also termed CARDIZEM™ available from Marion. It is 80% absorbed orally, but only 40 to 60% of an oral dose reaches the systemic circulation because of first-pass metabolism in the liver. After administration, it is 70 to 80% bound to plasma protein. Displacement rom protein binding sites by other drugs does not seem to be a clinical problem. It is metabolized extensively by the liver to several metabolites, some of which have weak coronary vasodilator activity. Less than 4% of the drug appears unchanged in the urine. The plasma half-life is about 4 hr.

Oral doses are, for adults, initially: 30 mg 4 times a day before meals and at bedtime, to be increased to 360 mg day, as necessary. The sustained-release preparation is given twice daily. It is available in tablet dosage forms of 30, 60, 90 and 120 mg.

F. Nicardipine

Nicardipine is also proposed for use in the present invention, based on its similarity with the above calcium channel blockers and in light of the studies by Niwa et al. (1992).

Nicardipine has pharmacodynamic and pharmacokinetic properties close to those of nifedipine, and is proposed for use at similar doses. Nicardipine is an effective antianginal and antihypertensive agent.

Nicardipine hydrochloride (CARDENE™) is available in 20- and 30-mg tablets for use in hypertension and angina. The recommended dosage is 20 to 40 mg three times a day. At least 3 days should elapse between adjustments of dosage.

G. Nisoldipine

Nisoldipine is also similar to Nicardipine, with properties close to nifedipine, and having effective antianginal and antihypertensive uses. Nisoldipine is proposed for use with camptothecins in the present invention, in a similar manner to nicardipine and nifedipine.

H. Nimodipine

Nimodipine is also proposed for use in the present invention, based on its similarity with other calcium channel blockers. Nimodipine has effects on cerebral blood vessels. It selectively dilates cerebral vessels but has only minor effects on peripheral circulation. It is useful in the treatment of cerebral arterial spasm following subarachnoid hemorrhage, migraine headache, acute ischemic stroke and severe head injury. It is also proposed for use in the present invention, similarly to nisoldipine, nicardipine and nifedipine.

Nimodipine (NIMOTOP™) is available in 30-mg capsules. The approved indication for its use is to improve neurological deficits due to vasospasm following subarachnoid hemorrhage from ruptured congenital intracranial aneurysms. The recommended dosage is 60 mg every 4 hours for 21 days, beginning within 96 hours of the hemorrhage.

I. Nitrendipine

Nitrendipine is 3,5-Pyridinedicarboxylic acid, 1,4-dihydro-2,6-dimethyl-4-(3-nitrophenyl)-, ethyl methyl ester; available as BAYPRESS™ from Miles.

Nitrendipine is approved for the treatment of mild to severe hypertension. It is metabolized extensively in the liver, and only 10 to 22% of an oral dose reaches the systemic circulation in young adults. The elimination half-life has been reported to range from 2 to 23 hr, 12 hr probably being an average value. Hepatic dysfunction greatly increases the half-life. The volume of distribution has been reported variously to be 2 to 6 L/kg. About 98% is bound to plasma proteins.

It is used in dosage forms of, for adults, initially 5 to 20 mg once a day in the morning, to be adjusted to twice this dose, if necessary. Nitrendipine is also proposed for use in the invention, by virtue of its similarity to the above calcium channel blockers.

EXAMPLE 22

Calmodulin Antagonists

Ford et al. (1990) indicated that thioxanthenes and phenothiazines have uses in inhibiting p-glycoprotein.

A. Flupenthixols

Phenothiazines have been shown to sensitize multidrug resistant (MDR) cells to chemotherapeutic drugs in a manner related to specific structural features. Ford et al. (1990) identified structurally related phenothiazines and thioxanthenes with increased anti-MDR activity. Any of the compounds in the Ford study are proposed for use in the present invention.

Ford et al. (1990) particularly showed that trans-flupenthixol, its stereoisomer cis-flupenthixol, its phenothiazine homologue fluphenazine, and the calcium channel blocker verapamil, reversed cellular resistance to various drugs only in p-glycoprotein expressing cell lines. trans-flupenthixol caused a greater reversal of cellular resistance to doxorubicin, vinblastine, vincristine, and colchicine, and was two- to three-fold more potent for reversing MDR than equimolar concentrations of verapamil. Furthermore, trans-flupenthixol fully reversed resistance to doxorubicin, vincristine, and colchicine.

The apparent lack of clinical toxicity of trans-flupenthixol makes it an attractive drug for possible use in the modulation of tumor resistance in vivo (Hait et al., 1993). The present inventors thus propose that trans-flupenthixol would be particularly effective for combination with camptothecins, as disclosed herein. Cis-flupenthixol and clorpenthixol are also contemplated for use.

B. Fluphenazine

In light of the studies of Ford et al. (1990), fluphenazine is proposed for use in the present invention. Fluphenazine hydrochloride, also termed PERMITIL™ and PROLIXIN™, is available from Schering-Plough and Squibb. It is a trifluoromethyl phenothiazine derivative intended for the management of manifestations of psychotic disorders. Although the pharmacological effects are, in general, similar to those of other phenothiazines, laboratory and clinical studies indicate that his drug exhibits several important differences. The drug is more potent, exhibits a more prolonged duration of action, is less likely to induce hypotension, is less sedative and does not potentiate CNS depressants and anesthetics to the same degree as other phenothiazines.

It is absorbed rapidly after oral or intramuscular administration, onset of action occurs within 1 hr, peak plasma levels in 1.5 to 2 hr and duration of action is 6 hr. The intramuscular or subcutaneous administration of the enanthate salt has an average duration of 2 wk.

It is used in oral doses of, adult, initially 0.5 to 10 mg a day in divided doses; maintenance, 1 to 5 mg as a single dose a day; intramuscular, 1.25 to 10 mg a day divided into 4 doses. Daily dosages exceeding 20 mg orally or 10 mg intramuscularly should be used with caution. It is available in elixir dosage forms of 1 mg/2 mL; concentrated, 5 mg/mL; injectable, 25 mg/10 mL; tablets, 1, 2.5, 5 and 10 mg.

Fluphenazine decanoate, also termed prolixin decanoate, is available from Princeton. It is a trifluoromethyl phenothiazine derivative indicated for the management of patients requiring prolonged parenteral neuroleptic therapy (eg, chronic schizophrenics). Peak plasma level usually is achieved in 1 to 2 2 days; half-life (after a single dose) is 6.8 to 9.6 days, onset of action is 1 to 3 days and duration of action is about 4 wk.

Useful doses are, intramuscular or subcutaneous, 12.5 to 100 mg; usually, 12.5 to 25 mg; subsequent injections and dosage interval are based with patient response. It is available in injectable dosage forms of 25 mg/mL vials and 1-mL Unimatic syringes.

Fluphenazine enanthate (prolixin enanthate) except for duration of action, it has actions, uses, contraindications, and untoward effects similar to those of the hydrochloride. The esterification of fluphenazine with the enanthate moiety markedly prolongs the drug's duration of action without unduly attenuating its beneficial effects. The onset of action generally appears between 24 to 72 hr after injection and the effects of the drug on psychotic symptoms become significant within 48 to 96 hr. Amelioration of symptoms continues for 1 to 3 wk or longer, with an average duration of effect of about 2 wk.

Suitable doses are, intramuscular or subcutaneous, 12.5 to 100 mg every 1 to 3 wk; usual, 12.5 to 25 mg; subsequent injections and dosage interval are based on patient response. It is available in injectable dosage forms 25 mg/mL in 5-mL vials.

C. Chlorpromazine

Akiyama et al. (1988) showed that chlorpromazine and trifluoperazine effectively reverse multidrug resistance, most probably by binding to p-glycoprotein. However, these agents were poor inhibitors of the photoaffinity labeling of p-glycoprotein. This suggests that although most agents that phenotypically suppress multidrug resistance also inhibit photoaffinity labeling of p-glycoprotein, some may not have this property. Binding and inhibition of p-glycoprotein may thus occur at distinct sites on the molecule. This is also supported by monoclonal antibody data.

Chlorpromazine hydrochloride is 10H-Phenothiazine-10-propanamine, 2-chloro-N,N-dimethyl-, mono hydrochloride. It was the first tranquilizer of the phenothiazine group of compounds and is effective in the management of manifestations of psychotic disorders, nausea and vomiting, manifestations of manic depressive illness (manic phase), intractable hiccups, apprehension and anxiety prior to surgery, acute intermittent porphyria and as an adjunct in the treatment of tetanus. The volume of distribution has been reported to be 21.8 L/kg after intramuscular administration and 80.6 L/kg after a single oral dose. This 4-fold difference reflects the low bioavailability via the route (32%).

Dosage is variable and requires strict individualization. Administration is oral, intramuscular, or intravenous. Parenteral administration should be reserved for bedfast or hospitalized patients. If used in ambulatory patients, the patient must remain in a supine position for at least 1 hr after the injection.

Appropriate doses are, as an antiemetic, adults, oral, 10 to 25 mg every 4 to 6 hr.; intramuscular, 25 to 50 mg every 3 ro 4 hr until vomiting ceases. Children, oral, 0.5 mg/kg every 4 to 6 hr; intramuscular, 0.5 mg/kg every 6 to 8 hr as required. Tranquilizer, adults, oral usual, 10 to 50 mg 2 or 3 times a day to a total dose of 1 g a day when indicated; intramuscular, 25 to 50 mg, repeated in 1 hr if necessary to a total dose of 1 g a day when indicated. Children, oral, 0.5 mg/kg every 4 to 6 hr; intramuscular, 0.5 mg/kg every 6 to 8 hr as required.

It is available in injectable dosage forms of 25 mg/mL in 1,2 and 10 mL; timed-release capsules of 30, 75, 150, 200 and 300 mg; syrup of 2 mg/mL; concentrate of 30 and 100 mg/mL; and tablets of 10, 25, 50, 100 and 200 mg.

Chlorpromazine, also termed THORAZINE™, is available from SmithKline. Doses are, as an antiemetic used rectally, 50 to 100 mg every 6 to 8 h. Dose range, 50 to 400 mg. Pediatric, antiemetic, children 6 mo and older, 1 mg per kg or i of a 25 mg suppository 3 or 4 times a day as necessary; children under 6 mo not recommended. It is available in suppository dosage forms of 25 and 100 mg. Clomipramine may also be used in a similar manner.

D. Triflupromazine

Triflupromazine hydrochloride is 10H-Phenothiazine-10-propanamine, N,N-dimethyl-2-(trifluoromethyl)-monohydrochloride; also termed VERSPRIN HYDROCHLORIDE™ and available from Squibb. It is the 2-(tribluoromethyl) analogue of chlorpromazine hydrochloride and is indicated for the management of psychotic disorders (excluding psychotic depressive reactions) and for the control of severe nausea and vomiting.

Except that this drug is somewhat more potent, it has the same actions and limitations as chlorpromazine. In light of the studies of Akiyama et al. (1988), triflupromazine is also proposed for use in the p-glycoprotein inhibition aspects of the present invention.

Suitable doses are, for psychotic disorders, usual, adult, intramuscular, initially 60 to 150 mg in divided doses; intravenous, 1 mg, up to a 3-mg total daily dose. Children, intramuscular, 0.2 to 2.5 mg/kg a day; not to exceed 10 mg a day. Nausea and vomiting, usual, adult, intramuscular, 5 to 15 mg as a single dose; may be repeated every 4 hr but not to exceed 60 mg/day. Elderly or debilitated patients, intramuscular, 2.5 mg, not to exceed 15 mg/day. Children, 2½ yr and older, intramuscular, 0.2 to 0.25 mg/kg a day in divided doses, not to exceed 10 mg a day. It is available in injectable dosage forms of 10- and 20-mg/mL in multiple-dose vials; and in tablets of 10, 25 and 50 mg.

E. Trifluoperazine

Trifluoperazine reverses multidrug resistance without inhibiting photoaffinity labeling of p-glycoprotein (Akiyama et al., 1988).

Trifluoperazine is 10H-Phenothiazine, 10-[3-(4-methyl-1-piperazinyl)propyl]-2-(trifluoromethyl)-, dihydrochloride; also termed STELAZINE™ (SKF) and SUPRAZINE™ (Mayor). It is a piperazine phenothiazine effective in the management of the manifestations of psychotic disorders. It is possibly effective for the control of excessive anxiety, tension and agitation seen in neurosis or associated with somatic conditions. The general profile of pharmacological action is similar to other phenothiazine derivatives. Bioavailability, time to peak effect, metabolism and elimination half-life resemble those for chlorpromazine. Untoward effects such as hypotension, blurred vision and other manifestations of autonomic blockade appear to be less troublesome than with other phenothiazines.

Suitable doses are: oral, non-hospitalized patients, 1 to 2 mg twice a day; hospitalized patients, 2 to 5 mg twice a day initially, gradually increasing to the optimum level of 15 to 20 mg a day, although a few patients may require 40 mg a day or more; intramuscular, 1 to 2 mg every 4 to 6 hr as required. Elderly patients, lower doses are usually sufficient; the elderly are more susceptible to hypotension and neuromuscular reactions, observe closely and increase dosage gradually. Nonpsychotic anxiety, 1 to 2 mg twice a day; maximum, 6 mg/day, not to exceed 12 wk. (Doses stated in base equivalents.) Usual, pediatric, oral, hospitalized children 6 to 12 yr, 1 mg once or twice a day, dosage gradually increased until symptoms controlled; maximum, 15 mg a day. It is available in injectable dosage forms of (base equivalent) 20 mg/10 mL; concentrate, 10 mg/mL; tablets, 1, 2, 5 and 10 mg.

F. Prochlorperazine

Prochlorperazine maleate is used as an antiemetic, antipsychotic and tranquilizing agent. It is an effective antiemetic in the control of mild or severe nausea and vomiting due to a variety of causes, such as early pregnancy, anesthesia and surgery and radiation therapy. The drug is also an effective antipsychotic and is used in severe psychiatric disorders such as schizophrenia, mania, involutional psychoses, degenerative conditions and senile and toxic psychoses. As a tranquilizing agent, it is possibly effective in mild mental disorders in which anxiety, tension and agitation predominate.

In light of the studies of Ford et al. (1990) and Akiyama et al. (1988), prochlorperazine is envisioned for use with camptothecins in the present invention.

Appropriate doses are (as base equivalent), in adults, oral, antiemetic, 5 to 10 mg 3 or 4 times a day as required; tranquilizer, 5 to 35 mg 3 or 4 times a day, the initial low dose being increased gradually until the desired response is obtained, for which 50 to 150 mg daily usually is required. It is available in tablet dosage forms of (base equivalent): 5, 10 and 25 mg; Sustained Release Capsules: 10, 15, 30 and 75 mg from Major and Smith Kline & French.

Prochlorperazine, as the base, is also administered rectally at doses of, for children, 2.5 to 10 mg a day, according to weight, in divided doses; adults, 25 mg 2 times a day. The Child's rectal dose should not exceed 7.5, 10 and 15 mg a day for a 20- to 29-lb, 30- to 39-lb and 40- to 58-lb children, respectively. It is not recommended for children weighing less than 20 lb. It is available in suppository dosage forms of 2.5, 5, 10 and 25 mg.

Prochlorperazine edisylate is also available for use as prochlorperazine maleate, except that it may be administered intramuscularly as well as orally. Parenteral therapy usually is reserved for the treatment of severe nausea and vomiting, for the immediate control of acutely disturbed psychotics or for patients who cannot or will not take oral medication.

It is given in oral dosage forms of (as base equivalent), antiemetic, 5 to 10 mg 3 or 4 times a day as required; tranquilizer, 5 to 35 mg 3 or 4 times a day. Usual range of oral dose, 5 to 150 mg daily. Intramuscular or intravenous, antiemetic, 5 to 10 mg 6 to 8 times a day as required; tranquilizer, 10 to 20 mg 4 to 6 times a day as required. Usual range of parenteral dose, as antiemetic, 5 to 40 mg daily; as tranquilizer, 10 to 200 mg daily. No more than 40 mg of base equivalent should be injected in any 24-hr period unless the patient is hospitalized and under adequate observation. For acutely disturbed patients, the usual dose is 20 to 40 mg intramuscularly at intervals of 1 to 6 hr. It is available in injectable dosage forms of (base equivalent) 5 mg/mL; syrup forms of 5 mg/5 mL; and concentrate (for institutional use): 10 mg/mL.

G. Thioridazine

Thioridazine is 10H-Phenothiazine, 10-[2-(1-methyl-2-piperidinyl)ethyl]-2-(methylthio)-, also termed MELLARIL-S™ and available from Sandoz. It is a piperidyl-type phenothiazine tranquilizer with central sedative and behavioral effects similar to those of chlorpromazine. Half-life appears to be multiphasic with an early phase of 4 to 10 hr and a late phase of 26 to 36 hr; 96 to 99% is bound to plasma protein. As thioridazine has similar effects to chlorpromazine, it is considered to be suitable for use in binding to and inhibiting p-glycoprotein in accordance with the present invention.

Suitable doses are, adult, usual, initially 25 to 100 mg three times a day; maintenance, 10 to 200 mg 2 to 4 times a day. For the management of agitation, anxiety, depressed mood, tension, sleep disturbances and fears in geriatric patients, usual, oral 25 mg 3 times a day. Total daily dose ranges from 200 to 800 mg, divided into two to four doses. Usual, pediatric, children 2 to 12 yr, 0.5 to a maximum of 30 mg/kg/day, dosage increased daily until optimum therapeutic effect obtained or the maximum dose reached. It is available in concentrated dosage forms of 30 and 100 mg/mL; as a suspension of 25 and 100 mg/5 mL; or as tablets of 10, 15, 25, 50, 100, 150 and 200 mg.

EXAMPLE 23

Steroids

A. Progesterone and Metabolites

Ichikawa-Haraguchi et al. (1993) identified progesterone and its metabolites as potent inhibitors of the transporting activity of p-glycoprotein in the adrenal gland. These authors reported that progesterone and pregnenolone inhibited the transporting activity of p-glycoprotein. Sixauthentic progesterone metabolites in the 5 beta-metabolic pathway were also able to inhibit p-glycoprotein. Stereoisomerism around carbon 5 of the progesterone metabolites is important for them to be recognized by p-glycoprotein. Progesterone and pregnenolone analogues of the correct stereoisomerism are thus proposed for use in the present invention.

B. RU 486

Gruol et al. (1994) also reported that progesterone binds p-glycoprotein s and inhibits their drug efflux. They further reported that the antiprogestin, RU 486, reverses multidrug resistance in cells with p-glycoprotein. In measuring the inhibition of p-glycoprotein-dependent drug efflux, RU 486 was found to be considerably more effective than progesterone and one-half as effective as verapamil. RU 486 is thus also proposed for use herewith.

C. Tirilazad

Non-glucocorticoid steroid analogues (21-aminosteroids) also sensitize multidrug resistant cells to vinblastine by inhibiting p-glycoprotein (Abraham et al., 19932). These 21-aminosteroid derivatives, also termed lazaroids, include te potent inhibitors tirilazad mesylate (tirilazad, U-74006F) and U-74389F. Tirilazad sensitizes resistant cells to killing by vinblastine by 66-fold, but does not change the sensitivity of nonresistant parental cells. Tirilazad inhibits the photoaffinity labeling of p-glycoprotein, more effectively than does verapamil. Studies suggest that the complexamine portion of tirilazad is important for its reversal activity, while the steroid portion is less important. Therefore, tirilazad and other structurally related compounds, e.g., those developed to treat stroke and trauma of the central nervous system are envisioned to be useful in the present invention.

EXAMPLE 24

Antineoplastic Agents

A. Vincristine

Shirai et al. (1991) reported that p-glycoprotein is inhibited by vincristine. These authors also reported that p-glycoprotein is involved in the complexfunction of the blood-brain barrier as a secretory detoxifying transporter. Akiyama et al. (1989) also identified vincristine as a p-glycoprotein inhibitor.

Friche et al. (1993) showed that 10 µM vincristine inhibited p-glycoprotein by 95% and was more potent than anthracycline analogues also tested. Using anti-p-glycoprotein MAbs, Mechetner & Roninson (1992) established that vincristine as a p-glycoprotein inhibitor.

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppresive agents.

Unpredictable absorption has been reported after oral administration of vinblastine or vincristine. At the usual clinical doses the peak concentration of each drug in plasma is approximately 0.4 µM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 µM).

Vincristine sulfate (ONCOVIN™, Lilly, VINCASAR™, Adria) is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Maintenance therapy with vincristine is not recommended in children with leukemia. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine is effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

B. Vinblastine

McKinney & Hosford (1993) reported that vinblastine, actinomycin D and colchicine were all inhibitors of p-glycoprotein-mediated transport, as shown using studies in a model of renal tubules. Kamiwatari et al. (1989) and Akiyama et al. (1989) also identified vinblastine as a p-glycoprotein inhibitor.

Using mice homozygous for a disruption of the p-glycoprotein gene, Schinkel et al. (1994) showed that vinblastine normally interacted with p-glycoprotein. Using anti-p-glycoprotein MAbs, Mechetner & Roninson (1992) also established that drugs vinblastine interacted with p-glycoprotein.

Bear (1994) also proposed that vinblastine blocked certain p-glycoprotein activity and Morris et al. (1991) identified vinblastine as a p-glycoprotein inhibitor.

When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 µM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 µM).

Vinblastine sulfate (VELBAN™) is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

C. Actinomycin D

McKinney & Hosford (1993) reported that actinomycin D was an inhibitor of p-glycoprotein, as did Mechetner & Roninson (1992) and Akiyama et al. (1989).

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 µg/kg; this is given intravenously for 5 days; if no manifestations of toxicity are encountered, additional courses may be given at intervals of 3 to 4 weeks. Daily injections of 100 to 400 µg have been given to children for 10 to 14 days; in other regimens, 3 to 6 µg/kg, for a total of 125 µg/kg, and weekly maintenance doses of 7.5 µg/kg have been used. Although it is safer to administer the drug into the tubing of an intravenous infusion, direct intravenous injections have been given, with the precaution of discarding the needle used to withdraw the drug from the vial in order to avoid subcutaneous reaction.

D. Colchicine

Bear (1994) showed that vinblastine blocked an outwardly-rectifying chloride channel that was proposed to be associated with p-glycoprotein expression.

Morris et al. (1991) also identified colchicine as inhibiting p-glycoprotein , along with cytochalasin B. The antibody studies of Mechetner & Roninson (1992) and Akiyama et al. (1989) also established colchicine as binding to p-glycoprotein.

Colchicine is the agent of choice in the symptomatic treatment of acute attacks of gouty arthritis. When properly used, it will usually terminate an attack in 24 to 48 hr. The drug is well-absorbed after oral administration; 31% is bound to plasma protein. It is toxic, and should be discontinued at the first evidence of toxicity, namely, diarrhea, nausea, vomiting and abdominal pain.

Appropriate doses are usual, adult, prophylactic, mild gout, 0.5 to 0.6 mg once a day for 1 to 4 days each week; moderate to severe gout, 0.3 to 0.6 mg 1 to 3 times a day. Therapeutic, oral, 0.5 to 1.2 mg initially, followed by 0.5 to 1.2 mg every 2 hr until pain is relieved or until nausea, vomiting or diarrhea occurs. Total accumulative dose ranges from 4 to 8 mg. Intravenous, acute attacks of gout, initially 2 mg, followed by 0.5 mg every 6 hr until a satisfactory response is achieved. The total intravenous dose for one course of treatment generally should not exceed 4 mg; subcutaneous extravasation may be painful. It is available in tablet dosage forms of 0.5 and 0.6 mg; and as an injectable of 1 mg/2 mL.

E. Etoposide

Using anti-p-glycoprotein MAbs, Mechetner & Roninson (1992) established that the drugs, etoposide and puromycin interacted with p-glycoprotein.

Oral administration of etoposide results in absorption of about 50% of the drug. After intravenous injection, peak plasma concentrations of 30 µg/ml are achieved; there is a biphasic pattern of clearance, with a terminal half-life of about 8 hours in patients with normal renal function. Approximately 40% of an administered dose of etoposide is excreted as such in the urine. Dosage should be reduced in proportion to reductions in creatinine clearance. Concentrations of etoposide in CSF range from 1 to 10% of the simultaneous value in plasma.

Etoposide (VEPESID™) is available as a solution (20 mg/ml) for intravenous administration and as 50-mg, liquid-filled capsules for oral use. The intravenous dose for testicular cancer (in combination therapy) is 50 to 100 mg/M$^2$ daily for 5 days, or 100 mg/m$^2$ on alternate days, for three doses. For small-cell carcinoma of the lung, the intravenous dose (in combination therapy) is 35 mg/m$^2$, daily for 4 days, to 50 mg/m$^2$, daily for 5 days. When given orally, the dose should be doubled. Cycles of therapy are usually repeated every 3 to 4 weeks. The drug should be administered slowly during a 30- to 60-minute infusion in order to avoid hypotension and bronchospasm, which are probably due to the solvents used in the formulation.

Etoposide is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

F. Daunomycin

Bear (1994) showed that daunomycin, vinblastine, colchicine and verapamil (at 50 µM) blocked a transport function believed to be associated with p-glycoprotein expression. Akiyama et al. (1989) also identified daunomycin as a p-glycoprotein inhibitor. Daunomycin is contemplated for use in the present invention similarly to daunorubicin.

G. Daunorubicin

Daunorubicin, in addition to verapamil and quinidine, was shown to inhibit the ATP-dependent transport of amphiphilic cations across the hepatocyte canalicular membrane by p-glycoprotein (Muller et al., 1994).

Daunorubicin hydrochloride, 5,12-Naphthacenedione, (8S-cis)-8-acetyl-10-[(3-amino-2,3,6-trideoxy-α-L-lyxo-hexanopyranosyl)oxy]-7,8,9,10-tetrahydro-6,8,11-trihydroxy-10-methoxy-, hydrochloride; also termed CERUBIDINE™ and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 min and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr 45 mg/m$^2$/day (30 mg/r$^2$ for patients older than 60 yr) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/r$^2$ once a week unless the age is less than 2 yr or the body surface less than 0.5 m, in which case the weight-based adult schedule is used. It is available in injectable dosage forms (base equivalent) 20 mg (as the base equivalent to 21.4 mg of the hydrochloride).

H. Doxorubicin

Using anti-p-glycoprotein MAbs, Mechetner & Roninson (1992) established that doxorubicin interacted with p-glycoprotein.

Doxorubicin hydrochloride, 5,12-Naphthacenedione, (8s-cis)-10-[(3-amino-2,3,6-trideoxy-α-L-lyxo-hexopyranosyl)

oxy)-7,8,9,10-tetrahydro-6,8,11-trihydroxy-8-(hydroxyacetyl)-1-methoxy-hydrochloride (hydroxydaunorubicin hydrochloride, ADRIAMYCIN™) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 min and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/i$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/x$^2$ in patients with normal heart function and 400 mg/r$^2$ in persons having received mediastinal irradiation. Children, 30 mg/m$^2$ on each of 3 consecutive days, repeated every 4 wk. Prescribing limits are as with adults.

I. Taxotere

Taxotere, in addition to 1,9-dideoxyforskolina and nifedipine were shown to be p-glycoprotein inhibitors by Hunter et al. (1993).

J. Taxol

Using anti-p-glycoprotein MAbs, Mechetner & Roninson (1992) showed that taxol interacted with p-glycoprotein.

Taxol is an experimental antimitotic agent, isolated from the bark of the ash tree, Taxus brevifolia. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$_2$ given once every 3 weeks.

K. Tamoxifen

In analyzing p-glycoprotein drug efflux, Trump et al. (1992) reported that the triphenylethylene antiestrogen, tamoxifen, and its major metabolite, N-desmethyltamoxifen, enhanced the intracellular concentration of cytotoxic drugs three-fold to ten-fold in a variety of human and murine cell lines at concentrations of 4–6 µM.

In a phase I clinical trial of high-dose, oral tamoxifen Trump et al. (1992) also reported that tamoxifen at 150 mg/m2 given twice a day following a loading dose of 400 mg/m2 results in plasma levels of tamoxifen and N-desmethyltamoxifen of 4 and 6 microM, respectively, without dose-limiting toxicity. This dose was recommended for phase II trials of tamoxifen to modulate p-glycoprotein-mediated drug resistance even though tamoxifen did not enhance the toxicity of vinblastine, the object of the study. Nonetheless, the showing that high-dose tamoxifen can be safely administered and that plasma concentrations that may inhibit p-glycoprotein function can be achieved is relevant to the present invention, allowing tamoxifen to be used in conjunction with camptothecins.

Tamoxifen is available as tamoxifen citrate (ethanamine, 2-[4–1,2-diphenyl-1-butenyl)phenoxy]-N,N-dimethyl-, (Z)-), also termed NOLVADEX™ available from Stuart. It is used as a nonsteroidal antiestrogen for palliative therapy of breast cancer in postmenopausal women. The drug competes with estrogens for cytosol estrogen receptors and thus blocks estrogen effects in the target tissue. The oral bioavailability is 25 to 100%. The half-life of a single dose is 18 hr, but it is only 7 hr at steady state.

It is used at oral doses, for breast cancer, of 10 or 20 mg, twice a day; for stimulation ovulation, 5 to 40 mg twice a day for 4 days; for mastalgia, 10 mg a day for 4 mo. It is available in tablet dosage forms of 10 mg.

EXAMPLE 25

Cationic Compounds

A. Reserpine

In studying digoxin transport by p-glycoprotein, Hori et al. (1993) showed that reserpine inhibited this process. Akiyama et al. (1988) and Miyamoto et al. (1992b) also showed that reserpine binds to p-glycoprotein and inhibits photo-labeling.

Reserpine is Yohimban-16-carboxylic acid, 11,17-dimethoxy-18-[(3,4,5-trimethoxybenzoyl)oxy]-, methyl ester, (3β,16β,17α,18β,20α)-. It is used as a tranquilizer and as an antihypertensive agent. Because the hypotensive doses used are generally considerably smaller than those for its tranquilizing effects, reserpine is used for its hypotensive effects with more safety than as a psychopharmacological drug. It exerts its antihypertensive effects through a partial depletion of the norepinephrine in the sympathetic postganglionic nerves. Intravenously, it is quite useful in the management of severe hypertension and hypertensive crises.

The drug is absorbed poorly and erratically from the gastrointestinal tract, which causes a considerable difference in efficacy of oral vs. intravenous doses. It characteristically has a long latency of onset and a prolonged duration of action. for example, with daily oral administration the effects of the drug usually are not fully manifest for several days to 2 weeks and may persist for as long as 4 weeks after oral medication is discontinued. Tolerance to the drug does not develop with continued administration.

Suitable doses are, oral, adults, for hypertension, initially 0.05 to 0.2 mg a day in 1 or 2 divided doses; when higher doses are used, the patient must be monitored continuously for mood depression, for anxiety-tension, initially 0.1 to 0.5 mg a day for control, then adjusted to minimum effective dose; for psychotic disorders, initially 0.1 to 1 mg a day, with subsequent adjustments to maintain control; children (not recommended), for hypertension, 5 to 20 ug/kg (or 150 to 600 ug/m$^2$) a day, once or in 2 divided doses. It is available in extended-release capsules of 0.5 mg; and as tablets of 0.1, 0.25 and 1 mg.

B. Dipyridamole

Tatsuta et al. (1991) showed that the activities of antitumor drugs against multidrug-resistant human hepatoma cells is enhanced by dipyridamole. Dipyridamole (DPM), at 10 μM enhanced the cytotoxicity of anti-tumor drugs, and increased dose-dependently the intracellular accumulation of vinblastine. It was concluded that DPM binds to p-glycoprotein and inhibits active drug efflux. Suzuki et al. (1990) also reported dipyridamole to be a p-glycoprotein inhibitor.

Dipyridamole is [2,6-Bis(diethanolamino)-4,9-dipiperidinopyrimido-(5,4-d)pyrimidine [58-32-2] $C_{24}H_{40}N_8O_4$, which is available from Boehringer Ingelheim. It is used to inhibit phosphodiesterase, the synthesis of thromboxane $A_2$, the reuptake of adenosine and promotes the synthesis of prostacyclin in vascular smooth muscle. In coronary blood vessels, all of these actions favor coronary vasodilation. The drug is approved for adjunctive use with prothrombopenic anticoagulants in the postoperative prevention of thromboembolism in cardiac valve replacement. It also is used with aspirin or warfarin in coronary bypass surgery and with aspirin in transient ischemic attacks, after myocardial infarction and in deep vein thrombosis.

Suitable doses are, oral, adult, 75 to 100 mg 4 times a day. It is available in tablet dosage forms of 25, 50 and 75 mg. In the doses usually employed clinically, dipyridamole is quite nontoxic.

C. Chloroquine

Chloroquine partially reverses drug resistance in multidrug-resistant human carcinoma cells, and for this reason is contemplated for use in this invention (Akiyama et al., 1988). Chloroquine phosphate is 1,4-Pentanediamine, $N^4$-(7-chloro-4-quinolinyl)-$N^1$, $N^1$-diethyl-, phosphate (1:2); available from Biocraft, Danbury, and also termed ARALEN PHOSPHATE™, available from Winthrop.

It is used as an antimalarial drug and is the drug of choice for the oral treatment of all malaria except that caused by resistant P falciparum. Although not useful in intestinal amebiasis, it is an effective agent in the treatment of extraintestinal amebiasis, especially amebic hepatitis.

The drug is absorbed almost completely from the gastrointestinal tract and usually is administered orally. It (as the hydrochloride) is given intramuscularly when necessary to resort to parental administration. Tissues bind the drug, although not quite to the same degree of quinacrine. It is degraded in tissues to unknown products. The drug is slowly excreted in the urine with an initial half-life of 1 wk, changing to 17 days after 4 wk, then ultimately becoming months.

Appropriate doses are, oral, adults, for malaria, as a suppressive, 500 mg once a wk for 2 wk before exposure, and for therapy, initially 1 g followed by 500 mg in 6 to 8 hr, then 500 mg once a day on the 2nd and 3rd days; for extraintestinal amebiasis, 250 mg 4 times a day for 2 days followed by 250 mg twice a day for at least 2 or 3 wk; for lupus erythematosus, 250 mg twice a day for 2 wk then once a day thereafter; to suppress photoeruptions, 250 mg twice a day for 2 wk then once a day; for rheumatoid arthritis, 250 mg once a day, to be increased to as much as 750 mg a day, if necessary. Children, for malaria, as a suppressive, 8.3 mg/kg, not to exceed 500 mg, once a week, and for therapy, initially 16.7 mg/kg, not to exceed 1 g, then 8.3 mg/kg, not to exceed 00 mg, 6, 24 and 48 hr later; for extraintestinal amebiasis, 10 mg/kg, not to exceed 600 mg, every day for 3 wk.

Suppressive treatment should begin 2 wk in advance of entering into a malarious region and continue for 8 wk after departure; rapid loading for suppression can be achieved by giving the two weekly doses in a single day, 6 hr apart. It is available in tablets of 250 and 500 mg, equivalent to 150 and 300 mg, respectively, of chloroquine base.

Chloroquine hydrochloride is 1,4-Pentanediamine, $N^4$-(7-chloro-4-quinolinyl)-$N^1$, N-diethyl-, dihydrochloride; also termed ARALEN HYDROCHLORID™ available from Winthrop. Its actions and uses are those of chloroquine phosphate, except that the hydrochloride lends itself better to solutions for intramuscular injection. The intramuscular route may be indicated in patients who cannot tolerate oral chloroquine.

Suitable doses are intramuscular, adults, for malaria, 200 to 250 mg, to be repeated in 6 hr, if necessary, but not to exceed 1 g in the first 24 hr; for extraintestinal amebiasis, 200 to 250 mg once a day for 10 to 12 days. Children, for malaria, 6.25 mg/kg and no more, to be repeated in 6 hr, if necessary, but not to exceed 12 mg/kg in any 24-hr period; for extraintestinal amebiasis, 7.5 mg/kg a day for 10 to 12 days. It is available in injectable forms of 250 mg/5 mL, equivalent to 200 mg/5 mL of chloroquine base.

D. Propranolol

Propranolol is also proposed for use in the present invention based upon its ability to partially reverse drug resistance in multidrug-resistant human carcinoma cells (Akiyama et al., 1988).

Propranolol is a β-adrenergic antagonist used in the treatment of hypertension and angina. The initial oral dose of propranolol is generally 40 to 80 mg per day. The dose may then be titrated upward until the optimal response is obtained. For the treatment of angina, the dose may be increased at intervals of less than 1 week, as indicated clinically. In hypertension, the full response of the blood pressure may not develop for several weeks. Typically, doses are less than 320 mg per day. Propranolol may also be administered intravenously for the management of life-threatening arrhythmias.

Propranolol is highly lipophilic and is almost complete absorbed after oral administration. However, much of the drug is metabolized by the liver during its first passage through the portal circulation; on average, only about 25% reaches the systemic circulation. In addition, there is interindividual variation in the presystemic clearance of propranolol by the liver; this contributes to variability in plasma concentrations after oral administration of the drug (approximately 20-fold). The degree of hepatic extraction of propranolol declines as the dose is increased, and the bioavailability of propranolol may be increased by the ingestion of food and during long-term administration of the drug.

Propranolol has a large volume of distribution (4 liters/kg) and readily enters the CNS. Approximately 90% of the drug in the circulation is bound to plasma proteins. Propranolol is extensively metabolized, with most metabolites appearing in the urine.

A sustained-release formulation of propranolol has been developed to maintain therapeutic concentrations of propranolol is plasma throughout a 24-hour period. Suppression of exercise-induced tachycardia is maintained throughout the dosing interval, and patient compliance may be improved.

Propranolol hydrochloride is available in tablets that contain 10 to 90 mg of the drug for oral administration and at a concentration of 1 mg/ml for intravenous use. It is also available in sustained-release capsules (INDERAL™ Ayerst) that contain 80, 120, 10 160 mg.

EXAMPLE 26

Terfenadine (SELDANE™)

Terfenadine (SELDANE™) has been proposed as a drug for restoring sensitivity to multidrug resistant cancer cells (Hait et al., 1993). These authors tested terfenadine for p-glycoprotein binding because it appeared to sensitize a patient to doxorubicin and because it met structural requirements defined for this activity. The mechanism of action of terfenadine is believed to be due to inhibition of the function of p-glycoprotein since it augments the accumulation of doxorubicin and inhibits the effluxof rhodamine 123 from MDR lines but has no effect on drug accumulation or effluxin sensitive cells.

Since terfenadine is clinically available, has numerous structural derivatives available for study, and has a relatively low toxicity profile, this drug and drugs of its class are currently preferred for use in combination with camptothecins in the present invention.

Terfenadine is 1-Piperidinebutanol, α-[4-(1,1-dimethylethyl)phenyl]-4-(hydroxydiphenylmethyl)-, also termed SELDANE™, available from Merrell-Dow. Terfenadine is a peripheral distinct $H_1$-receptor antagonist, although chemically and pharmacologically distinct from other antihistamines. It is indicated for the relief of symptoms associated with seasonal allergic rhinitis such as sneezing, rhinorrhea, pruritus and lacrimation. It is absorbed rapidly and almost completely after oral administration; because of extensive first-pass metabolism, less than 1% reaches the systemic circulation unchanged and 97% of this is bound to plasma protein. Peak effect is observed within 1 to 2 hr; peak plasma levels range from 1.5 to 4.5 ng/mL. Plasma concentrations decline in a biphasic manner; distribution half-life is 3.5 hr and terminal elimination half-life is 16 to 23 hr.

Appropriate doses are, usual, adults and children over 12 yr, oral, 60 mg twice a day; children 6 to 12 yr, 30 to 60 mg twice a day; children 3 to 5 yr, 15 mg twice a day. It is available in tablet forms of 60 mg.

EXAMPLE 27

Ivermectin

Using mice homozygous for a disruption of the p-glycoprotein gene, Schinkel et al. (1994) conducted studies showing that such mice displayed an increased sensitivity to ivermectin. Therefore, ivermectin must normally interact with p-glycoprotein. Schinkel et al. (1994) proposed that p-glycoprotein inhibitors might be useful in selectively enhancing the access of a range of drugs to the brain.

The avermectins are a novel class of macrocyclic lactones. Ivermectin is a mixture of about 80% component $B_{1a}$ and 20% component $B_{1b}$, and is formed by selective catalytic hydrogenation of avermectin $B_1$. This semisynthetic agent is used extensively in veterinary medicine to treat and control a wide variety of infections caused by parasitic nematodes (roundworms) and arthropods (insects, ticks, and mites) that plague livestock and domestic animals.

In humans, ivermectin is now the drug of choice to treat and control onchocerciasis, the filarial infection responsible for river blindness. Ivermectin is effective and highly potent against at least some developmental stages of many parasitic nematodes that infect animal and man. Certain gastrointestinal nematodes that infect man are also susceptible to ivermectin. Thus, the drug appears highly effective in strongyloidiasis, ascariasis, trichuriasis, and enterobiasis; hookworms are also affected but to a lesser extent.

In humans, peak concentrations of ivermectin in plasma are achieved within 4 hours of oral administration; the half-life of the drug is about 10 hours. Animal studies reveal that only 1 to 2% of an orally administered dose of ivermectin appears in the urine; the remainder is found in the feces, nearly all as the unchanged drug.

Ivermectin is available from the Centers for Disease Control as MECTIZAN™ tablets, each containing 6 mg. Data indicate that a single oral dose of 0.15 to 0.20 mg/kg in adults causes a rapid and marked reduction of *O. volvulus* microfilaria in the skin and ocular tissues. This effect is noted within a few days and lasts for 6 to 12 months; the dose should then be repeated.

Single doses of ivermectin (0.15 to 0.20 mg/kg) given every 6 to 12 months are considered effective, safe, and practical for the control of onchocerciasis in man. Most important, such treatment results in reversal of lymphadenopathy and acute inflammatory changes in ocular tissues and arrests the development of further ocular pathology due to microfilariae. The finding that a single dose of 150 to 200 mg of ivermectin can cure human strongyloidiasis represents a significant advance, particularly because the drug is also effective against coexisting ascariasis, trichuriasis, and enterobiasis.

EXAMPLE 28

Quinidine

Akiyama et al. (1988) showed that quinidine binds to p-glycoprotein and inhibits photo-labeling. Hori et al. (1993) also showed that quinidine inhibited digoxin transport by p-glycoprotein. The ATP-dependent transport of amphiphilic cations across the hepatocyte canalicular membrane by p-glycoprotein was further shown to be inhibited by quinidine by Muller et al. (1994).

Quinidine Sulfate is Cinchonan-9-ol, 6'-methoxy, (9S)-, sulfate (2:1) (salt), dihydrate, It is a Class 1A antidysrhythmic drug that decreases automaticity, membrane responsiveness, excitability and conduction velocity. It is quite effective in suppressing chronic atrial premature contractions, and in converting and protecting against recurrences of atrial fibrillation.

Quinidine is 90% absorbed by the oral route. In plasma 82% is protein-bound. The volume of distribution is 0.47 mL/g. Therapeutic plasma levels range from 3 to 6 ug/mL is reached. Elimination is 50 to 60% by hepatic biotransformation. The half-life ranges from 3 to 17 hr, but usually is 5 to 7 hr. An alkaline urine favors tubular resorption and, hence, prolongs the half-life and elevates plasma levels. Adjustments in dosage must be made when drugs (many antacids, carbonic anhydrase inhibitors) or diets that increase urine pH are use.

Suitable doses are, oral, adults, conventional capsules, initially, premature atrial and ventricular depolarizations, 200 to 300 mg every 8 hr; paroxysmal supraventricular tachycardias, 400 to 600 mg every 2 to 3 hr until conversion; atrial flutter (only after digitalization), 200 mg, adjusted upward every 2 to 3 hr until conversion; 200 mg every 2 to 3 hr for 5 to 8 doses; all maintenance, 200 to 300 mg 3 or 4 times a day; sustained-release tablets, 300 to 600 mg every 8 to 12 hr, if necessary and when tolerated; infants and children, mg/kg (or 180 mg/m$^2$) 5 times a day. Parenteral administration is not recommended, although an injection is available.

Quinidine Gluconate is Cinchonan-9-ol,6'-methoxy-, (9S)-, mono-D gluconate (salt), also termed QUINAGLUTE™, available from Berlex, and DURAQUIN™, available from Parke-Davis. It has the same actions, uses and toxicity as quinidine sulfate, but is preferred for intramuscular use, since it is nonirritating and stable in solution. The intravenous administration of quinidine only is warranted occasionally, but sometimes is a lifesaving measure in certain desperate conditions such as ventricular tachycardia with acute pulmonary edema or severe congestive failure. The cardiac effect may be observed in 15 to 20 min after intramuscular injection. Hypotension is frequent. It can also be used for the treatment of malaria.

Appropriate doses are, oral, adults, as extended-release tablets, 324 to 660 mg, every 6 to 12 hr; the higher doses should be used only after a trial with lower doses and clinical and laboratory reexamination and determination of plasma quinidine levels. Intramuscular, adults, initially 600 mg, followed by 400 mg at intervals as short as every 2 hr, if necessary, up to a maximum daily dose of 5 g. Intravenous, adults, 200 to 800 mg in dilute solution (20 mg/mL in isotonic dextrose injection) given at a rate of no more than 1 mL/min (20 mg/min) with continuous monitoring of the electrocardiograph and blood pressure. It is available in injectable dosage forms of 800 mg/10 mL; and as extended-release tablets of 342 and 330 mg.

Quinidine polygalacturonate, also termed CARDIAQUIN™, is available from Purdue-Frederick. The actions, uses and general toxicity are those of quinidine sulfate, except that it is not used in attempted conversion of ventricular dysrhythmias and it causes a lesser incidence and severity of gastrointestinal side effects and hence is gaining preference for oral use.

Appropriate doses are oral, adults, initially 275 to 825 mg for 3 or 4 doses at 3- to 4-hr intervals, after which upward adjustments in increments of 137.5 to 275 mg may be made every third or fourth dose until the therapeutic end point is reached or toxicity supervenes, then 275 mg 2 or 3 times a day for maintenance; children, 8 to 25 mg/kg or 247.5 mg/m$^2$ 3 times a day according to need and tolerance. It is available in tablet dosage forms of 275 mg, equivalent to 200 mg of quinidine sulfate.

EXAMPLE 29

Monoclonal Antibodies

A. MRK16 and MH162

A first mouse-human chimeric antibody against p-glycoprotein was developed by Hamada et al. (1990) in an effort to devise an effective treatment for human drug-resistant cancers. The recombinant chimeric antibody has the antigen-recognizing variable regions of MRK16 joined with the constant regions of human antibodies. When human effector cells were used, the chimeric antibody, MH162, was more effective in killing drug-resistant tumor cells than the all-mouse monoclonal MRK16. As MRK16 inhibited the growth of human drug-resistant tumor cells in a xenograft model, the chimeric improvement should be even more useful in therapy.

B. MH171

A second mouse-human chimeric antibody, MH171, against p-glycoprotein was developed by Ariyoshi et al. (1992), in which antigen-recognizing variable regions of the mouse monoclonal antibody MRK17 are joined with the constant regions of human IgG1 antibodies. MRK17 specifically recognizes p-glycoprotein and inhibits the growth of human multidrug resistant (MDR) tumor cells in vitro and in the xenograft nude mouse model system.

MRK17, MH171, MRK16 and MH162 are envisioned for use as an effective second agent for treatment with camptothecins, particularly as success has been demonstrated for other applications in animal models.

C. UIC2

Mechetner & Roninson (1992) achieved efficient inhibition of p-glycoprotein using the MAb UIC2. UIC2 inhibited the efflux of p-glycoprotein substrates from MDR cells and significantly increased the cytotoxicity of p-glycoprotein-transported drugs. Potentiation of cytotoxicity by UIC2 was observed with the drugs vinblastine, vincristine, colchicine, taxol, doxorubicin, etoposide, actinomycin D, puromycin and gramicidin D, but not with any of the drugs to which MDR cells are not cross-resistant (methotrexate, 5-fluorouracil, cis-platinum, G418, and gentamicin).

The inhibitory effect of UIC2 in vitro was as strong as that of verapamil at its highest clinically achievable concentrations. UIC2 and its derivatives are thus proposed for use in the present invention.

D. Further MAbs

Schinkel et al. (1993) described the binding properties of MAbs that recognize external epitopes of human p-glycoprotein. Such antibodies may be used as specific inhibitors of p-glycoprotein-mediated multidrug resistance. Schinkel et al. (1993) particularly describe the MAbs MRK16, HYB-241, UIC2, 7G4 and 4E3, and one of which may be used to inhibit p-glycoprotein in combination with camptothecins.

Miyamoto et al. (1992b) developed the MAb C219 and Miller et al. (1991) developed the MAb JSB-1, both of which may be used to inhibit p-glycoprotein as disclosed herein.

EXAMPLE 30

Pharmaceutical Compositions

Aqueous compositions of the present invention will have an effective amount of CPT-11 and an effective amount of a compound (second agent) that increases conjugative enzyme activity, as represented by a compound that increases the activity of the phase II conjugative enzyme, glucuronosyl-transferase. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalents and the like.

A. Parenteral Administration

The active compounds will often be formulated for parenteral administration, e.g., formulated for injection via the intravenous, intramuscular, sub-cutaneous, or even intra-peritoneal routes. The preparation of an aqueous composition that contains CPT-11 and a second agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples. * * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abigerges et. al., "Phase I and pharmacologic studies of the camptothecin analog irinotecan administered every 3 weeks in cancer patients," *J Clin Oncol*, 13(1):210–221, 1995.

Abraham et al., "Non-glucocorticoid steroid analogues (21-aminosteroids) sensitize multidrug resistant cells to vinblastine," *Cancer Chemother. Pharmacol.*, 32(2):116–122, 1993.

Akiyama et al., "Most drugs that reverse multidrug resistance also inhibit photoaffinity labeling of P-glycoprotein by a vinblastine analog," *Mol. Pharmacol.*, 33(2):144–147, 1988.

Ansher et al., "Chemoprotective effects of two dithiolthiones and of butylhydroxyanisole against carbon tetrachloride and acetaminophen toxicity," *Hepatology*, 3(6):932–935, 1983.

Araki et al., "Relationship between development of diarrhea and the concentration of SN-38, an active metabolite of CPT-11, in the intestine and the blood plasma of athymic mice following intraperitoneal administration of CPT-11, "*Jpn. J. Cancer Res.*, 84:697–702, 1993.

Ariyoshi et al., "Mouse-human chimeric antibody MH171 against the multidrug transporter P-glycoprotein," *Jpn. J. Cancer Res.*, 83(5):515–521, 1992.

Atsumi et al., "Identification of the metabolites of irinotecan, a new derivative of camptothecin, in rat bile and its biliary excretion," *Xenobiotica*, 21:1159–1169, 1991.

Barilero et al., "Simultaneous determination of the camptothecin analogue CPT-11 and its active metabolite SN-38 by high-performance liquid chromatography: application to plasma pharmacokinetic studies in cancer patients," *J. Chrom.*, 575:275–280, 1992.

Bear, "Drugs transported by P-glycoprotein inhibit a 40 pS outwardly rectifying chloride channel," *Biochem. Biophys. Res. Commun.*, 200(1):513–521, 1994.

Bell et al., "Roles of peptidyl-prolyl cis-trans isomerase and calcineurin in the mechanisms of antimalarial action of cyclosporin A, FK506, and rapamycin," *Biochem. Pharmacol.*, 48(3):495–503, 1994.

Bock et. al., In: *Conjugation reactions in biotransformation*, Elsevier, North Holland Biomedical Press, p. 357–364, 1978.

Bock et al., "Purification of rat-liver microsomal UDP-glucuronosyltransferase: Separation of two enzyme forms inducible by 3-methylcholanthrene or phenobarbital," *Eur. J. Biochem.*, 98:19–26, 1979.

Boesch et al., "Restoration of daunomycin retention in multidrug-resistant P388 cells by submicromolar concentrations of SDZ PSC 833, a nonimmunosuppressive cyclosporin derivative," *Exp. Cell. Res.*, 196(1):26–32, 1991.

Boesch & Loor, "Extent and persistence of P-glycoprotein inhibition in multidrug-resistant P388 cells after exposure to resistance-modifying agents," *Anticancer Drugs*, 5(2):229–238, 1994.

Boiteux-Antoine et al., "Comparative induction of drug-metabolizing enzymes by hypolipidemic compounds," *Gen-Pharmacol*, 20(4):407–412, 1989.

Borrel et al., "Mobile ionophores are a novel class of P-glycoprotein inhibitors: The effects of ionophores on 4'-O-tetrahydropyranyl-adriamycin incorporation in K562 drug-resistant cells," *Eur. J. Biochem.*, 223(1):125–133, 1994.

Burchell & Coughtrie, "UDP-glucuronosyltransferases," *Pharmac. Ther.*, 43:261–289, 1989.

Burger et al., "Pharmacokinetic interaction between rifampin and zidovudine," *Antimicromal Agents and Chemotherapy*, 37(7):1426–1431, 1993.

Burris & Fields, "Topoisomerase I inhibitors: An overview of the camptothecin analogs," *Hematol Oncol Clin North Am*, 8(2):333–355, 1994.

Burris et al., "Activity of topotecan, an new topisomerase I inhibitor, against human tumor colony-forming units in vitro," *J. Natl. Cancer Inst.*, 84:1816–1819, 1992.

Campain et al., "Characterization of an unusual mutant of human melanoma cells resistant to anticancer drugs that inhibit topoisomerase II," *J. Cell Physiol.*, 155(2):414–425, 1993.

Chabot et al., *J Chromatogr*, 575:275, 1992

Charuk et al., "Interaction of rat kidney P-glycoprotein with a urinary component and various drugs including cyclosporin," *A. Am. J. Physiol.*, 35:F66-F75, 1994.

Chin et al., "Reduced mRNA levels for the multidrug-resistance genes in cAMP-dependent protein kinase mutant cell lines," *J. Cell Physiol.*, 152(1):87–94, 1992.

D'Arpa & Liu, "Topoisomerase-targeting antitumor drugs," *Biochim et. Biophys. Acta*, 989:163–177, 1989.

Davies & Schnell, "Oltipraz-induced amelioration of acetaminophen hepatotoxicity on hamsters," *Toxicology and Applied Pharmacology*, 109:39–40, 1991.

De Morais et al., "Biotransformation and toxicity of acetaminophen in congenic rha rats with or without a hereditary deficiency in bilirubin udp-glucuronosyltransferase," *Toxicology and Applied Pharmacology*, 117:81–87, 1992.

De Morais & Wells, "Enhanced acetaminophen toxicity in rats with bilirubin glucuronyl transferase deficiency," *Hepatology*, 10:163–167, 1989.

Doige et al., "ATPase activity of partially purified P-glycoprotein from multidrug-resistant Chinese hamster ovary cells," *Biochim. Biophys. Acta.*, 1109(2):149–160, 1992.

Egner et al., "Regulation of phase 2 enzyme induction by oltipraz and other dithiolethiones," *Carcinogenesis*, 15(2):177–181, 1994.

Ejima et. al., "Antitumor agents, V. Synthesis and antileukemic activity of E-ring-modified (RS)-camptothecin analogues," *Chem Pharm Bull*, 40(3):683–688, 1992.

Emerson et. al., "In vivo antitumor activity of two new seven-substituted water-soluble camptothecin analogues," *Cancer Res.* 55(3):603–609, 1995.

Endicott & Ling, "The biochemistry of P-glycoprotein-mediated multidrug resistance," *Annus Re. Biochem.*, 58:137–171, 1989.

Ford et al., "Cellular and biochemical characterization of thioxanthenes for reversal of multidrug resistance in human and murine cell lines," *Cancer Res.*, 50(6):1748–1756, 1990.

Fournel et al., "Structure-dependent induction of bilirubin glucuronidation and lauric acid 12-hydroxylation by arylcarboxylic acids chemically related to clofibrate," *Biochimica at Biophysica Acta,* 842:202–213, 1985.

Foxwell et al., "Identification of the multidrug resistance-related P-glycoprotein as a cyclosporine binding protein, "*Mol. Pharmacol.*, 36:543–546, 1989.

Friche et. al., *Biochem. Pharmacol.*, 39, 1721–1726; 1990

Friche et al., "Effect of anthracycline analogs on photolabelling of p-glycoprotein by [125I]iodomycin and [3H] azidopine: relation to lipophilicity and inhibition of daunorubicin transport in multidrug resistant cells," Br. *J. Cancer,* 67(2):226–231, 1993.

Friedman et al., "Activity of 9-dimethylaminomethyl-10-hydroxycamptothecin against pediatric and adult central nervous system tumorxenografts," *Cancer Chemother. Pharmacol.,* 34:171–174, 1994.

Furuta et al., "Antitumor activity of CPT-11 against rat Walker 256 carcinoma," Jpn. *J. Cancer Chemother.*, 15:2757–2760, 1988.

Giovanella et al., "DNA topoisomerase I-targeted chemotherapy of human colon cancer inxenografts," *Science,* 246:1046–1048, 1989.

Giovanella et al., "Complete growth inhibition of human cancer xenografts in nude mice by treatment with 20-S-camptothecin," *Cancer Res.*, 51:3052–3055, 1991.

Gottlieb et al., "Preliminary pharmacologic and clinical evaluation of camptothecin sodium 9NSC 100880)," *Cancer Chemother. Rep.*, 54:461–470, 1970.

Gruol et al., "Reversal of multidrug resistance by RU 486," *Cancer Res.*, 54(12):3088–3091, 1994.

Gupta et al., "Role of carboxyl esterase in the metabolism of CPT-11, a camptothecin analog, in humans," *Pharm. Res.*, 11:S450, 1994a.

Gupta et al., "Correlation of glucuronidation with diarrhea," *Cancer res.*, 54:3723–3725, 1994b.

Hait et al., "Terfenadine (Seldane): a new drug for restoring sensitivity to multidrug resistant cancer cells," *Biochem. Pharmacol.*, 45(2):401–406, 1993.

Harris et al., "Severe 5-fluoro-uracil toxicity secondary to dihydropyrimidine dehydrogenase deficiency: a potentially more common pharmacogenetic syndrome," *Cancer,* 68:499–501, 1991.

Hawkins, "New anticancer agents: taxol, camptothecin analogs, and anthrapyrazoles," *Oncology,* 6(12):17–23, 1992

Hecht et al., "4-(methylnitrosamino)-1-(3-pyridyl)-1-butanol (nnal) and its glucuronide, metabolites of a tobacco-specific lung carcinogen in the urine of black and white smokers," *Proceedings of the American Association for Cancer Research,* 35, 1994

Hjelle, "Hepatic udp-glucuronic acid regulation during acetaminophen biotransformation in rats," *J. Pharmacol. Exp. Ther.*, 237:750–756, 1986.

Horwitz & Horwitz, "Effects of camptothecin on the breakage and repair of DNA during the cell cycle," *Cancer Res.*, 33:2834–2836, 1973.

Hsiang et al., "Camptothecin induces protein-linked DNA breaks via mammalian DNA topoisomerase I," *J. Biol. Chem.*, 27:14873–14878, 1985.

Hunter et al., "Drug absorption limited by P-glycoprotein-mediated secretory drug transport in human intestinal epithelial Caco-2 cell layers," *Pharm. Res.*, 10(5):743–749, 1993.

Ichikawa-Haraguchi et al., "Progesterone and its metabolites: the potent inhibitors of the transporting activity of P-glycoprotein in the adrenal gland," *Biochim. Biophys. Acta,* 1158(3):201–208, 1993.

Inoue et al., "Cellular detoxification of tripeptidyl aldehydes by an aldo-keto reductase," *J. Biol. Chem.*, 268(8):5894–5898, 1993.

Kamimoto et al., "The function of GP170, the multidrug resistance gene product, in rat liver canalicular membrane vesicles," *J. Biol. Chem.*, 264:11693–11698, 1989.

Kamiwatari et al., "Correlation between reversing of multidrug resistance and inhibiting of [3H]azidopine photolabeling of P-glycoprotein by newly synthesized dihydropyridine analogues in a human cell line," *Cancer Res.*, 49(12):3190–3195, 1989.

Kaneda et al., "Metabolism and pharmacokinetics of camptothecin analogue CPT-11 in the mouse," *Cancer Res.*, 50:1715–1720, 1990.

Kaneda & Yokokura, "Nonlinear pharmacokinetics of CPT-11 in rats," *Cancer Res.*, 50:1721–1725, 1990.

Kaplan et al., "Utilization of area under the curve to elucidate the disposition of an extensively biotransformed drug," *J. Pharm. Biopharm.*, 1:201–216, 1973.

Kawato et al., "Intracellular roles of SN-38, a metabolite of the camptothecin derivative CPT-11, in the anti-tumor effect of CPT-11," *Cancer Res.*, 51:4187–4191, 1991.

Kingsbury et al., "Synthesis of water-soluble (aminoalkyl) camptothecin analogues: inhibition of topoisomerase I and antitumor activity," *J Med Chem,* 34(1):98–107, 1991.

Kiue et al., "Activities of newly synthesized dihydropyridines in overcoming of vincristine resistance, calcium antagonism, and inhibition of photoaffinity labeling of P-glycoprotein in rodents," *Cancer Res.*, 50(2):310–317, 1990.

Kunimoto et al., "Antitumor activity of 7-ethyl-10-[4-{1-piperidino)-1-piperidino]carbonyloxy camptothecin, a novel water-soluble derivative of camptothecin against murine tumors," *Cancer Res.*, 47:5944–5947, 1987.

Lannoy et al., "Cyclosporin and quinidine inhibition of renal digoxin excretion: evidence for luminal secretion of digoxin," *Am. J. Physiol.*, 263(4 Pt 2):F613–622, 1992.

Lennard et al., "Pharmacogenetics of acute azathioprine toxicity:
relationship to thiopurine methyltransferase genetic polymorphism," *Clin. Pharmacol. Ther.*, 46:149–154, 1989.

Li et al., "Action of camptothecin on the breakage and repair f DNA during the cell cycle," *Cancer Res.*, 32:2643–2650, 1970.

Lubet et al., "A pleiotropic response to phenobarbital-type enzyme inducers in the f344/ ncr rat," *Biochem. Pharmacol.*, 43(5):1067–1078, 1992.

Magdalou et al., "Peroxisome proliferators as inducers and substrates of udp-glucuronosyltransferases," *Biol. Cell.*, 77(1):13–16, 1993.

Manning & Franklin, "Induction of rat udp-glucuronosyltransferase and glutathione s-transferase activities by 1-buthionine-s, r-sulfoximine without induction of cytochrome p-450," *Toxicology,* 65(1-2):149–159, 1990.

Mattern et. al., "In vitro and in vivo effects of clinically important camptothecin analogues on multidrug-resistant cells," *Oncol Res,* 5(12):467–474, 1993.

Mazzanti et al., "Bile acid inhibition of P-glycoprotein-mediated transport in multidrug-resistant cells and rat liver canalicular membrane vesicles," *Hepatology,* 20(1 Pt 1):170–176, 1994.

McKinney & Hosford, "ATP-stimulated tetraethylammonium transport by rabbit renal brush border membrane vesicles," *J. Biol. Chem.,* 268(10):6886–6895, 1993.

Mechetner & Roninson, "Efficient inhibition of P-glycoprotein-mediated multidrug resistance with a monoclonal antibody," *Proc. Natl. Acad. Sci. USA,* 89(13):5824–5828, 1992.

Miki & Kotake, "Advantages in combination chemotherapy using the camptothecin analogue CPT-11 and cisplatinum analogues for human testicular cancerxenografts," *Hinyokika Kiyo,* 39(12):1221–1225, 1993.

Miller et al., "P-glycoprotein expression in malignant lymphoma and reversal of clinical drug resistance with chemotherapy plus high-dose verapamil," *J. Clin. Oncol.,* 9(1):17–24, 1991.

Miyamoto et al., "Inhibition of multidrug resistance by a new staurosporine derivative, NA-382, in vitro and in vivo," *Cancer Res.,* 53(7):1555–1559, 1993.

Miyamoto et al., "Reversal of vinblastine resistance by a new staurosporine derivative, NA-382, in P388/ADR cells," *Cancer Lett.,* 64(2):177–183, 1992a.

Miyamoto et al., "Multidrug resistance in Yoshida rat ascites hepatoma cell lines," *Anticancer Res.,* 12(3):649–653, 1992b.

Morris et al., "Interaction of forskolin with the P-glycoprotein multidrug transporter," *Biochemistry,* 30(34):8371–8379, 1991.

Muggia et al., "Phase I clinical trial of weekly and daily treatment with camptothecin (NSC 100880): Correlation with preclinical studies," *Cancer Chemother. Rep.,* 56:515–521, 1972.

Muller et al., "ATP-dependent transport of amphiphilic cations across the hepatocyte canalicular membrane mediated by mdr1 P-glycoprotein," *FEBS Lett.,* 343(2):168–172, 1994.

Negoro et al., "Phase I study of weekly intravenous infusion of CPT-11, a new derivative of camptothecin, in the treatment of advanced non-small-cell lung cancer," *J. Natl. Cancer Inst.,* 83:1164–1168, 1991.

Niwa et al., "Effect of a dihydropyridine analogue, 2-[benzyl (phenyl)amino]ethyl 1,4-dihydro-2,6-dimethyl-5-(5,5-dimethyl-2-oxo- 1,3,2-dioxaphosphorinan-2-y 1)-1-(2-morpholinoethyl)-4-(3-nitrophenyl)-3-pyridinecarboxylate on reversing in vivo resistance of tumor cells to adriamycin," *Cancer Res.,* 52(13):3655–3660, 1992.

Ohe et al., "Phase I study and pharmacokinetics of CPT-11 with 5-day continuous infusion," *J. Natl. Cancer Inst.,* 84:972–974, 1992.

Ohi et al., "Intravesical instillation of adriamycin in the presence or absence of verapamil for the treatment of superficial bladder cancer: preliminary report of a collaborative study," *Cancer Chemother Pharmacol,* 30(Suppl):S50-S54, 1992.

Okamura et al., "Digoxin-cyxlosproine interaction: Modulation of the multidrug transporter P-glycoprotein in the kidney," *J. Pharmacol. Exp. Therap.,* 266:1614–1619, 1993.

Patel et al., "Variability of acetaminophen metabolism in caucasians and orientals," *Pharmacogenetics,* 2:38–45, 1992.

Pourtier-Manzanedo et al., "Expression of P-glycoprotein on normal lymphocytes: enhancement of the doxorubicin-sensitivity of concanavalin A-responding mouse spleen cells by P-glycoprotein blockers," *Oncol. Res.,* 4(11–12):473–480, 1992.

Prochaska & Fernandes, "Elevation of serum phase ii enzymes by anticarcinogenic enzyme inducers: markers for a chemoprotected state?" *Carcinogenesis,* 14(12):2441–2443, 1993.

Rajaonarison et. al., "In vitro glucuronidation of 3'-azido-3'-deoxythymidine by human liver," *Drug Metab. Disp.,* 19:809–815, 1993.

Ratain et al., "Paradoxical relationship between acetylator phenotype and amonafide toxicity," *Clin. Pharmacol. Ther.,* 50:573–579, 1991.

Rothenberg et al., "Phase I and pharmacokinetic trial of weekly CPT-11," *J. Clin. Oncol.,* 11:2194–2204, 1993.

Rowinsky et al., "Phase I and pharmacological study of the novel topoisomerase I inhibitor 7-ethyl-10-[4-(1-piperidino)-1-piperidino)carbonyloxycamptot hecin (CPT-11) administered as a ninety-minute infusion every 3 weeks," *Cancer Res.,* 54:427–436, 1994.

Saeki et al., "Human P-glycoprotein transports cyclosporin A and FK506," *J. Biol. Chem.,* 268(9):6077–6080, 1993.

Schinkel et al., "Disruption of the mouse mdrla P-glycoprotein gene leads to a deficiency in the blood-brain barrier and to increased sensitivity to drugs," *Cell,* 77(4):491–502, 1994.

Schinkel et al., "Binding properties of monoclonal antibodies recognizing external epitopes of the human MDR1 P-glycoprotein," *Int. J. Cancer,* 55(3):478–484, 1993.

Shirai et al., "Transport of cyclosporin A across the brain capillary endothelial cell monolayer by P-glycoprotein," *Biochim. Biophys. Acta,* 1222(3):400–404, 1994.

Silber et. al., "Chemosensitivity of lymphocytes from patients with β-cell chronic lymphocytic leukemia to chlorambucil, fludarabine, and camptothecin analogs," *Blood,* 84(10):3440–3446, 1994.

Slichenmyer et. al., "The current status of camptothecin analogues as antitumor agents," *J Natl Cancer Inst,* 85(4):271–291, 1993.

Slichenmyer et. al., "Camptothecin analogues: studies from the Johns Hopkins Oncology Center," *Cancer Chemother Pharmacol,* 34(Suppl):S53–57, 1994.

Sugasawa et. al., "Experiments of synthesis of dl-camptothecin 4:
Synthesis and antileukemic activity of dl-camptothecin analogues," *J Med Chem,* 19(5):675–679, 1976.

Sugimori et. al., "Antitumor agents 7: Synthesis and antitumor activity of novel hexacyclic camptothecin analogues," *J Med Chem,* 37(19):3033–3039, 1994.

Suzuki, "Antitumor drugs and potentiators aiming circumvention of drug resistance," *Gan To Kagaku Ryoho,* 17(3 Pt 1):335–341, 1990.

Takiguchi et. al., "Antitumor effect of camptothecin analog on liver metastatic model of human colon cancer in nude mice," *Gan To Kagaku Ryoho,* 21(5):705–708, 1994.

Tamai & Safa, "Azidopine noncompetitively interacts with vinblastine and cyclosporin A binding to P-glycoprotein in multidrug resistant cells," *J. Biol. Chem.,* 266:16796–16800, 1991.

Tatsuta et al., "Enhancement of activities of anti-tumor drugs by dipyridamole against multidrug-resistant human hepatoma PLC/PRF/5 cells," *Anticancer Drug Des.,* 6(3):179–188, 1991.

Thalhammer et al., "Bile canalicular cationic dye secretion as a model for P-glycoprotein mediated transport," *Eur. J. Pharmacol.,* 270(2–3):213–220, 1994.

Thiebaut et al., "Cellular localization of the multidrug resistance gene product P-glycoprotein in normal human tissues," Proc. Natl. Acad. Sci. USA, 84:7735–7738, 1987.

Trump et al., "High-dose oral tamoxifen, a potential multidrug-resistance-reversal agent: phase I trial in combination with vinblastine," J. Natl. Cancer Inst., 84(23):1811–6, 1992.

Tsuji et al., "CPT-11 converting enzyme from rat serum: purification and some properties," J. Pharmacobio-Dyn., 14:341–349, 1991.

Tsuruo et al., "Antitumor effect of CPT-11, a new derivative of camptothecin against pleiotropic drug-resistant tumors in vitro and in vivo," Cancer Chemother. Pharmacol., 21:71–74, 1988.

Wall et al., "The isolation and structure of camptothecin, a novel alkaloid leukemia and tumor inhibitor from camptotheca acuminata," J. Am. Chem. Soc., 88:3888–3890, 1966.

Wall et. al., "Plant antitumor agents 30: Synthesis and structure activity of novel camptothecin analogs," J Med Chem, 36(18):2689–2700, 1993.

Wani et al., "Plant antitumor agents, 18: Synthesis and biological activity of camptothecin analogues," J. Med. Chem., 23:554–560, 1980.

Wani et. al., "Plant antitumor agents 25: Total synthesis and antileukemic activity of ring A substituted camptothecin analogues. Structure-activity correlations," J Med Chem, 30(10):1774–1779, 1987.

Wilson et al., "A relationship between multidrug resistance and growth-state dependent cytotoxicity of the lysosomotropic detergent N-dodecylimidazole," Biochem. Biophys. Res. Commun., 176(3):1377–1382, 1991.

Zacherl et al., "Inhibition of P-glycoprotein-mediated vinblastine transport across HCT-8 intestinal carcinoma monolayers by verapamil, cyclosporine A and SDZ PSC 833 in dependence on extracellular pH]," Cancer Chemother. Pharmacol., 34(2):125–132, 1994.

What is claimed is:

1. A method for reducing the toxicity of a camptothecin compound, comprising administering said camptothecin compound to an animal in combination with an amount of a second agent effective to reduce excretion of an active camptothecin species through the bile, said second agent increasing glucuronosyltransferase enzyme activity or decreasing the activity of a biliary transport protein.

2. The method of claim 1, wherein said camptothecin compound is a camptothecin analogue having a substitution at the 7, 9 or 10 positions.

3. The method of claim 1, wherein said camptothecin compound is topotecan, 9-amino-camptothecin, 9-nitro-camptothecin, GG211 or irinotecan.

4. The method of claim 3, wherein said camptothecin compound is irinotecan.

5. The method of claim 1, wherein said second agent increases glucuronosyltransferase enzyme activity.

6. The method of claim 1, wherein said second agent is a dithiolethione.

7. The method of claim 6, wherein said second agent is Oltipraz.

8. The method of claim 1, wherein said second agent is an aryloxycarboxylic acid, an arylcarboxylic acid, a chlorophenoxycarboxylic acid or a fibric acid.

9. The method of claim 8, wherein said second agent is clofibrate, ciprofibrate, fenofibrate, bezafibrate, gemfibrazol, tiadenol or probucol.

10. The method of claim 1, wherein said second agent is phenobarbital, dilantin, clonazepam, clotrimazole, buthionine sulfoximine, cyclophosphamide, ifosphamide, a retinoic acid, rifampin or disulfiram.

11. The method of claim 1, wherein said second agent is a corticosteroid.

12. The method of claim 1, wherein said second agent is an oral contraceptive.

13. The method of claim 1, wherein said second agent decreases the activity of a biliary transport protein.

14. The method of claim 13, wherein said second agent decreases the activity of p-lycoprotein.

15. The method of claim 13, wherein said second agent is a cyclosporine, cephalosporin or a staurosporine.

16. The method of claim 15, wherein said second agent is SDZ 280 446, 3'-Keto-cyclosporin D, cefoperazone or staurosporine.

17. The method of claim 15, wherein said second agent is Cyclosporine A, SDZ PSC 833 or N-ethoxycarbonyl-7-oxo-staurosporine.

18. The method of claim 13, wherein said second agent is a calcium channel blocker.

19. The method of claim 18, wherein said second agent is a dihydropyridine analogue, verapamil, dex verapamil, tiapamil, nifedipine, diltiazem, nicardipine, nisoldipine, nimodipine or nitrendipine.

20. The method of claim 13, wherein said second agent is a calmodulin antagonist.

21. The method of claim 20, wherein said second agent is trans-flupenthixol, cis-flupenthixol, clorpenthixol, fluphenazine, chlorpromazine, triflupromazine, trifluoperazine, prochlorperazine or thioridazine.

22. The method of claim 13, wherein said second agent is progesterone, a progesterone metabolite, pregnenolone, RU 486 or tirilazad.

23. The method of claim 13, wherein said second agent is an anti-neoplastic agent.

24. The method of claim 23, wherein said second agent is vincristine, vinblastine, actinomycin D, colchicine, etoposide, daunomycin, daunorubicin, doxorubicin, taxotere, taxol or tamoxifen.

25. The method of claim 13, wherein said second agent is reserpine, dipyridamole, chloroquine, propranolol, terfenadine, ivermectin or quinidine.

26. The method of claim 14, wherein said second agent is an antibody that binds to p-glycoprotein.

27. The method of claim 1, comprising administering said camptothecin compound in combination with a second agent that increases glucuronosyltransferase enzyme activity and a third agent that decreases biliary transport protein activity.

28. The method of claim 17, wherein said second agent is Cyclosporine A.

29. A method for reducing the toxicity of a camptothecin compound, comprising administering said camptothecin compound to an animal in combination with an amount of Cyclosporine A effective to reduce excretion of an active camptothecin species through the bile by decreasing the activity of a biliary transport protein.

30. A method for reducing the toxicity of irinotecan, comprising administering said irinotecan to an animal in combination with an amount of Cyclosporine A effective to reduce excretion of an active irinotecan species through the bile by decreasing the activity of a biliary transport protein.

* * * * *

UNITED STATES PATENT AND TRADEMARK OFFICE
CERTIFICATE OF CORRECTION

PATENT NO. : 5,786,344

DATED : July 28, 1998

INVENTOR(S) : Mark J. Ratain and Elora Gupta

It is certified that error appears in the above-identified patent and that said Letters Patent is hereby corrected as shown below:

In claim 14, column 68, line 12, delete "p-lycoprotein" and insert --p-glycoprotein--.

Signed and Sealed this

Fifteenth Day of December, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,786,344

DATED        : July 28, 1998

INVENTOR(S)  : Mark J. Ratain and Elora Gupta

It is certified that error appears in the above-identified patent and that said Letters Patent is hereby corrected as shown below:

On the title page, item [56], under "FOREIGN PATENT DOCUMENTS", insert -- WO 95/08986  04/06/95  PCT --.

Signed and Sealed this

Fifth Day of January, 1999

Attest:

Attesting Officer

Acting Commissioner of Patents and Trademarks